(12) United States Patent
Malek

(10) Patent No.: US 12,084,483 B2
(45) Date of Patent: Sep. 10, 2024

(54) INTERLEUKIN-2/INTERLEUKIN-2 RECEPTOR ALPHA FUSION PROTEINS AND METHODS OF USE

(71) Applicant: UNIVERSITY OF MIAMI, Miami, FL (US)

(72) Inventor: Thomas Malek, Miami Beach, FL (US)

(73) Assignee: University of Miami, Miami, FL (US)

( * ) Notice: Subject to any disclaimer, the term of this patent is extended or adjusted under 35 U.S.C. 154(b) by 158 days.

(21) Appl. No.: 15/501,392

(22) PCT Filed: Aug. 5, 2015

(86) PCT No.: PCT/US2015/043792
§ 371 (c)(1),
(2) Date: Feb. 2, 2017

(87) PCT Pub. No.: WO2016/022671
PCT Pub. Date: Feb. 11, 2016

(65) Prior Publication Data
US 2017/0233448 A1     Aug. 17, 2017

Related U.S. Application Data

(60) Provisional application No. 62/033,726, filed on Aug. 6, 2014.

(51) Int. Cl.
| | |
|---|---|
| *A61K 38/20* | (2006.01) |
| *C07K 14/55* | (2006.01) |
| *C07K 14/715* | (2006.01) |
| *A61K 38/00* | (2006.01) |

(52) U.S. Cl.
CPC .......... *C07K 14/55* (2013.01); *C07K 14/7155* (2013.01); *A61K 38/00* (2013.01); *C07K 2319/00* (2013.01); *C07K 2319/21* (2013.01)

(58) Field of Classification Search
CPC .............................. C07K 14/55; C07K 2319/00
See application file for complete search history.

(56) References Cited

U.S. PATENT DOCUMENTS

| | | | |
|---|---|---|---|
| 4,522,811 A | 6/1985 | Eppstein et al. | |
| 4,873,192 A | 10/1989 | Kunkel | |
| 5,250,296 A * | 10/1993 | Ootsu ................ | A61K 38/2013 424/85.2 |
| 5,605,793 A | 2/1997 | Stemmer | |
| 5,837,458 A | 11/1998 | Minshull et al. | |
| 6,967,092 B1 * | 11/2005 | Mc Kearn ............ | C07K 14/475 435/252.3 |
| 9,359,415 B2 * | 6/2016 | Alvarez ........... | C07K 14/57563 |
| 2004/0265272 A1 | 12/2004 | Iwamoto | |
| 2006/0160187 A1 | 7/2006 | Denis-Mize et al. | |
| 2006/0263857 A1 * | 11/2006 | Lefrancois ......... | C07K 14/5443 435/69.52 |
| 2006/0269515 A1 | 11/2006 | Denis-Mize et al. | |
| 2013/0336924 A1 * | 12/2013 | Alvarez ........... | C07K 14/70503 424/85.2 |
| 2013/0344080 A1 | 12/2013 | Zarrin et al. | |

FOREIGN PATENT DOCUMENTS

| | | |
|---|---|---|
| CN | 101255197 A | 9/2008 |
| EP | 75444 A2 | 3/1983 |
| EP | 0307285 A1 | 3/1989 |
| JP | H 10-511846 A | 11/1998 |
| JP | 2008-545397 A | 12/2008 |
| JP | 6723982 B2 | 7/2020 |
| WO | WO-199620277 A | 7/1996 |
| WO | WO-1999/60128 A1 | 11/1999 |
| WO | WO-2003029475 A | 4/2003 |
| WO | WO-2007001677 A | 1/2007 |
| WO | WO-2010/020766 A2 | 8/2008 |
| WO | WO-2011/123683 A2 | 10/2011 |
| WO | WO-2013/184942 A1 | 12/2013 |
| WO | WO-2014/023752 A1 | 2/2014 |
| WO | WO-2014101287 A1 | 7/2014 |

OTHER PUBLICATIONS

Nikaido et al. Molecular cloning of cDNA encoding human interleukin-2 receptor. Nature. Oct. 18-24, 1984;311(5987):631-5.*
Robb et al. Structure-function relationships for the interleukin 2 receptor: Location of ligand and antibody binding sites on the Tac receptor chain by mutational analysis. Proc. Natl. Acad. Sci. USA, 85:5654-5658, 1988.*
Rao et al. High-affinity CD25-binding IL-2 mutants potently stimulate persistent T cell growth. Biochemistry. Aug. 9, 2005;44(31):10696-701.*
Aoyama et al. Low-dose IL-2 for In vivo expansion of CD4+ and CD8+ regulatory T cells in nonhuman primates. Am J Transplant. Sep. 2012; 12(9):2532-7.*
Koreth et al. Interleukin-2 and Regulatory T Cells in Graft-versus-Host Disease. N Engl J Med. Dec. 1, 2011; 365(22): 2055-66.*

(Continued)

*Primary Examiner* — Dong Jiang

(74) *Attorney, Agent, or Firm* — Sterne, Kessler, Goldstein & Fox P.L.L.C.

(57) ABSTRACT

Various methods and compositions are provided which can be employed to modulate the immune system. Compositions include a fusion protein comprising: (a) a first polypeptide comprising Interleukin-2 (IL-2) or a functional variant or fragment thereof; and (b) a second polypeptide, fused in frame to the first polypeptide, wherein the second polypeptide comprises an extracellular domain of Interleukin-2 Receptor alpha (IL-2Rα) or a functional variant or fragment thereof, and wherein the fusion protein has IL-2 activity. Various methods are provided for modulating the immune response in a subject comprising administering to a subject in need thereof a therapeutically effective amount of the IL-2/IL-2Rα fusion protein disclosed herein.

15 Claims, 16 Drawing Sheets
Specification includes a Sequence Listing.

(56) References Cited

OTHER PUBLICATIONS

Castela et al. Effects of Low-Dose Recombinant Interleukin 2 to Promote T-Regulatory Cells in Alopecia Areata. JAMA Dermatol. Jul. 2014; 150(7):748-51.*
Buchwald et al., Long-term, continuous intravenous heparin administration by an implantable infusion pump in ambulatory patients with recurrent venous thrombosis, *Surgery*, 88:507-16 (1980).
Centers for Disease Control and Prevention (CDC), FDA approval for infants of a Haemophilus influenzae type b conjugate and hepatitis B (recombinant) combined vaccine, *MMWR Morb. Mortal. Wkly. Rep.*, 46:107-9 (1997).
Crameri et al., DNA shuffling of a family of genes from diverse species accelerates directed evolution, *Nature*, 391:288-91(1998).
Crameri et al., Long-term, continuous intravenous heparin administration by an implantable infusion pump in ambulatory patients with recurrent venous thrombosis, *Nature Biotech*, 15:436-8 (1997).
During et al., Controlled Release of Dopamine from a Polymeric Brain Implant: In Vivo Characterization, *Ann. Neurol.*, 25:351-56 (1989).
Gait ed., Oligonucleotide Synthesis; A Practical Approach, IRL Press, MRC Laboratory of Molec. Biol., (1984).
GenBank Accession No. NM_001003211.1, Canis lupus familiaris interleukin 2 receptor, alpha (IL2RA), mRNA, dated Feb. 23, 2014.
GenBank Accession No. NP_001028089.1, interleukin-2 receptor subunit alpha precursor [Macaca mulatta], dated Mar. 2, 2017.
GenBank Accession No. NP_001030597.1, interleukin-2 receptor subunit alpha precursor [Pan troglodytes], dated Sep. 21, 2016.
GenBank Accession No. NP_032393.3, interleukin-2 receptor subunit alpha precursor [Mus musculus], dated Feb. 15, 2015.
GenBank Accession No. NP_037295.1, interleukin-2 receptor subunit alpha precursor [Rattus norvegicus], dated Mar. 2, 2017.
GenBank Accession No. NP_776783.1, interleukin-2 receptor subunit alpha precursor [Bos taurus], dated Sep. 13, 2016.
GenBank Accession No. P05016, RecName: Full=Interleukin-2; Short=IL-2; AltName: Full=T-cell growth factor; Short=TCGF; Flags: Precursor, dated Mar. 15, 2017.
GenBank Accession No. P36835, RecName: Full=Interleukin-2; Short=IL-2; AltName: Full=T-cell growth factor; Short=TCGF; Flags: Precursor, dated Mar. 15, 2017.
GenBank Accession No. P37997, RecName: Full=Interleukin-2; Short=IL-2; AltName: Full=T-cell growth factor; Short=TCGF; Flags: Precursor, dated Mar. 15, 2017.
GenBank Accession No. Q29416, RecName: Full=Interleukin-2; Short=IL-2; AltName: Full=T-cell growth factor; Short=TCGF; Flags: Precursor, dated Mar. 15, 2017.
GenBank Accession No. Q7JFM2, RecName: Full=Interleukin-2; Short=IL-2; AltName: Full=T-cell growth factor; Short=TCGF; Flags: Precursor, dated Mar. 15, 2017.
GenBank Accession No. Q7JFM5, RecName: Full=Interleukin-2; Short=IL-2; AltName: Full=T-cell growth factor; Short=TCGF; Flags: Precursor, dated Mar. 15, 2017.
Howard et al., Intracerebral drug delivery in rats with lesion-induced memory deficits, *J. Neurosurg.*, 71:105-12 (1989).
Kunkel et al., Rapid and efficient site-specific mutagenesis without phenotypic selection, *Methods in Enzymol.*, 154:367-82 (1987).
Kunkel, Rapid and efficient site-specific mutagenesis without phenotypic selection. *Proc. Natl. Acad. Sci. USA*, 82:488-92 (1985).
Langer, New methods of drug delivery, *Science*, 249:1527-33 (1990).
Levy et al., Inhibition of calcification of bioprosthetic heart valves by local controlled-release diphosphonate, *Science*, 228:190-2 (1985).
Malek et al., Interleukin-2 receptor signaling: at the interface between tolerance and immunity, *Immunity*, 33(2):153-65 (2010).
Malek et al., The murine interleukin 2 receptor. IV. Biochemical characterization, *J. Immunol.*, 136:4092-8 (1986).
Robb et al., Structure-function relationships for the interleukin 2 receptor: location of ligand and antibody binding sites on the Tac receptor chain by mutational analysis, *Proc. Natl. Acad. Sci. USA*, 85:5654-8 (1988).

Sambrook et al., Molecular Cloning: A Laboratory Manual, Cold Spring Harbor Laboratory Press, (1989).
Saudek et al., A preliminary trial of the programmable implantable medication system for insulin delivery, *N. Engl. J. Med.*, 321:574-79 (1989).
Sefton, Implantable pumps, *Crit. Rev. Biotned. Eng.*, 14:201-40 (1987).
Speck et al., Vaccines for the prevention of human papillomavirus infections, *Skin Therapy Lett.*, 11:1-3 (2006).
Stemmer, DNA shuffling by random fragmentation and reassembly in vitro recombination for molecular evolution., *Proc. Natl. Acad. Sci. USA*, 91:10747-51 (1994).
Zhang et al., Directed evolution of a fucosidase from a galactosidase by DNA shuffling and screening, *Proc. Natl. Acad. Sci. USA*, 94:4504-4509 (1997).
Melder et al., Pharmacokinetics and in vitro and in vivo anti-tumor response of an interleukin-2-human serum albumin fusion protein in mice, Can. Immunol. Immunother., 54(6):535-47 (2005).
Millington et al., Effects of an agonist interleukin-2/Fc fusion protein, a mutant antagonist interleukin-15/Fc fusion protein, and sirolimus on cardiac allograft survival in non-human primates, J. Heart Lung Transplant, 31(4):427-35 (2012).
Puskas et al., Development of an attenuated interleukin-2 fusion protein that can be activated by tumour-expressed proteases, Immunol., 133(2):206-20 (2011).
Stoklasek et al., Combined IL-15/IL15-Ralpha immunotherapy maximized IL-15 activity in vivo, J. Immunol., 177(9):6072-80 (2006).
Wilkinson et al., A ligand-receptor fusion of growth hormone forms a dimer and is a potent long-acting agonist, Nat. Med., 13(9):1108-13 (2007).
International Search Report and Written Opinion of the International Search Authority, European Patent Office, PCT/US2015/043792, mailed Nov. 20, 2015.
International Preliminary Report on Patentability, European Patent Office, PCT/US2015/043792, mailed Feb. 7, 2017.
Lowenthal et al., "Contrasting Interleukin 2 Binding Properties of the α (p55) and ß (p70) Protein Subunits of the Human High-Affinity Interleukin 2 Receptor," *J Exp Med*. 166(4): 1156-1161 (1987).
Wang et al., "The Interleukin 2 RECEPTOR—Functional Consequences of its Bimolecular Structure," *J Exp Med*. 166(4):1055-69 (1987).
International Search Report and Written Opinion of the International Search Authority, European Patent Office, PCT/US2019/024376, mailed Jun. 13, 2019.
Fehinger, T., et al., "Interleukin 15: biology and relevance to human disease," Blood 97(1):14-32, American Society of Hematology, United States (2001).
Giri, J., et al., "IL-15 a novel T cell growth factor that shares activities and receptor components with IL-2," Journal of Leukocyte Biology 5:763-766, Society for Leukocyte Biology, United States (1995).
Rickert, M., et al., "The Structure of Interleukin-2 Complexed with Its Alpha Receptor," Science 308(5727):1477-1480, Nature Publishing Group, United Kingdom (2005).
Rubinstein, M.P., et al., "Converting IL-15 to a superagonist by binding to soluble IL-15R≠," PNAS 103(24):9166-9171, Proceedings of the National Academy of Sciences , United States (2006).
Co-Pending United States U.S. Appl. No. 16/435,420, Inventors Struthers, Mary, et al., filed Jun. 7, 2019 (Unpublished).
Co-Pending United States U.S. Appl. No. 16/366,838, Inventors Struthers, Mary, et al., filed Mar. 27, 2019 (Unpublished).
Lopes et al. "ALKS 4230: a novel engineered IL-2 fusion protein with an improved cellular selectivity profile for cancer immunotherapy," *J Immunotherapy of Cancer*. 8:e000673: 1-13 (2020).
Ward et al. "IL-2/CD25: A Long-Acting Fusion Protein That Promotes Immune Tolerance by Selectively Targeting the IL-2 Receptor on Regulatory T Cells," *J Immunol*. 201: 2579-2592 (2018).
Deoca et al. "Low-Zone IL-2 Signaling: Fusion Proteins Containing Linked CD25 and IL-2 Domains Sustain Tolerogenic Vaccination *in*

(56) References Cited

OTHER PUBLICATIONS

*vivo* and Promote Dominance of FOXP3$^+$Tregs *in vitro*," *Front. Immunol.* 11:541619: 1-24 (2020).

\* cited by examiner

| Construct | Deduced protein Sequence |
|---|---|
| IL-2 | MYSMQLASCVTLTLVLLVNSAPTSSSTSSSTAEAQQQQQQQQQQQQQHLEQLLMDLQELLS |
| IL-2-(G4S)4-IL-2Rα | MDSMQLASCVTLTLVLLVNSAPTSSSTSSSTAEAQQQQ-QQQQQQQHLEQLLMDLQELLS |
| IL-2-(G4S)5-IL-2Rα | MDSMQLASCVTLTLVLLVNSAPTSSSTSSSTAEAQQQQ-QQQQQQQHLEQLLMDLQELLS |
| IL-2-(G3S)4-IL-2Rα | MDSMQLASCVTLTLVLLVNSAPTSSSTSSSTAEAQQQQ-QQQQQQQHLEQLLMDLQELLS |
| IL-2-(G3S)3-IL-2Rα | MDSMQLASCVTLTLVLLVNSAPTSSSTSSSTAEAQQQQ-QQQQQQQHLEQLLMDLQELLS |
| IL-2Rα | ------------------------------------------------------------ |
| | |
| IL-2 | RMENYRNLKLPRMLTFKFYLPKQATELKDLQCLEDELGPLRHVLDLTQSKSFQLEDAENF |
| IL-2-(G4S)4-IL-2Rα | RMENYRNLKLPRMLTFKFYLPKQATELKDLQCLEDELGPLRHVLDLTQSKSFQLEDAENF |
| IL-2-(G4S)5-IL-2Rα | RMENYRNLKLPRMLTFKFYLPKQATELKDLQCLEDELGPLRHVLDLTQSKSFQLEDAENF |
| IL-2-(G3S)4-IL-2Rα | RMENYRNLKLPRMLTFKFYLPKQATELKDLQCLEDELGPLRHVLDLTQSKSFQLEDAENF |
| IL-2-(G3S)3-IL-2Rα | RMENYRNLKLPRMLTFKFYLPKQATELKDLQCLEDELGPLRHVLDLTQSKSFQLEDAENF |
| IL-2Rα | ------------------------------------------------------------ |
| | |
| IL-2 | ISNIRVTVVKLKGSDNTFECQFDDESATVVDFLRRWIAFCQSIISTSPQ----------- |
| IL-2-(G4S)4-IL-2Rα | ISNIRVTVVKLKGSDNTFECQFDDESATVVDFLRRWIAFCQSIISTSPQGGGGSGGGGS- |
| IL-2-(G4S)5-IL-2Rα | ISNIRVTVVKLKGSDNTFECQFDDESATVVDFLRRWIAFCQSIISTSPQGGGGSGGGGSG |
| IL-2-(G3S)4-IL-2Rα | ISNIRVTVVKLKGSDNTFECQFDDESATVVDFLRRWIAFCQSIISTSPQGGGSGGGS--- |
| IL-2-(G3S)3-IL-2Rα | ISNIRVTVVKLKGSDNTFECQFDDESATVVDFLRRWIAFCQSIISTSPQGGGSGG----- |
| IL-2Rα | ------------------------------------------------------------ |
| | |
| IL-2 | ------------------------------------------------------------ |
| IL-2-(G4S)4-IL-2Rα | ----GGGGSGGGGSELCLYDPPEVPNATFKALSYKNGTILNCECKRGFRRLKELVYMRCL |
| IL-2-(G4S)5-IL-2Rα | GGGSGGGGSGGGGSELCLYDPPEVPNATFKALSYKNGTILNCECKRGFRRLKELVYMRCL |
| IL-2-(G3S)4-IL-2Rα | ------GGGSGGGSELCLYDPPEVPNATFKALSYKNGTILNCECKRGFRRLKELVYMRCL |
| IL-2-(G3S)3-IL-2Rα | -------GSGGGSELCLYDPPEVPNATFKALSYKNGTILNCECKRGFRRLKELVYMRCL |
| IL-2Rα | -------------ELCLYDPPEVPNATFKALSYKNGTILNCECKRGFRRLKELVYMRCL |
| | |
| IL-2 | ------------------------------------------------------------ |
| IL-2-(G4S)4-IL-2Rα | GNSWSSNCQCTSNSHDKSRKQVTAQLEHQKEQQTTTDMQKPTQSMHQENLTGHCREPPPW |
| IL-2-(G4S)5-IL-2Rα | GNSWSSNCQCTSNSHDKSRKQVTAQLEHQKEQQTTTDMQKPTQSMHQENLTGHCREPPPW |
| IL-2-(G3S)4-IL-2Rα | GNSWSSNCQCTSNSHDKSRKQVTAQLEHQKEQQTTTDMQKPTQSMHQENLTGHCREPPPW |
| IL-2-(G3S)3-IL-2Rα | GNSWSSNCQCTSNSHDKSRKQVTAQLEHQKEQQTTTDMQKPTQSMHQENLTGHCREPPPW |
| IL-2Rα | GNSWSSNCQCTSNSHDKSRKQVTAQLEHQKEQQTTTDMQKPTQSMHQENLTGHCREPPPW |
| | |
| IL-2 | ------------------------------------------------------------ |
| IL-2-(G4S)4-IL-2Rα | KHEDSKRIYHFVEGQSVHYECIPGYKALQRGPAISICKMKCGKTGWTQPQLTCVDEREHH |
| IL-2-(G4S)5-IL-2Rα | KHEDSKRIYHFVEGQSVHYECIPGYKALQRGPAISICKMKCGKTGWTQPQLTCVDEREHH |
| IL-2-(G3S)4-IL-2Rα | KHEDSKRIYHFVEGQSVHYECIPGYKALQRGPAISICKMKCGKTGWTQPQLTCVDEREHH |
| IL-2-(G3S)3-IL-2Rα | KHEDSKRIYHFVEGQSVHYECIPGYKALQRGPAISICKMKCGKTGWTQPQLTCVDEREHH |
| IL-2Rα | KHEDSKRIYHFVEGQSVHYECIPGYKALQRGPAISICKMKCGKTGWTQPQLTCVDEREHH |
| | |
| IL-2 | ------------------------------------------------------------ |
| IL-2-(G4S)4-IL-2Rα | RFLASEESQGSRNSSPESETSCPITTTDFPQPTETTAMTETFVLTMEYKGGHHHHHH |
| IL-2-(G4S)5-IL-2Rα | RFLASEESQGSRNSSPESETSCPITTTDFPQPTETTAMTETFVLTMEYKGGHHHHHH |
| IL-2-(G3S)4-IL-2Rα | RFLASEESQGSRNSSPESETSCPITTTDFPQPTETTAMTETFVLTMEYKGGHHHHHH |
| IL-2-(G3S)3-IL-2Rα | RFLASEESQGSRNSSPESETSCPITTTDFPQPTETTAMTETFVLTMEYKGGHHHHHH |
| IL-2Rα | RFLASEESQGSRNSSPESETSCPITTTDFPQPTETTAMTETFVLTMEYK-------- |

FIG. 2A

```
IL-2                  MYRMQLLSCIALSLALVTNSAPTSSSTKKTQLQLEHLLLDLQMILNGINNYKNPKLTRML
IL-2-(G3S)2-IL-2Rα    MDRMQLLSCIALSLALVTNSAPTSSSTKKTQLQLEHLLLDLQMILNGINNYKNPKLTRML
IL-2-(G3S)3-IL-2Rα    MDRMQLLSCIALSLALVTNSAPTSSSTKKTQLQLEHLLLDLQMILNGINNYKNPKLTRML
IL-2-(G3S)4-IL-2Rα    MDRMQLLSCIALSLALVTNSAPTSSSTKKTQLQLEHLLLDLQMILNGINNYKNPKLTRML
IL-2-(G4S)4-IL-2Rα    MDRMQLLSCIALSLALVTNSAPTSSSTKKTQLQLEHLLLDLQMILNGINNYKNPKLTRML
IL-2Rα                ------------------------------------------------------------

IL-2                  TFKFYMPKKATELKHLQCLEEELKPLEEVLNLAQSKNFHLRPRDLISNINVIVLELKGSE
IL-2-(G3S)2-IL-2Rα    TFKFYMPKKATELKHLQCLEEELKPLEEVLNLAQSKNFHLRPRDLISNINVIVLELKGSE
IL-2-(G3S)3-IL-2Rα    TFKFYMPKKATELKHLQCLEEELKPLEEVLNLAQSKNFHLRPRDLISNINVIVLELKGSE
IL-2-(G3S)4-IL-2Rα    TFKFYMPKAATELKHLQCLEEELKPLEEVLNLAQSKNFHLRPRDLISNINVIVLELKGSE
IL-2-(G4S)4-IL-2Rα    TFKFYMPKAATELKHLQCLEEELKPLEEVLNLAQSKNFHLRPRDLISNINVIVLELKGSE
IL-2Rα                ------------------------------------------------------------

IL-2                  TTFMCEYADETATIVEFLNRWITFCQSIISTLT---------------------------
IL-2-(G3S)2-IL-2Rα    TTFMCEYADETATIVEFLNRWITFCQSIISTLTGGGS-------------GGGSELCDDDP
IL-2-(G3S)3-IL-2Rα    TTFMCEYADETATIVEFLNRWITFCQSIISTLTGGGS--------GGGSGGGSELCDDDP
IL-2-(G3S)4-IL-2Rα    TTFMCEYADETATIVEFLNRWITFCQSIISTLTGGGSGGGS---SGGGSGGGSELCDDDP
IL-2-(G4S)4-IL-2Rα    TTFMCEYADETATIVEFLNRWITFCQSIISTLTGGGGSGGGGSGGGGSGGGGSELCDDDP
IL-2Rα                -----------------------------------------------------ELCDDDP

IL-2                  PEIPHATFKAMAYKEGTMLNCECKRGFRRIKSGSLYMLCTGNSSHSSWDNQCQCTSSATR
IL-2-(G3S)2-IL-2Rα    PEIPHATFKAMAYKEGTMLNCECKRGFRRIKSGSLYMLCTGNSSHSSWDNQCQCTSSATR
IL-2-(G3S)3-IL-2Rα    PEIPHATFKAMAYKEGTMLNCECKRGFRRIKSGSLYMLCTGNSSHSSWDNQCQCTSSATR
IL-2-(G3S)4-IL-2Rα    PEIPHATFKAMAYKEGTMLNCECKRGFRRIKSGSLYMLCTGNSSHSSWDNQCQCTSSATR
IL-2-(G4S)4-IL-2Rα    PEIPHATFKAMAYKEGTMLNCECKRGFRRIKSGSLYMLCTGNSSHSSWDNQCQCTSSATR
IL-2Rα                ------------------------------------------------------------

IL-2                  ------------------------------------------------------------
IL-2-(G3S)2-IL-2Rα    RTTKQVTPQPEEQKERKTTEMQSPMQFVDQASLPGHCREPPPWENEATERIYHFVVGQMV
IL-2-(G3S)3-IL-2Rα    RTTKQVTPQPEEQKERKTTEMQSPMQFVDQASLPGHCREPPPWENEATERIYHFVVGQMV
IL-2-(G3S)4-IL-2Rα    RTTKQVTPQPEEQKERKTTEMQSPMQFVDQASLPGHCREPPPWENEATERIYHFVVGQMV
IL-2-(G4S)4-IL-2Rα    RTTKQVTPQPEEQKERKTTEMQSPMQFVDQASLPGHCREPPPWENEATERIYHFVVGQMV
IL-2Rα                RTTKQVTPQPEEQKERKTTEMQSPMQFVDQASLPGHCREPPPWENEATERIYHFVVGQMV

IL-2                  ------------------------------------------------------------
IL-2-(G3S)2-IL-2Rα    YYQCVQGYRALHRGPAESVCKMTHGKTRWTQPQLICTGEMETSQFPGEEKPQASPEGRPE
IL-2-(G3S)3-IL-2Rα    YYQCVQGYRALHRGPAESVCKMTHGKTRWTQPQLICTGEMETSQFPGEEKPQASPEGRPE
IL-2-(G3S)4-IL-2Rα    YYQCVQGYRALHRGPAESVCKMTHGKTRWTQPQLICTGEMETSQFPGEEKPQASPEGRPE
IL-2-(G4S)4-IL-2Rα    YYQCVQGYRALHRGPAESVCKMTHGKTRWTQPQLICTGEMETSQFPGEEKPQASPEGRPE
IL-2Rα                YYQCVQGYRALHRGPAESVCKMTHGKTRWTQPQLICTGEMETSQFPGEEKPQASPEGRPE

IL-2                  ----------------------------------------
IL-2-(G3S)2-IL-2Rα    SETSCLVTTDPQIQTEMAATMETSIFTTEYQGGHHHHHH
IL-2-(G3S)3-IL-2Rα    SETSCLVTTDPQIQTEMAATMETSIFTTEYQGGHHHHHH
IL-2-(G3S)4-IL-2Rα    SETSCLVTTDPQIQTEMAATMETSIFTTEYQGGHHHHHH
IL-2-(G4S)4-IL-2Rα    SETSCLVTTDPQIQTEMAATMETSIFTTEYQGGHHHHHH
IL-2Rα                SETSCLVTTDPQIQTEMAATMETSIFTTEYQ--------
```

FIG. 2B

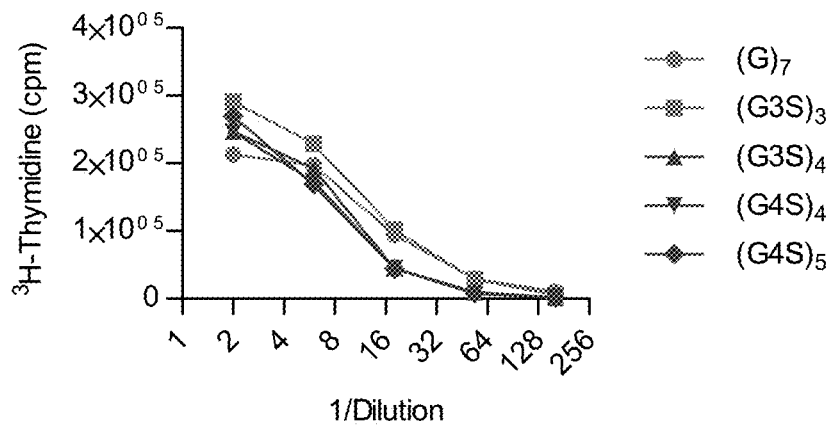
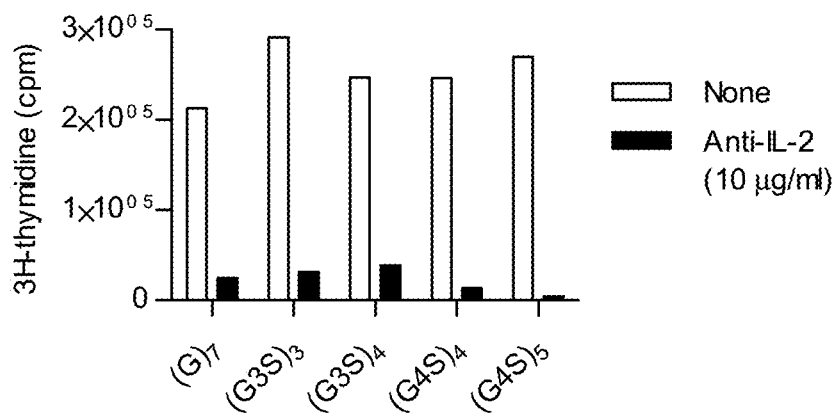
FIG. 3

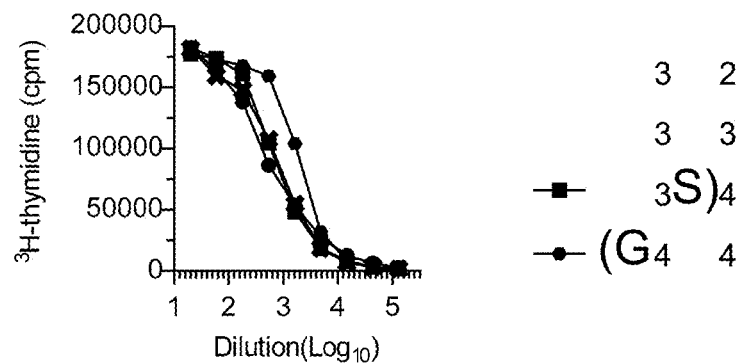
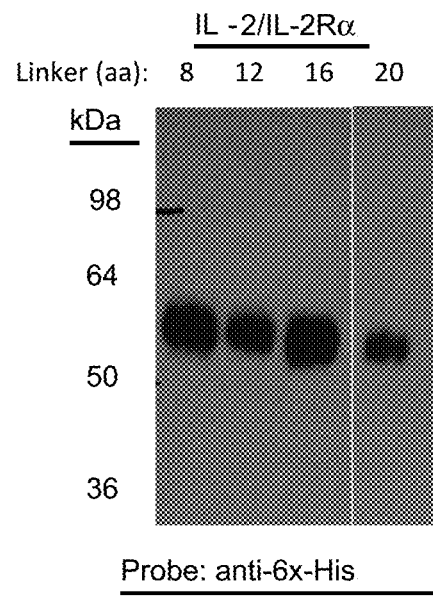
FIG. 13

INTERLEUKIN-2/INTERLEUKIN-2 RECEPTOR ALPHA FUSION PROTEINS AND METHODS OF USE

STATEMENT OF FEDERAL FUNDING

This invention was made with government support under grant number R01 DK093866, awarded by the National Institute of Health (NIH), National Institute of Diabetes and Digestive and Kidney Diseases (NIDDK). The government has certain rights in the invention.

FIELD OF THE INVENTION

The presently disclosed subject matter generally relates to methods and compositions for modulating the immune response employing an Interleukin-2/Interleukin-2 Receptor alpha fusion protein.

REFERENCE TO SEQUENCE LISTING SUBMITTED ELECTRONICALLY

The content of the electronically submitted sequence listing (Name: 3338_0970001_Updated_SL.txt; Size: 147,837 bytes; and Date of Creation: May 11, 2017) is herein incorporated by reference in its entirety.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 464173seq1ist.txt, a creation date of Jul. 30, 2015 and a size of 139 KB. The sequence listing filed via EFS-Web is part of the specification and is hereby incorporated in its entirety by reference herein.

BACKGROUND OF THE INVENTION

Interleukin-2 (IL-2) is a biologic that has been used in attempts to boost immune responses in cancer and HIV/AID patients. More recently lower doses of IL-2 have been used to selectively boost tolerance to suppress unwanted immune responses associated with autoimmune-like attack of self tissues. Importantly, these low doses of IL-2 have not shown any signs of enhancing or re-activation of autoreactive T cells. Nevertheless, IL-2 has important drawbacks as a therapeutic, including a very short-half life in vivo, which limits its efficacy, and toxicity at high doses. For these reasons new IL-2 biologics are needed having improved pharmacokinetics and durability of responses for use.

SUMMARY OF THE INVENTION

Various methods and compositions are provided which can be employed to modulate the immune system. Compositions include a fusion protein comprising: (a) a first polypeptide comprising Interleukin-2 (IL-2) or a functional variant or fragment thereof; and (b) a second polypeptide, fused in frame to the first polypeptide, wherein the second polypeptide comprises an extracellular domain of Interleukin-2 Receptor alpha (IL-2Rα) or a functional variant or fragment thereof, and wherein the fusion protein has IL-2 activity.

Various methods are provided for decreasing the immune response in a subject comprising administering to a subject in need of a decrease in the immune response a therapeutically effective amount of the IL-2/IL-2Rα fusion protein disclosed herein.

Further provided are methods for increasing the immune response in a subject comprising administering to a subject in need of an increase in the immune response a therapeutically effective amount of the IL-2/IL-2Rα fusion protein disclosed herein. Further provided are methods for increasing T regulatory cell activity.

Additional methods including enhancing the immunogenicity of a vaccine or overcoming a suppressed immune response to a vaccine in a subject, comprising: (a) administering to the subject a therapeutically effective amount of the IL-2/IL-2Rα fusion protein disclosed herein; and, (b) administering to the subject a vaccine, wherein the fusion protein enhances the immunogenicity of the vaccine or overcomes the suppressed immune response to the vaccine.

BRIEF DESCRIPTION OF THE DRAWINGS

FIG. 2A and FIG. 2B provide the deduced protein sequences of non-limiting examples of IL-2/IL-2Rα fusion proteins. FIG. 2A provides the deduced protein sequences of non-limiting examples of mouse IL-2/IL-2Rα fusion proteins. The sequences of mouse IL-2 and IL-2Rα are shown above and below, respectively, of the fusion proteins. The sequence denoted as IL-2 is set forth in SEQ ID NO: 3; the sequence denoted as IL-2-(G4S)4-IL-2Rα is set forth in SEQ ID NO: 54; the sequence denoted as IL-2-(G4S)5-IL-2Rα is set forth in SEQ ID NO:55; the sequence denoted as IL-2-(G3S)4-IL-2Rα is set forth in SEQ ID NO:56; the sequence denoted as IL-2-(G3S)3-IL-2Rα is set forth in SEQ ID NO: 57; and the extracellular domain of IL-2Rα is set forth in SEQ ID NO: 10. FIG. 2B provides the deduced protein sequences of non-limiting examples of human IL-2/IL-2Rα fusion proteins. The sequences of human IL-2 and IL-2Rα are shown above and below, respectively, of the fusion proteins. The sequence denoted as IL-2 is set forth in SEQ ID NO: 1; the sequence denoted as IL-2-(G3S)2-IL-2Rα is set forth in SEQ ID NO: 58; the sequence denoted as IL-2-(G3S)3-IL-2Rα is set forth in SEQ ID NO:59; the sequence denoted as IL-2-(G3S)4-IL-2Rα is set forth in SEQ ID NO:60; the sequence denoted as IL-2-(G4S)4-IL-2Rα is set forth in SEQ ID NO: 61; and the extracellular domain of IL-2Rα is set forth in SEQ ID NO: 7.

FIG. 3 shows the bioactivity of IL-2/IL-2Rα fusion proteins. COS-7 cells were transfected with the IL-2/IL-2Rα fusion cDNAs with the indicated linkers. Supernatants from these cells were cultured with anti-CD3 activated T cell blasts to assess IL-2 activity. (A) Proliferative responses by the T blasts after dilutions of the indicated fusion proteins. (B) Effect of anti-IL-2 on proliferation stimulated by a 1:2 dilution of the culture supernatant containing the indicated fusion proteins.

Figure 5:
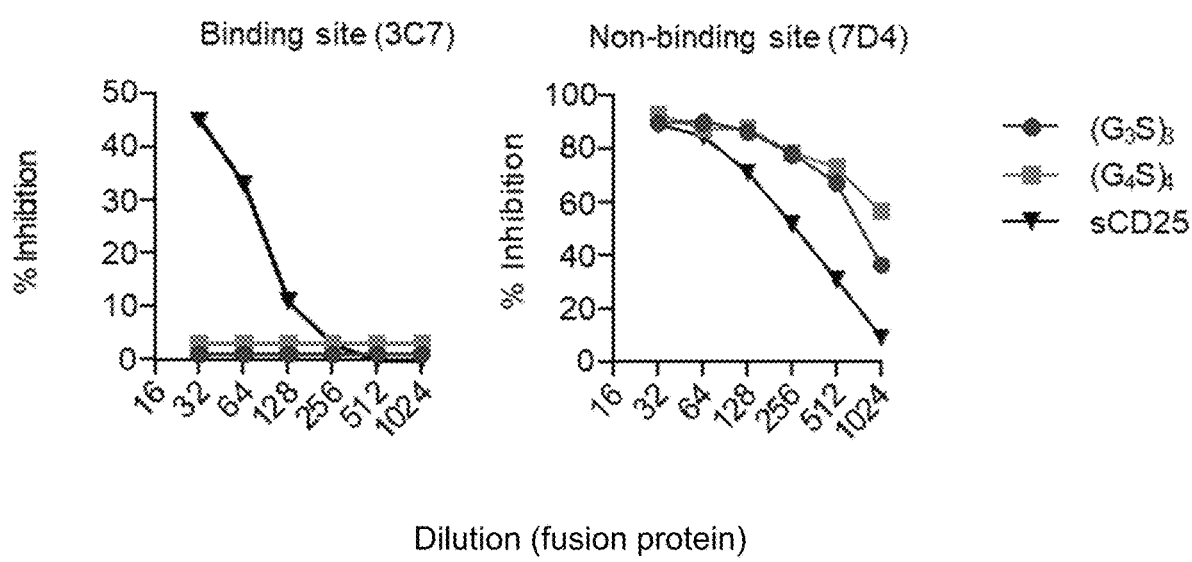

FIG. 5 shows that a monoclonal anti-IL-2Rα antibody that is directed to the IL-2 binding site of IL-2Rα cannot bind to the IL-2/IL-2Rα fusion protein. Purified fusion proteins with variable linkers, as indicated, were first incubated with the 3C7 anti-IL-2Rα monoclonal antibody, directed to the ligand binding site of IL-2Rα or the 7D4 monoclonal antibody, directed to a non-ligand binding site of IL-2Rα. The capacity of 3C7 or 7D4 to then bind to cell surface IL-2Rα was assessed using IL-2Rα-transfected EL4 cells.

Figure 6:
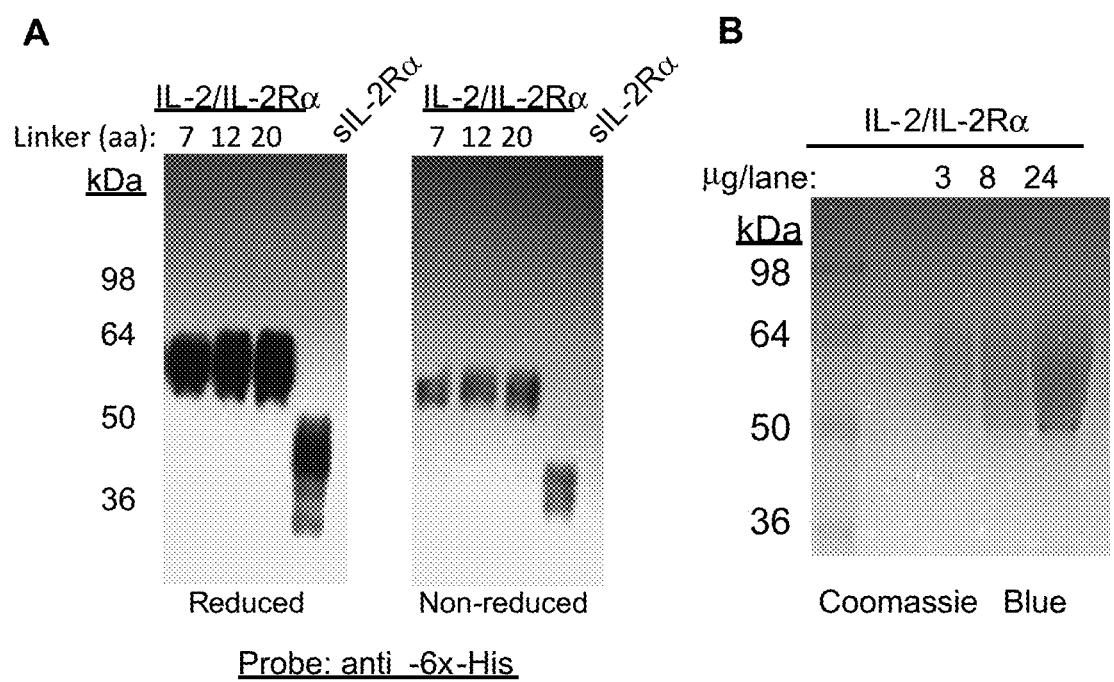

FIG. 6 shows the biochemical properties of purified IL-2/IL-2Rα. (A) Purified IL-2/IL-2Rα was subjected to SDS-PAGE under reducing and non-reducing conditions; IL-2/IL-2Rα was visualized by Western blot analysis by probing with an antibody directed to 6×-His tag of the fusion protein. (B) The indicated amount of purified IL-2/(Gly$_3$Ser)$_3$/IL-2Rα was subjected to SDS-PAGE under reducing conditions followed by Coomassie Blue staining.

Figure 7:
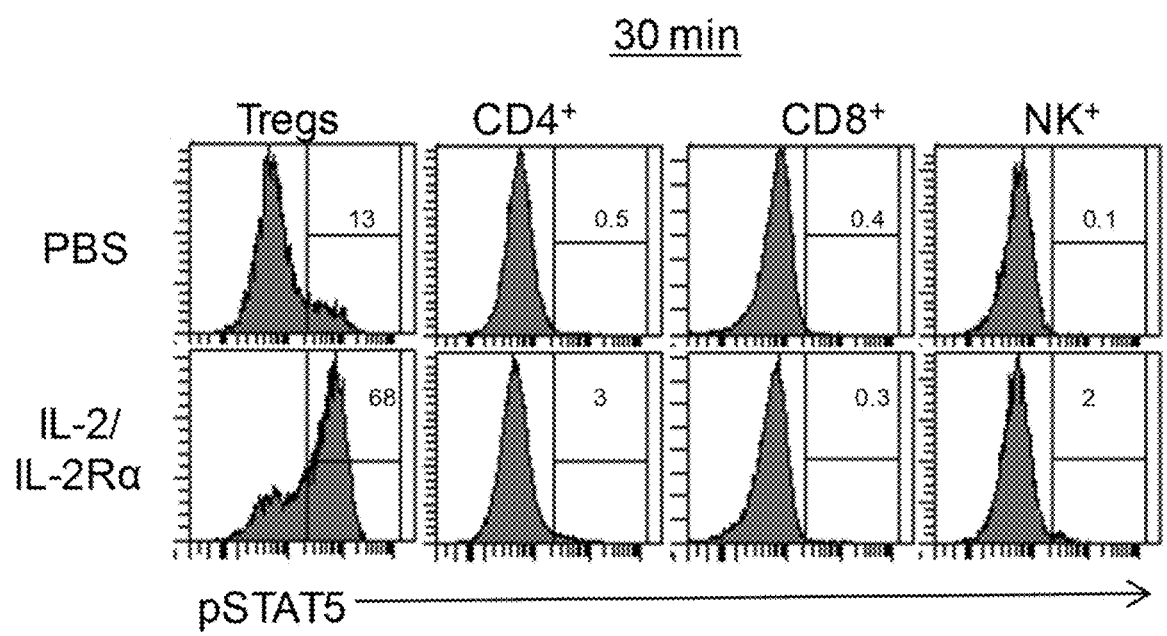
Figure 8:
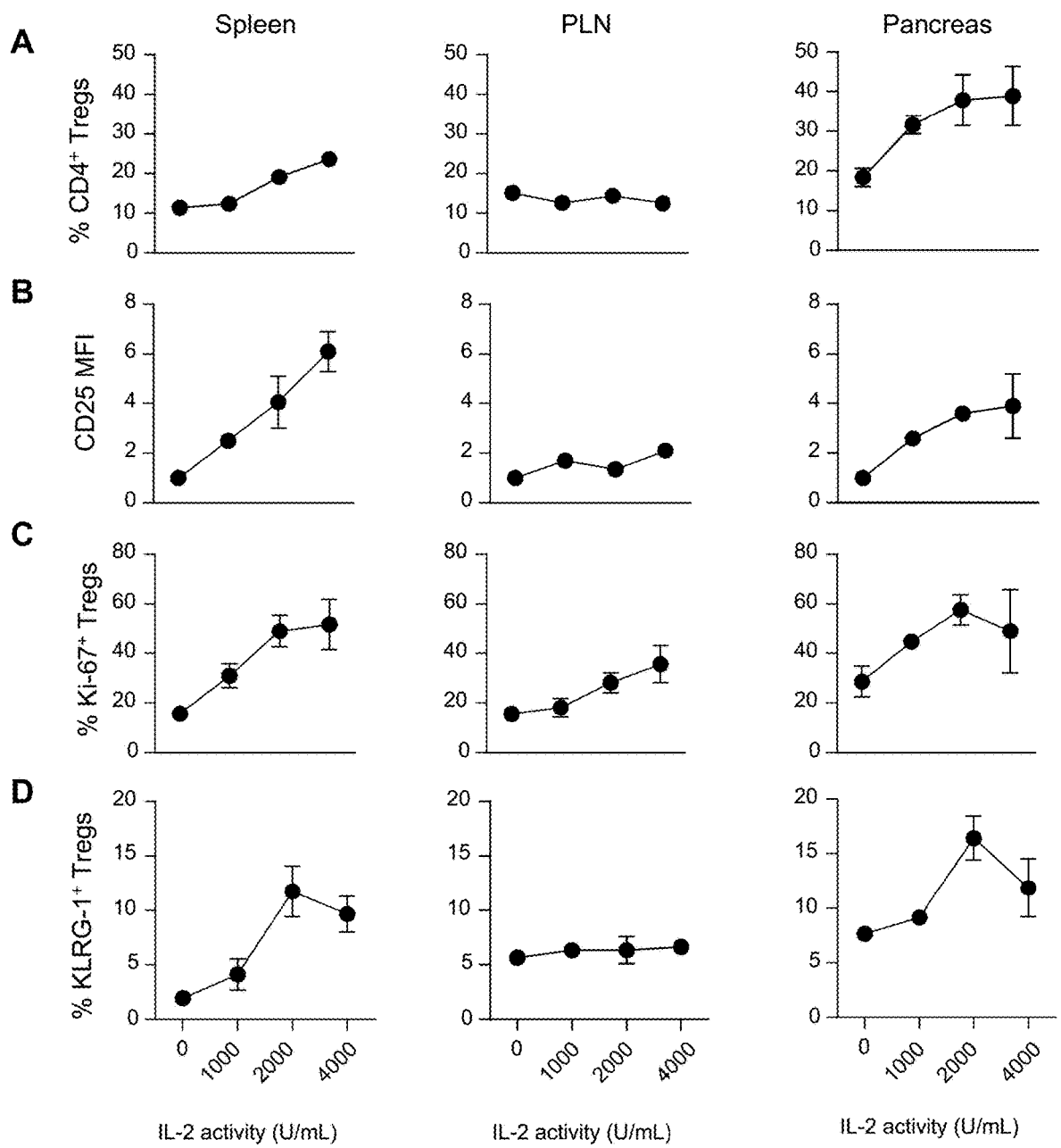

FIG. 7 shows the effect of IL-2/IL-2Rα fusion protein on IL-2-dependent signal transduction in vivo. C57BL/6 mice received a single injection i.p. of IL-2/(G$_3$S)$_3$/IL-2Rα (4000 units of IL-2 activity) and pSTAT5 levels in the indicated spleen cell populations were immediately assess. pSTAT5 levels were determined 0.5 hr after injection of the IL-2/IL-2Rα fusion protein. For CD4$^+$ T cells, the cells were gated to excluded Foxp3$^+$ Treg cells FIG. 8 shows the effect of IL-2/IL-2Rα fusion protein on Tregs cells in vivo. NOD mice were injected i.p. 3 times (day 1, 3, 5) with the indicated amount of IL-2 activity associated with IL-2/(G$_3$S)$_3$/IL-2Rα. The effect on Tregs was assessed for the spleen, pancreatic lymph nodes (PLN) and pancreas 24 hr after the last injection. Evaluated were the proportion of Tregs in CD4$^+$ T cells; the mean fluorescent intensity (MFI) for CD25 expression by Tregs after normalization to CD25 expression by Tregs from control treated mice; the proliferative status of Tregs as assessed by expression of the proliferative marker Ki67; and the % of Tregs that expressed Klrg1, which marks an IL-2-dependent terminally differentiated subpopulation.

Figure 9:
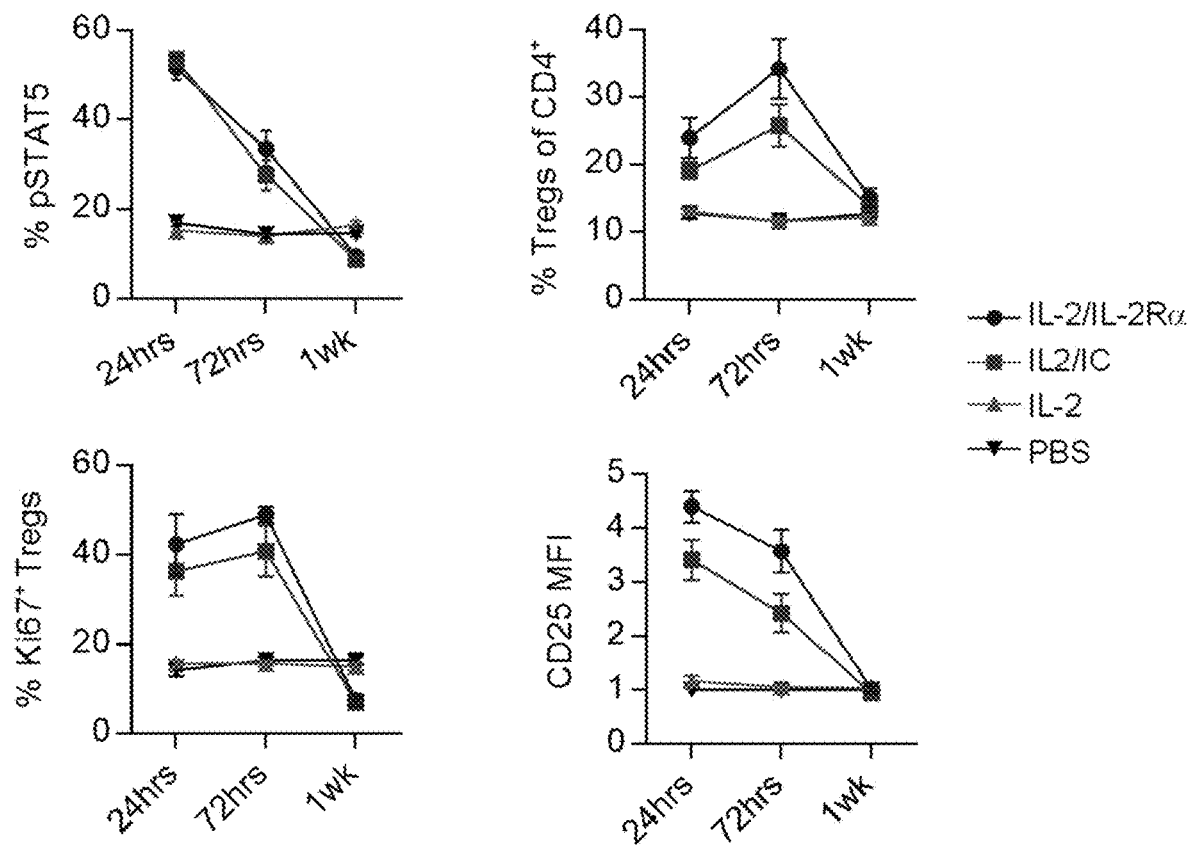

FIG. 9 shows the comparison of IL-2/IL-2Rα fusion protein and recombinant IL-2 to induce changes in Treg cells in vivo. C57BL/6 mice were injected i.p. 3 times (day 1, 3, 5) with IL-2/(G$_3$S)$_3$/IL-2Rα (2000 Units), recombinant human IL-2 (25,000 Units) or preformed complexes of anti-IL-2 (Jes-6.1; 5 μg) and mouse IL-2 (10,000 Units) (IL2/IC). The effect on Tregs was assessed for the spleen 24, 72 hr and 1 week after the last injection. Treg were evaluated as described in FIG. 8.

Figure 10:
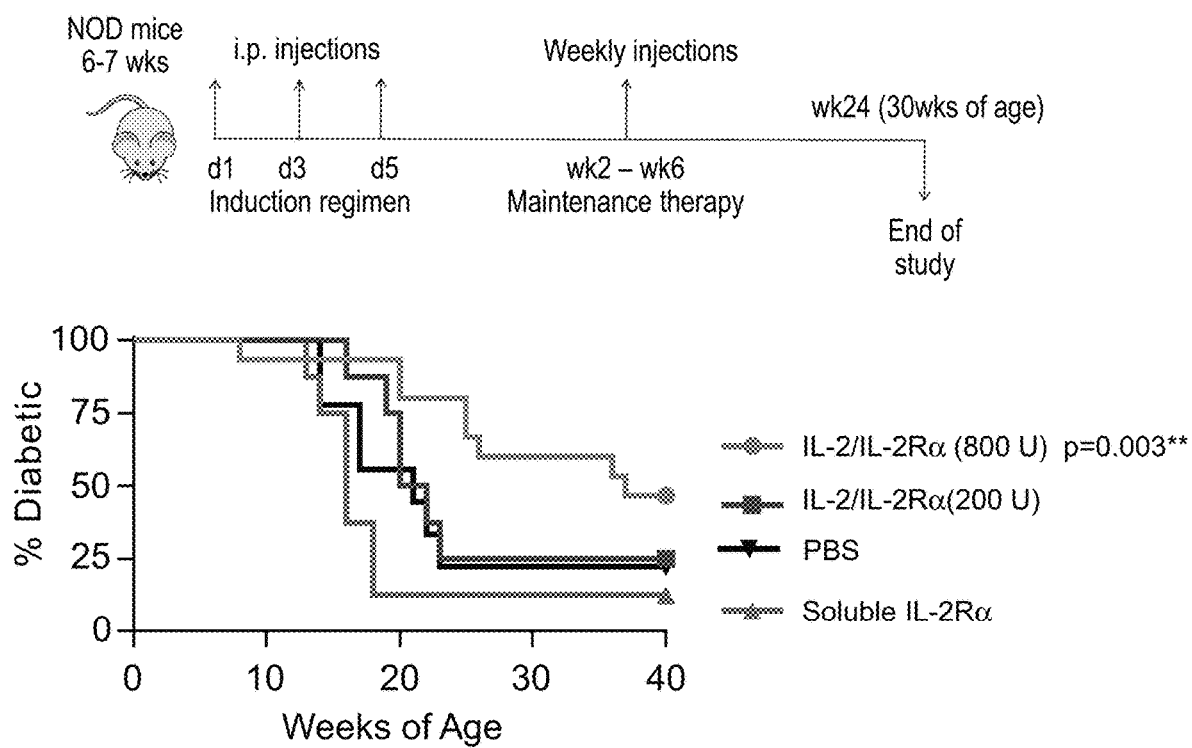

FIG. 10 shows Limited application of low-dose IL-2 delays diabetes in NOD mice. NOD mice (8 mice/group) received IL-2/IL-2Rα, soluble IL-2Rα, or PBS according to the schedule in (A). Urine and blood glucose levels were monitored until mice reached 40 weeks of age. Mice were considered diabetic after 2 consecutive readings of glucose levels >250 mg/dl.

Figure 11:
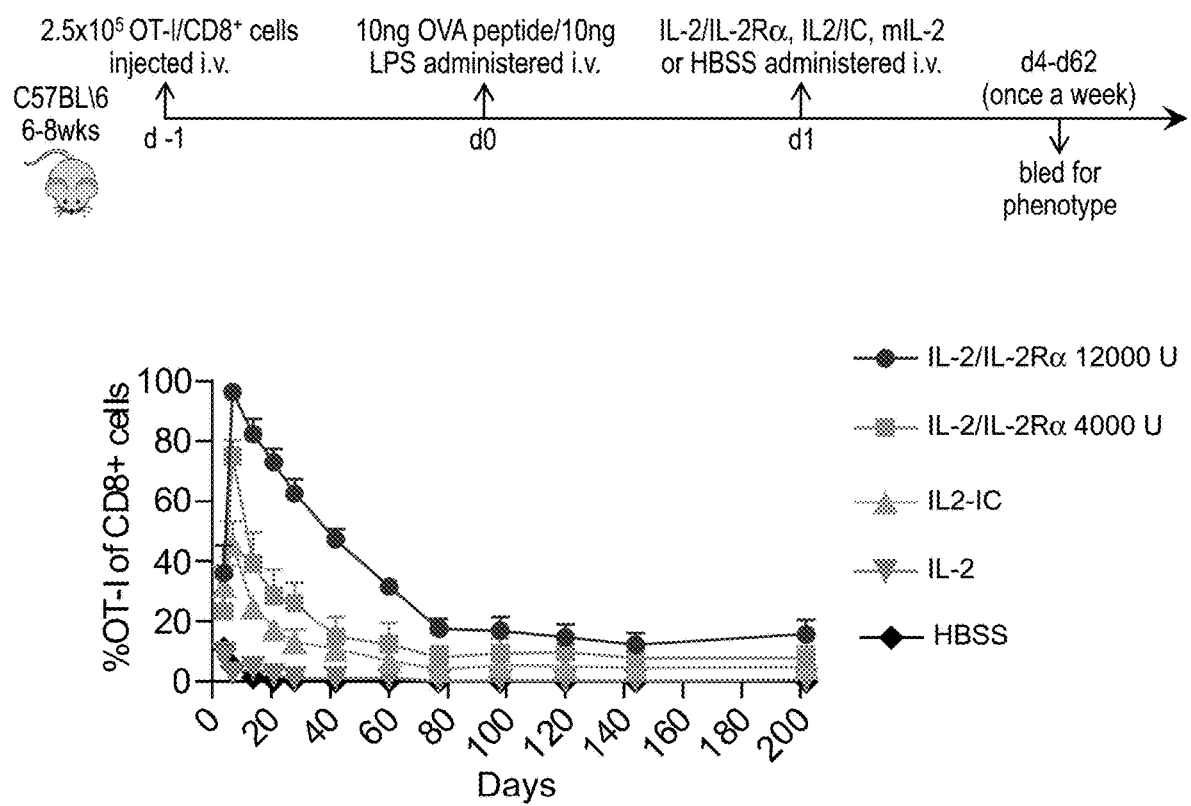

FIG. 11 demonstrates high-dose IL-2/IL-2Rα enhances the development of CD8$^+$ T cell memory. C57BL/6 mice received congenic class I-restricted ovalbumin (OVA)-specific OT-I T cell receptor transgenic T cells. These mice were immunized and treated with a single application of IL-2/(G$_3$S)$_3$/IL-2Rα fusion protein, IL2/IC containing 15,000 units of IL-2, or recombinant IL-2 (25,000 Units). At the indicated times, the relative proportion of OT-I T cells within the total CD8$^+$ T cell compartment in peripheral blood was assessed.

Figure 12:
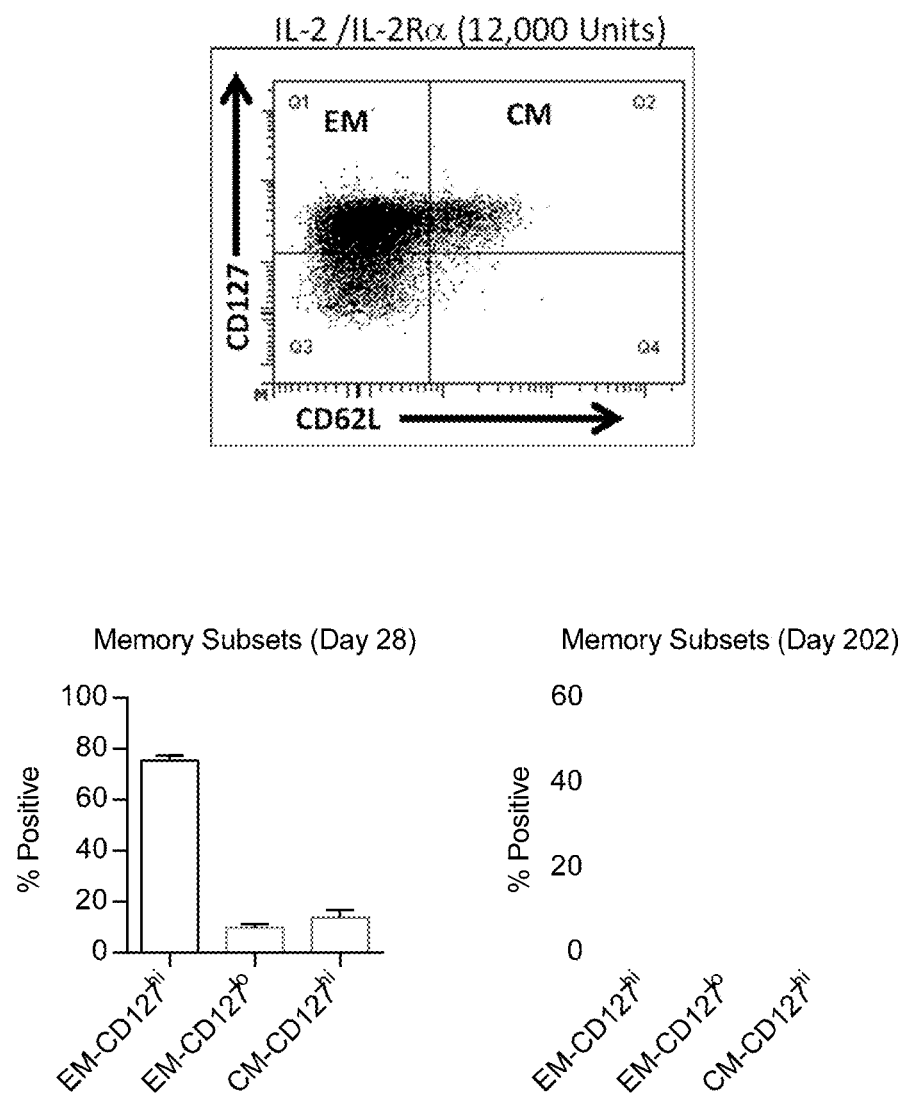

FIG. 12 shows the type of persistent OT-I memory cells supported by high-dose IL-2/IL-2Rα fusion protein: (A) Gating strategy to identify effector-memory (EM) and central memory (CM) cells. (B) Distribution of OT-1 memory cells 28 and 202 day post immunization for mice that also received IL-2/IL-2Rα (12,000 units).

FIG. 13 shows characterization of human IL-2/IL-2Rα fusion proteins containing glycine/serine linkers of variable length, as shown. (A) IL-2-bioactivity of purified human IL-2//IL-2Rα using the CTLL bioassay. (B) Western blot analysis of human IL-2/IL-2Rα fusion proteins after SDS-PAGE under reducing conditions.

Figure 14:
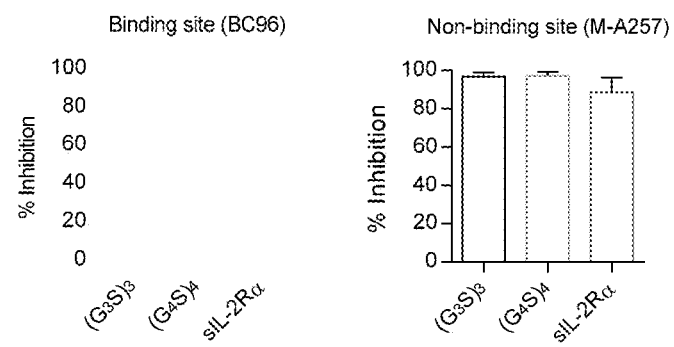

FIG. 14 shows human IL-2/IL-2Rα fusion protein bind monoclonal anti-IL-2Rα antibodies. Purified fusion proteins with the indicated linkers were first incubated with the BC96 anti-IL-2Rα monoclonal antibody, directed to the ligand binding region of human IL-2Rα or the M-A257 monoclonal antibody, directed to a non-ligand binding region of human IL-2Rα. The capacity of BC96 or M-A257 to then bind to cell surface IL-2Rα was assessed using IL-2Rα-transfected CHO cells.

Figure 15:

FIG. 15 shows IL-2 interacts with the IL-2 binding site of IL-2Rα in the context of human IL-2/IL-2Rα fusion proteins. IL-2-bioactivity of the indicated fusion proteins with variable glycine/serine linkers was assessed using CTLL cells. Mut refers to fusion proteins where IL-2Rα contained Arg$^{35}$→Thr, Arg$^{36}$→Ser mutations. Western blot analysis confirmed similar amounts of all fusion proteins (not shown).

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Overview

Current technology relies on the use of recombinant Interleukin-2 (IL-2), which has poor pharmacological properties, especially a short half-life that limits its usefulness. Provided herein are Interleukin-2/Interleukin-2 receptor alpha (IL-2/IL-2Rα) fusion proteins have intrinsic properties that separate them from recombinant IL-2 and other IL-2 fusion proteins. First, the size of the IL-2/IL-2Rα fusion protein will increase its half-life in vivo. Second, the weak interaction between IL-2 and IL-2Rα (one subunit of the IL-2R) in the context of the IL-2/IL-2Rα fusion protein provides another mechanism to prolong the availability of the IL-2. While not being limited to the specific mechanism of action, the prolonged availability of the IL-2 activity might occur through a competitive interaction between the IL-2 moiety with IL-2Rα of the IL-2/IL-2Rα fusion and with cells that express the IL-2R.

II. Interleukin-2/Interleukin-2 Receptor Alpha Fusion Proteins and Polynucleotides Encoding the Same A fusion protein is provided which comprises a first polypeptide comprising interleukin-2 (IL-2) or a functional variant or fragment thereof fused in frame to a second polypeptide comprising or consisting of the extracellular domain of the Interleukin-2 Receptor Alpha (IL-2Rα) polypeptide or a functional variant or fragment thereof.

As used herein, "fusion protein" refers to the in frame genetic linkage of at least two heterologous polypeptides. Upon transcription/translation, a single protein is made. In this way, multiple proteins, or fragments thereof can be incorporated into a single polypeptide. "Operably linked" is intended to mean a functional linkage between two or more elements. For example, an operable linkage between two polypeptides fuses both polypeptides together in frame to produce a single polypeptide fusion protein. In a particular aspect, the fusion protein further comprises a third polypeptide which, as discussed in further detail below, can comprise a linker sequence.

The IL-2/IL-2Rα fusion protein or the active variant or fragment thereof can have one or more the following properties/activities: (1) increasing activity of regulatory T cells (Tregs) and/or increasing immune tolerance in low dose IL-2 based therapies; (2) increasing immune response and memory in higher dose therapies; (3) increasing IL-2 availability when compared to recombinant IL-2; and/or (4) increasing persistent IL-2 stimulation of IL-2R bearing lymphocytes in vivo. Such activity and methods of assaying are disclosed in further detail elsewhere herein. See, for example, the Experimental Section provided herein.

In one non-limiting embodiment, an increased activity of Tregs that results from the IL-2/IL-2Rα fusion protein or the active variant or fragment thereof can be assayed in a variety of ways including, for example, (1) an increased representation and number of Tregs in the CD4$^+$ T cell compartment; (2) upregulation of IL-2-dependent CD25; (3) increased proliferation as assessed by expression of the proliferative marker Ki67; and (4) an increased fraction of IL-2-dependent terminally differentiated KIrg1$^+$ Treg subset. Such effects on Tregs can be seen in, for example, in the spleen and the inflamed pancreas.

In one non-limiting embodiment, the IL-2/IL-2Rα fusion protein or the active variant or fragment thereof increases tolerogenic and immune suppressive Tregs and immunity through increasing T effector/memory responses and, in further embodiments, it exhibits improved pharmacokinetics by delivering such responses at (1) lower effective levels of IL-2 activity compared to native or recombinant IL-2; (2) displays more persistent biological responses than native or recombinant IL-2; and/or (3) retains the hierarchy with Tregs responsive at lower level doses that T effector/memory cells.

In specific embodiments, the fusion protein has an improved activity over the native or recombinant IL-2. For example, the effect of the IL-2/IL-2Rα fusion protein can increase tolerogenic Tregs at about 2 fold, 5 fold, 10 fold, 20 fold, 30 fold, 40 fold, 50 fold, 60 fold, 70 fold, 80 fold, 90 fold, 100 fold 150 fold, 200 fold or lower level IL-2 activity in comparison to native or recombinant IL-2. In other embodiments, the IL-2/IL-2Rα fusion protein is more effective than native or recombinant IL-2 in inducing persistent augmentation of Tregs and related properties.

Various IL-2 and IL-2Rα fragments and variants from a variety of organism can be used to generate the IL-2/IL-2Rα extracellular domain fusion proteins provided herein. Such components are discussed in further detailed elsewhere herein. Examples of non-limiting unprocessed IL-2/IL-2Rα extracellular domain fusion proteins are set forth in SEQ ID NO: 17, 19, 21, 23, 25, 27, 36, 38, 44, 46, 54, 55, 56, 57, 58, 59, 60, and 61, while non-limiting examples of mature forms of the IL-2/IL-Ra extracellular domain fusion proteins are set forth in SEQ ID NOS: 16, 18, 20, 22, 24, 26, 37, 39, 43, 45, 62 and 64. Non-limiting examples of polynucleotides encoding such fusion proteins are set forth in SEQ ID NO: 29, 30, 31, 32, 33, 34, 42, 47, 48, 49, 63, and 65.

The term "secretory signal sequence" denotes a polynucleotide sequence that encodes a polypeptide (a "secretory peptide") that, as a component of a larger polypeptide, directs the larger polypeptide through a secretory pathway of the cell in which it is synthesized. The larger polypeptide is commonly cleaved to remove the secretory peptide during the transit through the secretory pathway. As used herein, a "mature" form of a fusion protein or polypeptide comprises the processed form of the polypeptide that has had the secretory peptide removed. As used herein, the "unprocessed" form of the fusion protein retains the secretory peptide sequence.

Biologically active fragments and variants of the mature and unprocessed form of the IL-2/IL-Rα extracellular domain fusion proteins, and the polynucleotide encoding the same, are also provided. Such a functional polypeptide fragment can comprise at least 5, 6, 7, 8, 9, 10, 11, 12, 13, 14, 15, 16, 17, 18, 19, 20, 30, 40, 50, 75, 100, 150, 200, 250, 300, 350, 400, 450, 500 or more continuous amino acids of any one of SEQ ID NO: 16, 17, 18, 19, 20, 21, 22, 23, 24, 25, 26, 27, 36, 37, 38, 39, 43, 44, 45, 46, 54, 55, 56, 57, 58, 59, 60, 61, 62, or 64. Alternatively, a functional polypeptide variant can comprise at least 75%, 80%, 85%, 90%, 91%, 92%, 93%, 94%, 95%, 96%, 97%, 98%, or 99% sequence identity to the sequence set forth in SEQ ID NO: 16, 17, 18, 19, 20, 21, 22, 23, 24, 25, 26, 27, 36, 37, 38, 39, 43, 44, 45, 46, 54, 55, 56, 57, 58, 59, 60, 61, 62, or 64.

Active variants and fragments of polynucleotides encoding the IL-2/IL-Rα extracellular domain fusion proteins are further provided. Such polynucleotide can comprise at least 100, 200, 300, 400, 500, 600, 700, 800, 1000, 1100, 1200, 1300, 1500, 1800, 2000 continuous nucleotides of SEQ ID NO: 29, 30, 31, 32, 33, 34, 42, 47, 48, 49, 63 or 65 or the polynucleotide encoding the polypeptides set forth in SEQ ID NO: 16, 17, 18, 19, 20, 21, 22, 23, 24, 25, 26, 27, 36, 37, 38, 39, 43, 44, 45, 46, 54, 55, 56, 57, 58, 59, 60, 61, 62, or 64 and continue to encode a functional IL-2/IL-Rα extracellular domain fusion protein. Alternatively, a functional polynucleotide can comprise at least 75%, 80%, 85%, 90%, 91%, 92%, 93%, 94%, 95%, 96%, 97%, 98%, or 99% sequence identity to the sequence set forth in SEQ ID NO: 29, 30, 31, 32, 33, 34, 42, 47, 48, 49, 63 or 65 or the polynucleotide encoding the polypeptides set forth in SEQ ID NO: 16, 17, 18, 19, 20, 21, 22, 23, 24, 25, 26, 27, 36, 37, 38, 39, 43, 44, 45, 46, 54, 55, 56, 57, 58, 59, 60, 61, 62, or 64 and continue to encode a functional IL-2/IL-Rα extracellular domain fusion proteins.

It is further recognized that the components of the IL-2/IL-2Rα fusion protein can be found any order. In one embodiment, the IL-2 polypeptide is at the N-terminus and the extracellular domain of IL-2Rα is at the C-terminus of the fusion protein.

i. Interleukin-2

As used herein, "Interleukin-2" or "IL-2" refers to any native or recombinant IL-2 from any vertebrate source, including mammals such as primates (e.g. humans) and rodents (e.g. mice and rats), and domesticated or agricultural mammals unless otherwise indicated. The term encompasses unprocessed IL-2, as well as, any form of IL-2 that results from processing in the cell (i.e, the mature form of IL-2). The term also encompasses naturally occurring variants and fragments of IL-2, e.g. splice variants or allelic variants, and non-naturally occurring variants. The amino acid sequence of an exemplary mature form of human IL-2 (having the 20 amino acid signal sequence) is shown in SEQ ID NO: 2. Unprocessed human IL-2 additionally comprises an N-terminal 20 amino acid signal peptide (SEQ ID NO: 1), which is absent in the mature IL-2 molecule. The amino acid sequence of an exemplary mature form of mouse IL-2 (having the 20 amino acid signal sequence) is shown in SEQ ID NO: 4. Unprocessed mouse IL-2 additionally comprises an N-terminal 20 amino acid signal peptide (SEQ ID NO: 3), which is absent in the mature IL-2 molecule. See also FIG. 2A and FIG. 2B. By a "native IL-2", also termed "wild-type IL-2", is meant a naturally occurring or recombinant IL-2.

Additional nucleic acid and amino acid sequences for IL-2 are known. See, for example, GenBank Accession Nos: Q7JFM2 (*Aotus lemurinus* (Gray-bellied night monkey)); Q7JFM5 (*Aotus nancymaae* (Ma's night monkey)); P05016 (*Bos taurus* (Bovine)); Q29416 (*Canis familiaris* (Dog) (*Canis lupus familiaris*)); P36835 (*Capra hircus* (Goat)); and, P37997 (*Equus caballus* (Horse)).

Biologically active fragments and variants of IL-2 are also provided. Such IL-2 active variants or fragments will retain IL-2 activity. The phrase "biological activity of IL-2" refers to one or more of the biological activities of IL-2, including but not limited to, the ability to stimulate IL-2 receptor bearing lymphocytes. Such activity can be measured both in vitro and in vivo. IL-2 is a global regulator of immune activity and the effects seen here are the sum of such activities. For example, it is regulates survival activity (Bcl-2), induces T effector activity (IFN-gamma, Granzyme B, and Perforin), and promotes T regulatory activity (FoxP3). See, for example, Malek et al. (2010) Immunity 33(2):153-65, herein incorporated by reference in its entirety.

Biologically active variants of IL-2 are known. See, for example, US Application Publications 20060269515 and 20060160187 and WO 99/60128, each of which is herein incorporated by reference.

Biologically active fragments and variants of IL-2 can be employed in the fusion proteins disclosed herein. Such a functional fragment can comprise at least 10, 11, 12, 13, 14, 15, 16, 17, 18, 19, 20, 30, 40, 50, 75, 100, 125, 150 or more continuous amino acids of SEQ ID NO: 1, 2, 3, or 4. Alternatively, a functional variant can comprise at least 75%, 80%, 85%, 90%, 91%, 92%, 93%, 94%, 95%, 96%, 97%, 98%, or 99% sequence identity to the sequence set forth in SEQ ID NO: 1, 2, 3, or 4.

Active variants and fragments of polynucleotides encoding the IL-2 proteins are further provided. Such polynucleotide can comprise at least 100, 200, 300, 400, 500, 600, 700 continuous nucleotides of polypeptide encoding SEQ ID NO: 1, 2, 3, or 4, and continue to encode a protein having IL-2 activity. Alternatively, a functional polynucleotide can comprise at least 75%, 80%, 85%, 90%, 91%, 92%, 93%, 94%, 95%, 96%, 97%, 98%, or 99% sequence identity to the polypeptide encoding the amino sequence set forth in SEQ ID NO: 1, 2, 3, or 4 and continue to encode a functional IL-2 polypeptide.

ii. Interleukin-2 Receptor Alpha

The term "CD25" or "IL-2 receptor α" or "IL-2Rα" as used herein, refers to any native or recombinant IL-2Rα from any vertebrate source, including mammals such as primates (e.g. humans) and rodents (e.g., mice and rats) and domesticated or agricultural mammals unless otherwise indicated. The term also encompasses naturally occurring variants of IL-2Rα, e.g. splice variants or allelic variants, or non-naturally occurring variants. Human IL-2 exerts its biological effects via signaling through its receptor system, IL-2R. IL-2 and its receptor (IL-2R) are required for T-cell proliferation and other fundamental functions which are crucial of the immune response. IL-2R consists of 3 non-covalently linked type I transmembrane proteins which are the alpha (p55), beta (p75), and gamma (p65) chains. The human IL-2R alpha chain contains an extracellular domain of 219 amino acids, a transmembrane domain of 19 amino acids, and an intracellular domain of 13 amino acids. The secreted extracellular domain of IL-2R alpha (IL-2R-a) can be employed in the fusion proteins describe herein.

The amino acid sequence of an exemplary mature form of human IL-2Rα is shown in SEQ ID NO: 6. Unprocessed human IL-2Rα is shown in SEQ ID NO: 5. The extracellular domain of SEQ ID NO: 6 is set forth in SEQ ID NO: 7. The amino acid sequence of an exemplary mature form of mouse IL-2Rα is shown in SEQ ID NO: 9. Unprocessed mouse IL-2Rα is shown in SEQ ID NO: 8. The extracellular domain of SEQ ID NO: 9 is set forth in SEQ ID NO: 10. By a "native IL-2Rα", also termed "wild-type IL-2Rα", is meant a naturally occurring or recombinant IL-2Rα. The sequence of a native human IL-2Rα molecule is shown in SEQ ID NO: 5 and 6.

Nucleic acid and amino acid sequences for IL-2Rα are known. See, for example, GenBank Accession Nos: NP_001030597.1 (*P. troglodytes*); NP_001028089.1 (*M. mulatta*); NM_001003211.1 (*C. lupus*); NP_776783.1 (*B. taurus*); NP_032393.3 (*M. musculus*); and, NP_037295.1 (*R. norvegicus*), each of which is herein incorporated by reference.

Biologically active fragments and variants of the extracellular domain of IL-2Rα are also provided. Such IL-2Rα extracellular domain active variants or fragments will retain the IL-2Rα extracellular domain activity. The phrase "biological activity of the IL-2Rα extracellular domain" refers to one or more of the biological activities of extracellular domain of IL-2Rα, including but not limited to, the ability to enhance intracellular signaling in IL-2 receptor responsive cells. Non-limiting examples of biologically active fragments and variants of the IL-2Rα are disclosed, for example, in Robb et al., *Proc. Natl. Acad. Sci. USA*, 85:5654-5658, 1988, which is herein incorporated by reference.

Biologically active fragments and variants of the extracellular domain of IL-2Rα can be employed in the fusion proteins disclosed herein. Such a functional fragment can comprise at least 10, 11, 12, 13, 14, 15, 16, 17, 18, 19, 20, 30, 40, 50, 75, 100, 125, 150, 175, 200, 215 or greater continuous amino acids of the extracellular domain of any one of SEQ ID NO: 6, 9, 7, 10, 5, or 8. Alternatively, a functional variant can comprise at least 75%, 80%, 85%, 90%, 91%, 92%, 93%, 94%, 95%, 96%, 97%, 98%, or 99% sequence identity to the sequence set forth in SEQ ID NO: 6, 9, 7, 10, 5, or 8.

In one embodiment, the fusion proteins provided herein can comprise at least one mutation within the extracellular domain of IL-2Rα. In a specific embodiment, the Arginine at position 35 of IL-2Rα can be mutated to a Threonine and/or the Arginine at position 36 of IL-2Rα can be mutated to a Serine. Such a fusion protein can have increased IL-2 activity compared to a fusion protein not comprising these mutations in the extracellular domain of IL-2Rα and/or compared to native or recombinant IL-2. The amino acid sequences of exemplary fusion proteins comprising IL-2Rα with mutations within the extracellular domain of IL-2Rα are set forth in SEQ ID NOS: 62 and 64. In one embodiment, the fusion protein comprises the amino acid sequence of any one of SEQ ID NO: 62 or 64; or a sequence having at least 80%, 85%, 90%, or 95% to any one of SEQ ID NO: 62 or 64.

Active variants and fragments of polynucleotides encoding the extracellular domain of IL-2Rα are further provided. Such polynucleotide can comprise at least 100, 200, 300, 400, 500, 600 or greater continuous nucleotides of polypeptide encoding SEQ ID NO: 6, 9, 7, 10, 5, or 8 and continue to encode a protein having the extracellular domain activity of IL-2Rα. Alternatively, a functional polynucleotide can comprise at least 80%, 85%, 90%, 91%, 92%, 93%, 94%, 95%, 96%, 97%, 98%, or 99% sequence identity to the polypeptide encoding the amino sequence set forth in SEQ ID NO: 6, 9, 7, 10, 5, or 8 and continue to encode a protein having the extracellular domain activity of IL-2Rα.

iii. Additional Components

The IL-2/IL-2Rα fusion proteins can further comprise additional elements. Such elements can aid in the expression of the fusion protein, aid in the secretion of the fusion protein, improve the stability of the fusion protein, allow for more efficient purification of the protein, and/or modulate the activity of the fusion protein.

"Heterologous" in reference to a polypeptide or polynucleotide is a polypeptide or polynucleotide that originates from a different protein or polynucleotide. The additional components of the fusion protein can originate from the same organism as the other polypeptide components of the fusion protein, or the additional components can be from a different organism than the other polypeptide components of the fusion protein.

In one embodiment, the IL-2/IL-2Rα fusion protein comprises a linker sequence located between the IL-2 polypeptide and the IL-2Rα polypeptide. The linker can be of any length and can comprise at least 1, 2, 3, 4, 5, 6, 7, 8, 9, 10, 11, 12, 13, 14, 15, 16, 17, 18, 19, 20, 25, 30, 31, 32, 33, 34, 35, 36, 37, 38, 39, 40, 50 or 60 or more amino acids. In one embodiment, the linker sequence comprises glycine amino acid residues. In other instances, the linker sequence comprises a combination of glycine and serine amino acid residues. Such glycine/serine linkers can comprises any combination of the amino acid residues, including, but not limited to, the peptide GGGS or GGGGS or repeats of the same, including 1, 2, 3, 4, 5, 6, 7, 8, 9, 10 or more repeats of these given peptides. For example, linker sequences can comprise GGGSGGGSGGGS (SEQ ID NO: 13) (also noted as (Gly$_3$Ser)$_3$); GGGSGGGSGGGSGGGS (SEQ ID NO: 11) (also noted as (Gly$_3$Ser)$_4$); or (Gly$_3$Ser)$_5$; (Gly$_3$Ser)$_6$; (Gly$_3$Ser)$_7$, etc. Linker sequences can further comprise (Gly$_4$Ser)$_3$ as set forth in SEQ ID NO: 50; GGGGSGGGGSGGGGSGGGGS (SEQ ID NO: 40) (also noted as (Gly$_4$Ser)$_4$); GGGGSGGGGSGGGGSGGGGSGGGGS (SEQ ID NO: 41) (also noted as (Gly$_4$Ser)$_5$); (Gly$_4$Ser)$_2$, (Gly$_4$Ser)$_1$, (Gly$_4$Ser)$_6$; (Gly$_4$Ser)$_7$; (Gly$_4$Ser)$_8$, etc. In addition, active variants and fragments of any linker can further be employed in the fusion protein disclosed herein.

It is further recognized that the polynucleotide encoding the IL-2/IL-2Rα fusion protein can comprise additional elements that aid in the translation of the fusion protein. Such sequences include, for example, Kozak sequences attached to the 5' end of the polynucleotide encoding the fusion protein. The Kozak consensus sequence is a sequence which occurs on eukaryotic mRNA that plays a role in the initiation of the translation process and has the consensus (gcc)gccRccAUGG (SEQ ID NO: 3S); wherein (1) a lower case letter denotes the most common base at a position where the base can nevertheless vary; (2) upper case letters indicate highly-conserved bases, i.e. the 'AUGG' sequence is constant or rarely, if ever, changes, with the exception being the IUPAC ambiguity code 'R' which indicates that a purine (adenine or guanine) is normally observed at this position; and (3) the sequence in brackets ((gcc)) is of uncertain significance. In one embodiment, the Kozak sequence comprises the sequence set forth in SEQ ID NO: 53.

In one non-limiting embodiment, the IL-2/IL-2Rα fusion protein comprises an IL-2 leader optimized Kozak sequence as set forth in SEQ ID NO: 28 or a functional variant or fragment thereof. A functional variant or fragment of a Kozak sequence will retain the ability to increase translation of the protein when compared to the level of translation from a sequence lacking the leader. Such a functional fragment can comprise at least 5, 6, 7, 8, 9, 10, 11, 12, 13, 14, 15, 16, 17, 18, 19, 20, 30, 40 continuous nucleotides of a kozak sequence or the sequence set forth in SEQ ID NO: 28 or 53. Alternatively, a functional variant can comprise at least 80%, 85%, 90%, 91%, 92%, 93%, 94%, 95%, 96%, 97%, 98%, or 99% sequence identity to the kozak sequence or the sequence set forth in SEQ ID NO: 28 or 53.

In still further embodiments, the IL-2/IL-2Rα fusion protein comprises one or more tags at the C-terminus to aid in the purification of the polypeptide. Such tags are known and include, for example, a Histidine tag. In specific embodiments a 6×His tag is employed. It is further recognized that an additional linker sequence can be employed between the fusion protein and the His tag.

Figure 1:
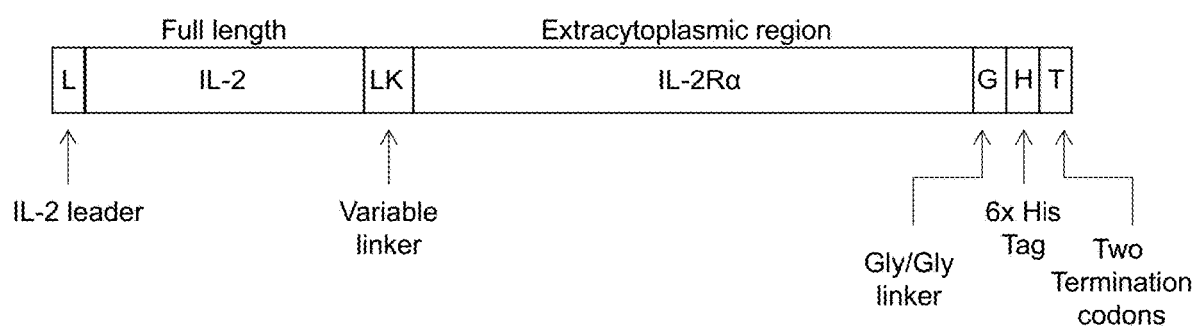
FIG. 1 provides a schematic of an IL-2/IL-2Rα fusion protein, where L=leader peptide, LK=linker region, G=glycine, H=histidine, and T=termination codon.

Non-limiting embodiment of an IL-2/IL-2Rα fusion protein is set forth in FIG. 1, FIG. 2A, and FIG. 2B. Such a fusion protein comprises a leader peptide, IL-2 or a functional variant or fragment thereof, a variable linker, IL-2Rα, a glycine linker, 6×his tag, and two termination codons.

iv. Variants and Fragments a. Polynucleotides

Fragments and variants of the polynucleotides encoding the IL-2/IL-2Rα extracellular domain fusion protein or the various components contained therein (i.e., the IL-2Rα extracellular domain, the IL-2Rα polypeptides, the linker sequences and/or Kozak sequences) can be employed in the various methods and compositions of the invention. By "fragment" is intended a portion of the polynucleotide and hence the protein encoded thereby or a portion of the polypeptide. Fragments of a polynucleotide may encode protein fragments that retain the biological activity of the native protein and hence have IL-2 activity, IL-2Rα extracellular domain activity, IL-2/IL-2Rα fusion protein activity, or if encoding a linker sequence, provide for the desired activity of the IL-2/IL-2Rα fusion protein.

A biologically active portion of a IL-2Rα extracellular domain, IL-2 polypeptide, IL-2/IL-2Rα fusion protein, Kozak sequence, or linker sequence can be prepared by isolating a portion of one of the polynucleotides encoding the portion of the IL-2Rα extracellular domain or IL-2 polypeptide and expressing the encoded portion of the polypeptide (e.g., by recombinant expression in vitro), and assessing the activity of the portion of the IL-2Rα extracellular domain or/and IL-2 polypeptide or the activity of the IL-2/ILRα fusion protein.

"Variant" sequences have a high degree of sequence similarity. For polynucleotides, conservative variants include those sequences that, because of the degeneracy of the genetic code, encode the amino acid sequence of one of the IL-2Rα extracellular domain polypeptides, IL-2 polypeptides, IL-2/IL-2Rα fusion proteins, or linker sequences. Variants such as these can be identified with the use of well-known molecular biology techniques, as, for example, polymerase chain reaction (PCR) and hybridization techniques. Variant polynucleotides also include synthetically derived nucleotide sequences, such as those generated, for example, by using site-directed mutagenesis but which still encode an IL-2Rα extracellular domain, IL-2 polypeptide, IL-2/IL-2Rα fusion protein, a Kozak sequence, or the linker sequence.

b. Polypeptides

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins are biologically active, that is they continue to possess the desired biological activity, that is, IL-2/IL-2Rα fusion protein activity, IL-2 activity or IL-2Rα extracellular domain activity. Such variants may result from, for example, genetic polymorphism or from human manipulation. Biologically active variants of a IL-2/IL-2Rα fusion protein or any one of its components (i.e., an IL-2Rα extracellular domain polypeptide, a IL-2 polypeptide, or a linker sequence) will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein may differ from that protein by as few as 1-15 amino acid residues, as few as 1-10, such as 6-10, as few as 5, as few as 4, 3, 2, or even 1 amino acid residue.

Proteins may be altered in various ways including amino acid substitutions, deletions, truncations, and insertions. Methods for such manipulations are generally known in the art. For example, amino acid sequence variants of the IL-2Rα extracellular domain, IL-2 polypeptide, IL-2/IL-2Rα fusion protein, or linker sequences can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferable.

Thus, the polynucleotides disclosed herein can include the naturally occurring sequences, the "native" sequences, as well as mutant forms. Likewise, the proteins used in the methods of the invention encompass naturally occurring proteins as well as variations and modified forms thereof. Such variants will continue to possess the ability to implement a recombination event. Generally, the mutations made in the polynucleotide encoding the variant polypeptide should not place the sequence out of reading frame, and/or create complementary regions that could produce secondary mRNA structure. See, EP Patent Application Publication No. 75,444.

Variant polynucleotides and proteins also encompass sequences and proteins derived from a mutagenic and recombinogenic procedure such as DNA shuffling. With such a procedure, one or more different IL-2Rα extracellular domain or IL-2 coding sequences can be manipulated to create a new IL-2Rα extracellular domain or IL-2 polypeptides possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

III. Polynucleotides Encoding the IL-2/IL-2Rα Fusion Proteins and Methods of Making Compositions further include isolated polynucleotides that encode the various fusion proteins described herein above, and variants and fragments thereof. Vectors and expression cassettes comprising the polynucleotides described herein are further disclosed. Expression cassettes will generally include a promoter operably linked to a polynucleotide and a transcriptional and translational termination region.

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues.

An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Conventional molecular biology, microbiology, and recombinant DNA techniques within the skill of the art may be employed herein. Such techniques are explained fully in the literature. See, e.g., Sambrook et al., "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (198S)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

A vector which comprises the above-described polynucleotides operably linked to a promoter is also provided herein. A nucleotide sequence is "operably linked" to an expression control sequence (e.g., a promoter) when the expression control sequence controls and regulates the transcription and translation of that sequence. The term "operably linked" when referring to a nucleotide sequence includes having an appropriate start signal (e.g., ATG) in front of the nucleotide sequence to be expressed and maintaining the correct reading frame to permit expression of the sequence under the control of the expression control sequence and production of the desired product encoded by the sequence. If a gene that one desires to insert into a recombinant nucleic acid molecule does not contain an appropriate start signal, such a start signal can be inserted in front of the gene. A "vector" is a replicon, such as plasmid, phage or cosmid, to which another nucleic acid segment may be attached so as to bring about the replication of the attached segment. The promoter may be, or is identical to, a bacterial, yeast, insect or mammalian promoter. Further, the vector may be a plasmid, cosmid, yeast artificial chromosome (YAC), bacteriophage or eukaryotic viral DNA.

Other numerous vector backbones known in the art as useful for expressing protein may be employed. Such vectors include, but are not limited to: adenovirus, simian virus 40 (SV40), cytomegalovirus (CMV), mouse mammary tumor virus (MMTV), Moloney murine leukemia virus, DNA delivery systems, i.e. liposomes, and expression plasmid delivery systems. Further, one class of vectors comprises DNA elements derived from viruses such as bovine papilloma virus, polyoma virus, baculovirus, retroviruses or Semliki Forest virus. Such vectors may be obtained commercially or assembled from the sequences described by methods well-known in the art.

A host vector system for the production of a polypeptide which comprises the vector of a suitable host cell is provided herein. Suitable host cells include, but are not limited to, prokaryotic or eukaryotic cells, e.g. bacterial cells (including gram positive cells), yeast cells, fungal cells, insect cells, and animal cells. Numerous mammalian cells may be used as hosts, including, but not limited to, the mouse fibroblast cell NIH 3T3, CHO cells, HeLa cells, Ltk⁻ cells, etc. Additional animal cells, such as R1.1, B-W and L-M cells, African Green Monkey kidney cells (e.g., COS 1, COS 7, BSC1, BSC40, and BMT10), insect cells (e.g., Sf9), and human cells and plant cells in tissue culture can also be used.

A wide variety of host/expression vector combinations may be employed in expressing the polynucleotide sequences presented herein. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMB9 and their derivatives, plasmids such as RP4; phage DNAS, e.g., the numerous derivatives of phage $\lambda$, e.g., NM989, and other phage DNA, e.g., M13 and filamentous single stranded phage DNA; yeast plasmids such as the 2$\mu$ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences (sequences that control the expression of a nucleotide sequence operably linked to it) may be used in these vectors to express the polynucleotide sequences provided herein. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage $\lambda$, the control regions of fd coat protein, the promoter for 3-phosphoglycerate kinase or other glycolytic enzymes, the promoters of acid phosphatase (e.g., Pho5), the promoters of the yeast $\alpha$-mating factors, and other sequences known to control the expression of genes of prokaryotic or eukaryotic cells or their viruses, and various combinations thereof.

It will be understood that not all vectors, expression control sequences and hosts will function equally well to express the polynucleotide sequences provided herein. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular nucleotide sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the nucleotide sequences to be expressed, and the ease of purification of the expression products.

In preparing the expression cassette, the various polynucleotides may be manipulated, so as to provide for the polynucleotide sequences in the proper orientation and, as appropriate, in the proper reading frame. Toward this end, adapters or linkers may be employed to join the polynucleotides or other manipulations may be involved to provide for convenient restriction sites, removal of superfluous DNA, removal of restriction sites, or the like. For example, linkers such as two glycines may be added between polypeptides. Methionine residues encoded by atg nucleotide sequences may be added to allow initiation of gene transcription. For this purpose, in vitro mutagenesis, primer repair, restriction, annealing, resubstitutions, e.g., transitions and transversions, may be involved.

Further provided is a method of producing a polypeptide which comprises expressing a polynucleotide encoding a fusion protein disclosed herein in a host cell under suitable conditions permitting the production of the polypeptide and recovering the polypeptide so produced.

IV. Methods of Use

Various methods are provided for modulating an immune response. As used herein, the term "modulating" includes inducing, inhibiting, potentiating, elevating, increasing, or decreasing a given activity or response.

By "subject" is intended mammals, e.g., primates, humans, agricultural and domesticated animals such as, but not limited to, dogs, cats, cattle, horses, pigs, sheep, and the like. In one embodiment, the subject undergoing treatment with the pharmaceutical formulations provided herein is a human.

A "therapeutically effective amount" of an IL-2/IL-2Rα fusion protein refers to the amount of the IL-2/IL-2Rα fusion protein sufficient to elicit a desired biological response. As will be appreciated by one of ordinary skill in the art, the absolute amount of a particular IL-2/IL-2Rα fusion protein that is effective can vary depending on such factors as the desired biological endpoint, the IL-2/IL-2Rα fusion protein to be delivered, the target cell or tissue, and the like. One of ordinary skill in the art will further understand that an effective amount can be administered in a single dose, or can be achieved by administration of multiple doses (i.e., 1, 2, 3, 4, 5, 6, 7, 8, 9, 10 or more doses).

i. Methods for Increasing an Immune Response

Various methods are provided for increasing the immune response in a subject. Such methods comprise administering to a subject in need of an increase in the immune response a therapeutically effective amount of an IL-2/IL-2Rα fusion protein. As such, in specific embodiments, transient application of higher doses of IL-2 are employed to boosted immune effector and memory responses.

It is further recognized that the various IL-2/IL-2Rα fusion protein can be used in combination with an antigen to enhance the immune response to the antigen. Thus, the IL-2/IL-2Rα fusion protein can also be used as a vaccine adjuvant especially to boost cell-mediated immune memory.

For example, the IL-2/IL-2Rα fusion protein can be used to enhance a vaccine preparation. Thus, the various IL-2/IL-2Rα fusion proteins are useful for increasing the efficacy of anti-cancer vaccines or for vaccines that are poorly immunogenic. Further provided are methods for enhancing the efficacy or immunogenicity of a vaccine in a subject, or overcoming a suppressed immune response to a vaccine in a subject, including (i) administering to the subject a therapeutically effective amount of an IL-2/IL-2Rα fusion protein and (ii) administering to the subject a vaccine.

By "vaccine" is intended a composition useful for stimulating a specific immune response (or immunogenic response) in a subject. In some embodiments, the immunogenic response is protective or provides protective immunity. For example, in the case of a disease-causing organism the vaccine enables the subject to better resist infection with or disease progression from the organism against which the vaccine is directed. Alternatively, in the case of a cancer, the vaccine strengthens the subject's natural defenses against cancers that have already developed. These types of vaccines may also prevent the further growth of existing cancers, prevent the recurrence of treated cancers, and/or eliminate cancer cells not killed by prior treatments.

Representative vaccines include, but are not limited to, vaccines against diphtheria, tetanus, pertussis, polio, measles, mumps, rubella, hepatitis B, *Haemophilus influenzae* type b, varicella, meningitis, human immunodeficiency virus, tuberculosis, Epstein Barr virus, malaria, hepatitis E, dengue, rotavirus, herpes, human papillomavirus, and cancers. Vaccines of interest include the two vaccines that have been licensed by the U.S. Food and Drug Administration to prevent virus infections that can lead to cancer: the hepatitis B vaccine, which prevents infection with the hepatitis B virus, an infectious agent associated with liver cancer (*MMWR Morb. Mortal. Wkly. Rep.* 46:107-09, 1997); and Gardasil™, which prevents infection with the two types of human papillomavirus that together cause 70 percent of cervical cancer cases worldwide (Speck and Tyring, *Skin Therapy Lett.* 11:1-3, 2006). Other treatment vaccines of interest include therapeutic vaccines for the treatment of cancer, cervical cancer, follicular B cell non-Hodgkin's lymphoma, kidney cancer, cutaneous melanoma, ocular melanoma, prostate cancer, and multiple myeloma.

By "enhancing the efficacy" or "enhancing the immunogenicity" with regard to a vaccine is intended improving an outcome, for example, as measured by a change in a specific value, such as an increase or a decrease in a particular parameter of an activity of a vaccine associated with protective immunity. In one embodiment, enhancement refers to at least a 5%, 10%, 25%, 50%, 100% or greater than 100% increase in a particular parameter. In another embodiment, enhancement refers to at least a 5%, 10%, 25%, 50%, 100% or greater than 100% decrease in a particular parameter. In one example, enhancement of the efficacy/immunogenicity of a vaccine refers to an increase in the ability of the vaccine to inhibit or treat disease progression, such as at least a 5%, 10%, 25%, 50%, 100%, or greater than 100% increase in the effectiveness of the vaccine for that purpose. In a further example, enhancement of the efficacy/immunogenicity of a vaccine refers to an increase in the ability of the vaccine to recruit the subject's natural defenses against cancers that have already developed, such as at least a 5%, 10%, 25%, 50%, 100%, or greater than 100% increase in the effectiveness of the vaccine for that purpose.

Similarly, by "overcoming a suppressed immune response" with regard to a vaccine is intended improving an outcome, for example, as measured by a change in a specific value, such as a return to a formerly positive value in a particular parameter of an activity of a vaccine associated with protective immunity. In one embodiment, overcoming refers to at least a 5%, 10%, 25%, 50%, 100% or greater than 100% increase in a particular parameter. In one example, overcoming a suppressed immune response to a vaccine refers to a renewed ability of the vaccine to inhibit or treat disease progression, such as at least a 5%, 10%, 25%, 50%, 100%, or greater than 100% renewal in the effectiveness of the vaccine for that purpose. In a further example, overcoming a suppressed immune response to a vaccine refers to a renewed ability of the vaccine to recruit the subject's natural defenses against cancers that have already developed, such as at least a 25%, 50%, 100%, or greater than 100% renewal in the effectiveness of the vaccine for that purpose.

By "therapeutically effective amount" is intended an amount that is useful in the treatment, prevention or diagnosis of a disease or condition. As used herein, a therapeutically effective amount of an IL-2/IL-2Rα fusion protein is an amount which, when administered to a subject, is sufficient to achieve a desired effect, such as modulating an immune response in a subject without causing a substantial cytotoxic effect in the subject. As outlined above, a therapeutically effective amount of an IL-2/IL-2Rα fusion protein can be administered to a subject to increase an immune response, enhance the immune response to an antigen, enhance the efficacy or immunogenicity of a vaccine in a subject, or to overcome a suppressed immune response to a vaccine. The effective amount of an IL-2/IL-2Rα fusion protein useful for modulating such functions will depend on the subject being treated, the severity of the affliction, and the manner of administration of the IL-2/IL-2Rα fusion protein. Exemplary doses include about $10^4$ to about $10^7$ IU of IL-2 activity per adult, about $10^4$ to $10^5$ IU of IL-2 activity per adult, about $10^5$ to about $10^6$ IU of IL-2 activity per adult, about $10^6$ to about $10^7$ IU of IL-2 activity per adult. In other instances, the therapeutically effective dose of the IL-2/IL-2Rα fusion protein is about $10^5$ IU of IL-2 activity ±100-fold, is about $10^5$ IU of IL-2 activity ±10-fold, about $10^5$ IU of IL-2 activity ±2-fold, about $10^5$ IU of IL-2 activity ±20-fold, about $10^5$ IU of IL-2 activity ±30-fold, about $10^5$ IU of IL-2 activity ±40-fold, about $10^5$ IU of IL-2 activity ±50-fold, about $10^5$ IU of IL-2 activity ±60-fold, about $10^5$ IU of IL-2 activity ±70-fold, about $10^5$ IU of IL-2 activity ±80-fold, or about $10^5$ IU of IL-2 activity ±90-fold. In a specific non-limiting embodiment, a human IL-2 fusion protein is administered at this dosage.

In one embodiment, the reference standard for the mouse IL-2 fusion protein is the mouse IL-2 is from eBiosciences (Catalog Number: 14-8021). Briefly, the bioactivity of mouse IL-2 from eBioscience is as follows: The ED50 of this protein, as measured by CTLL-2 cell proliferation assay, is less than or equal to 175 pg/mL. This corresponds to a specific activity of greater than or equal to $5.7 \times 10^6$ Units/mg.

In another embodiment, the reference standard for the human IL-2 fusion protein is the human IL-2 drug Aldesleukin (Proleukin) Thus, the IL-2 fusion proteins disclosed herein are directly compared to the fusion protein to the IL-2 drug that is used in low dose or high dose IL-2 therapy. IL-2 activity for mouse and human IL-2 use the same assay and their activity in units/mg are similar. With respect to the human IL-2 drug, i.e. aldesleukin (Proleukin), the standard measure of an amount IL-2 is the International Unit (IU) which technically is not a fixed amount but the amount that produces a fixed effect in a specific assay of biological activity, i.e. CTLL proliferation assay. In practice, the manufacture of IL-2 is standardized and there is a conversion between drug weight and International Units. It is 1.1 mg IL-2=18 million IU (abbreviated 18 MIU).

It is furthermore understood that appropriate doses of a functional agent depend upon the potency of the active agent with respect to the activity to be modulated. Such appropriate doses may be determined using the assays described herein. In addition, it is understood that the specific dose level for any particular animal subject will depend upon a variety of factors including the activity of the specific compound employed, the age, body weight, general health, gender, and diet of the subject, the time of administration, the route of administration, the rate of excretion, and/or any drug combination.

When administration is for the purpose of treatment, administration may be for either a prophylactic or therapeutic purpose. When provided prophylactically, the substance is provided in advance of any symptom. The prophylactic administration of the substance serves to prevent or attenuate any subsequent symptom. When provided therapeutically, the substance is provided at (or shortly after) the onset of a symptom. The therapeutic administration of the substance serves to attenuate any actual symptom.

The skilled artisan will appreciate that certain factors may influence the dosage required to effectively treat a subject, including but not limited to, the severity of the disease or disorder, previous treatments, the general health and/or age of the subject, and other diseases present. Moreover, treatment of a subject with a therapeutically effective amount of an IL-2/IL-2Rα fusion protein can include a single treatment or, preferably, can include a series of treatments. It will also be appreciated that the effective dosage of an IL-2/IL-2Rα fusion protein used for treatment may increase or decrease over the course of a particular treatment. Changes in dosage may result and become apparent from the results of diagnostic assays as described herein.

Therapeutically effective amounts of an IL-2/IL-2Rα fusion protein can be determined by animal studies. When animal assays are used, a dosage is administered to provide a target in vivo concentration similar to that which has been shown to be effective in the animal assays.

ii. Methods for Decreasing an Immune Response

Various methods are provided for decreasing the immune response in a subject. Such methods comprise administering to a subject in need of a decrease in the immune response a therapeutically effective amount of an IL-2/IL-2Rα fusion protein.

There is much interest to harness the suppressive power of Tregs to inhibit unwanted immune responses. Data in mouse and man shows that enhancing IL-2R signaling with a low dose of IL-2 selectively boosts Tregs and enhances immune tolerogenic mechanisms. IL-2/IL-2Rα fusion proteins provided herein represent a new and improved form of IL-2 that more potentially enhances Tregs. Thus, the IL-2/IL-2Rα fusion proteins can be administered to patients with autoimmune diseases, chronic graft versus host disease, transplant rejection reactions, and other conditions where the goal is to suppress self-reactivity.

For example, a therapeutically effective amount of an IL-2/IL-2Rα fusion protein that promotes immune tolerance can find use, for example, in treating a subject having an autoimmune or an inflammatory disorder, including but not limited to, graft rejections and allergies. Thus, in one embodiment, a method of treating a subject having an autoimmune or inflammatory disorder is provided. Such a method comprises administering to the subject a therapeutically effective amount of an IL-2/IL-2Rα fusion protein.

Non-limiting examples of autoimmune disorders that can be treated or prevented include type1 diabetes, multiple sclerosis, rheumatoid arthritis, celiac disease, systemic lupus erythematosus, juvenile idiopathic arthritis, Crohn's disease, ulcerative colitis or systemic sclerosis, graft versus host disease, HCV-induced vasculitis, alopecia areata or psoriasis.

Additional autoimmune diseases include those where there is already an indication that Tregs may be impaired and would benefit from IL-2-dependent boosting of Tregs. In this regard, single nucleotide polymorphisms (SNPs) in IL-2, IL-2Rα, or IL-2R13 have been associated as a genetic risk for type 1 diabetes, multiple sclerosis, rheumatoid arthritis, celiac disease, systemic lupus erythematosus, juvenile idiopathic arthritis, Crohn's disease, ulcerative colitis, and systemic sclerosis. Studies suggest that the genetic risk is related to impaired Treg numbers and/or activity. In addition, low dose IL-2 therapy has shown to benefit patients with chronic GvHD and HCV-induced vasculitis. Thus, such patients populations can also be administered a therapeutically effective amount of an IL-2/IL-2Rα fusion protein.

In other embodiments, the IL-2/IL-2Rα fusion protein can be used in combination with a therapeutic agent to reduce the immune response to the agent (i.e. protein). For example, the IL-2/IL-2Rα fusion protein can be used in combination with a therapeutic protein which must be chronically administered to a subject. Thus, in a specific embodiment, the method comprises includes administering to the subject at least one additional therapeutic agent in combination with an IL-2/IL-2Rα fusion protein. Such therapeutic agents, include but are not limited to, a cytokine, a glucocorticoid, an anthracycline (e.g., doxorubicin or epirubicin), a fluoroquinolone (e.g., ciprofloxacin), an antifolate (e.g., methotrexate), an antimetabolite (e.g., fluorouracil), a topoisomerase inhibitor (e.g., camptothecin, irinotecan or etoposide), an alkylating agent (e.g., cyclophosphamide, ifosfamide, mitolactol, or melphalan), an antiandrogen (e.g., flutamide), an antiestrogen (e.g., tamoxifen), a platinum compound (e.g., cisplatin), a vinca alkaloid (e.g., vinorelbine, vinblastine or vindesine), or mitotic inhibitor (e.g., paclitaxel or docetaxel).

Moreover, the therapeutically effective amount of the IL-2/IL-2Rα fusion protein can further be administered in combination therapies to increase Tregs and tolerance. Such combination therapies can comprises the therapeutically effective amount of the IL-2/IL-2Rα fusion protein in combination with anti-TNFα or other agents to inhibit inflammatory responses.

The therapeutically effective amount of an IL-2/IL-2Rα fusion protein useful for decreasing an immune response will depend on the subject being treated, the severity of the affliction, and the manner of administration of the IL-2/IL-2Rα fusion protein. Exemplary doses include about $10^3$ IU to about $10^6$ IU of IL-2 activity per adult or about $10^4$ IU to about $10^6$ IU of IL-2 activity per adult. Exemplary doses include about $10^3$ to about $10^6$ IU of IL-2 activity per adult, about $10^3$ to about $10^4$ IU of IL-2 activity per adult, about $10^4$ to about $10^6$ IU of IL-2 activity per adult, about $10^4$ to $10^5$ IU of IL-2 activity per adult, or about $10^5$ to about $10^6$ IU of IL-2 activity per adult. In other instances, the therapeutically effective dose of the IL-2/IL-2Rα fusion protein is about $10^4$ IU of IL-2 activity ±100-fold, is about $10^4$ IU of IL-2 activity ±10-fold, about $10^4$ IU of IL-2 activity ±2-fold, about $10^4$ IU of IL-2 activity ±20-fold, about $10^4$ IU of IL-2 activity ±30-fold, about $10^4$ IU of IL-2 activity ±40-fold, about $10^4$ IU of IL-2 activity ±50-fold, about $10^4$ IU of IL-2 activity ±60-fold, about $10^4$ IU of IL-2 activity ±70-fold, about $10^4$ IU of IL-2 activity ±80-fold, or about $10^4$ IU of IL-2 activity ±90-fold. In a specific non-limiting embodiment, a human IL-2 fusion protein is administered at this dosage.

In one embodiment, the reference standard for the mouse IL-2 fusion protein is the mouse IL-2 is from eBiosciences (Catalog Number: 14-8021). Briefly, the bioactivity of mouse IL-2 from eBioscience is as follows: The ED50 of this protein, as measured by CTLL-2 cell proliferation assay, is less than or equal to 175 pg/mL. This corresponds to a specific activity of greater than or equal to $5.7 \times 10^6$ Units/mg.

In another embodiment, the reference standard for the human IL-2 fusion protein is the human IL-2 drug Aldesleukin (Proleukin) Thus, the IL-2 fusion proteins disclosed herein are directly compared to the fusion protein to the IL-2 drug that is used in low dose or high dose IL-2 therapy. IL-2 activity for mouse and human IL-2 use the same assay and their activity in units/mg are similar. With respect to the human IL-2 drug, i.e. aldesleukin (Proleukin), the standard measure of an amount IL-2 is the International Unit (IU) which technically is not a fixed amount but the amount that produces a fixed effect in a specific assay of biological activity, i.e. CTLL proliferation assay. In practice, the manufacture of IL-2 is standardized and there is a conversion between drug weight and International Units. It is 1.1 mg IL-2=18 million IU (abbreviated 18 MIU).

It is furthermore understood that appropriate doses of a functional agent depend upon the potency of the active agent with respect to the expression or activity to be modulated. Such appropriate doses may be determined using the assays described herein. In addition, it is understood that the specific dose level for any particular animal subject will depend upon a variety of factors including the activity of the specific compound employed, the age, body weight, general health, gender, and diet of the subject, the time of administration, the route of administration, the rate of excretion, and/or any drug combination.

When administration is for the purpose of treatment, administration may be for either a prophylactic or therapeutic purpose. When provided prophylactically, the substance is provided in advance of any symptom. The prophylactic administration of the substance serves to prevent or attenuate any subsequent symptom. When provided therapeutically, the substance is provided at (or shortly after) the onset of a symptom. The therapeutic administration of the substance serves to attenuate any actual symptom.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an IL-2/IL-2Rα fusion protein can include a single treatment or, preferably, can include a series of treatments. It will also be appreciated that the effective dosage of an IL-2/IL-2Rα fusion protein used for treatment may increase or decrease over the course of a particular treatment. Changes in dosage may result and become apparent from the results of diagnostic assays as described herein.

Therapeutically effective amounts of an IL-2/IL-2Rα fusion protein can be determined by animal studies. When animal assays are used, a dosage is administered to provide a target tissue concentration similar to that which has been shown to be effective in the animal assays.

iii. Pharmaceutical Composition

The various IL-2/IL-2Rα fusion proteins disclosed herein (also referred to herein as "active compounds") can be incorporated into pharmaceutical compositions suitable for administration. Such compositions typically comprise the fusion protein and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal. In addition, it may be desirable to administer a therapeutically effective amount of the pharmaceutical composition locally to an area in need of treatment. This can be achieved by, for example, local or regional infusion or perfusion during surgery, topical application, injection, catheter, suppository, or implant (for example, implants formed from porous, non-porous, or gelatinous materials, including membranes, such as sialastic membranes or fibers), and the like. In another embodiment, the therapeutically effective amount of the pharmaceutical composition is delivered in a vesicle, such as liposomes (see, e.g., Langer, *Science* 249:1527-33, 1990 and Treat et al., in *Liposomes in the Therapy of Infectious Disease and Cancer*, Lopez Berestein and Fidler (eds.), Liss, N.Y., pp. 353-65, 1989).

In yet another embodiment, the therapeutically effective amount of the pharmaceutical composition can be delivered in a controlled release system. In one example, a pump can be used (see, e.g., Langer, *Science* 249:1527-33, 1990; Sefton, *Crit. Rev. Biomed. Eng.* 14:201-40, 1987; Buchwald et al., *Surgery* 88:507-16, 1980; Saudek et al., *N. Engl. J. Med.* 321:574-79, 1989). In another example, polymeric materials can be used (see, e.g., Levy et al., *Science* 228:190-92, 1985; During et al., *Ann. Neurol.* 25:351-56, 1989; Howard et al., *J. Neurosurg.* 71:105-12, 1989). Other controlled release systems, such as those discussed by Langer (*Science* 249:1527-33, 1990), can also be used.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, NJ), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethyelene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such a functional compound for the treatment of individuals.

The pharmaceutical compositions can be included in a container, pack, or dispenser together with instructions for administration.

iv. Kits

As used herein, a "kit" comprises an IL-2/IL-2Rα fusion protein for use in modulating the immune response, as described elsewhere herein. The terms "kit" and "system," as used herein are intended to refer to at least one or more IL-2/IL-2Rα fusion protein which, in specific embodiments, are in combination with one or more other types of elements or components (e.g., other types of biochemical reagents, containers, packages, such as packaging intended for commercial sale, instructions of use, and the like).

V. Sequence Identity

As described above, active variants and fragments of the IL-2/IL-2Rα fusion proteins or the polynucleotide encoding the same, including the various components of the IL-2/IL-2Rα fusion protein are provided. Such components include, IL-2, the extracellular domain of IL-2Rα, the linker sequences or the Kozak sequence. The activity retained by the active variant or fragment of the fusion protein or a given component of the fusion protein is discussed in further detail elsewhere herein.

Such variants can have at least 90%, 91%, 92%, 93%, 94%, 95%, 96%, 97%, 98%, or 99% sequence identity to a given reference polypeptide or polynucleotide. A fragment can comprise at least 10, 20, 30, 50, 75, 100, 200, 300, 400, 500, 600, 700, 800, 900, 1000, 1500, 2000 contiguous nucleotides of a given reference nucleotide sequence or up to the full length of a given nucleotide reference sequence; or a fragment can comprise at least 10, 20, 30, 40, 50, 60, 70, 75, 80, 90, 100, 110, 120, 130, 140, 150, 160, 170, 180, 190, 200 contiguous amino acids or up to the full length of a given reference polypeptide sequence.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

As used herein, the singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description.

The subject matter of the present disclosure is further illustrated by the following non-limiting examples.

EXPERIMENTAL

Figure 4:
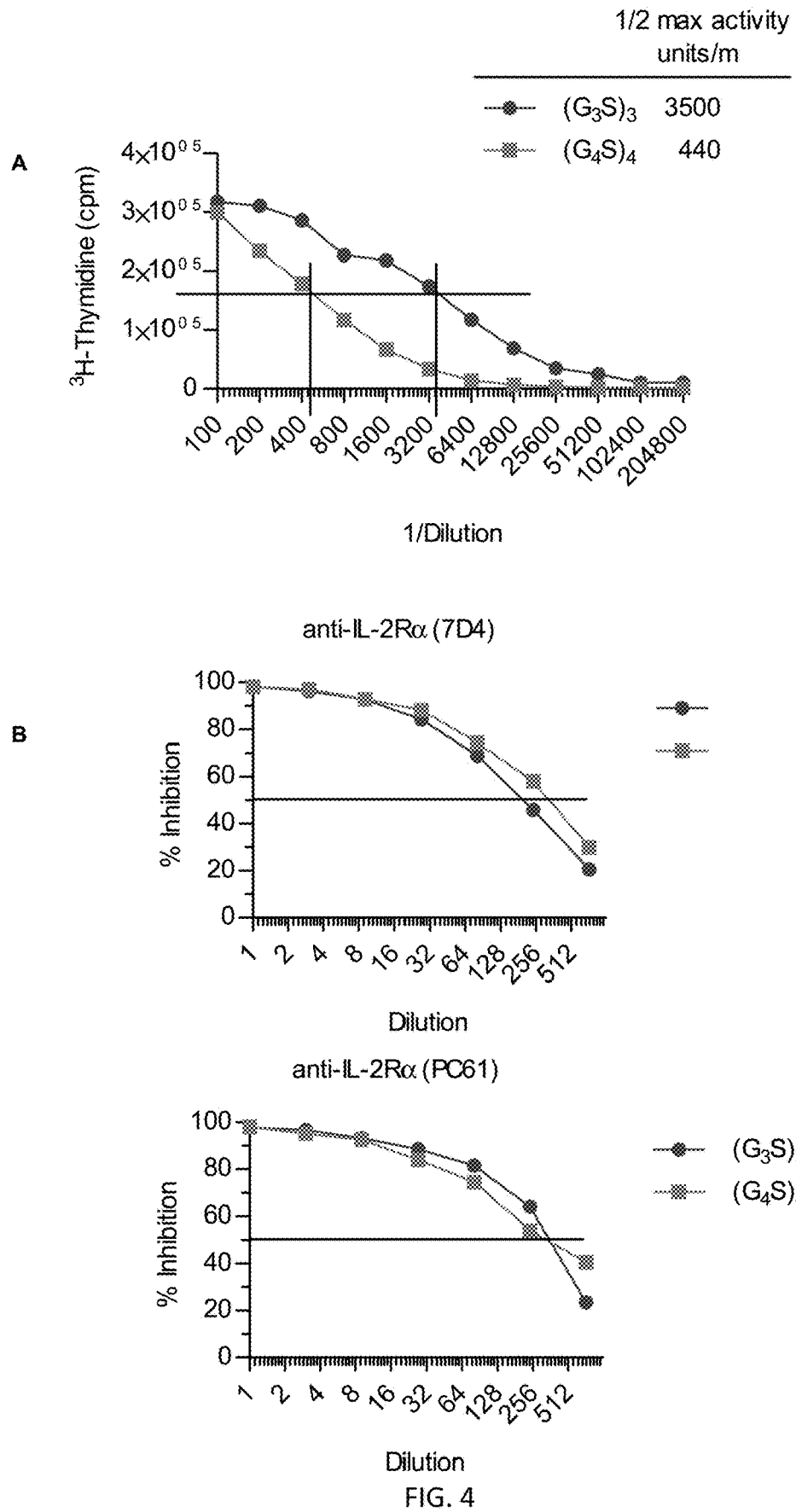
FIG. 4 shows the activity of purified IL-2/IL-2Rα fusion proteins. Supernatants of transfected CHO cells were used to purify IL-2/(G$_3$S)$_3$/IL-2Rα and IL-2/(Gly$_4$Ser)$_4$/IL-2Rα by Nickel-based affinity chromatography to the 6×-His tag. (A) IL-2 bioactivity measure by proliferation of anti-CD3 T cell blast to the indicated purified fusion protein. (B) The effect of each purified fusion protein to inhibit the binding of PC61 and 7D4 anti-IL-2Rα monoclonal antibodies, directed to non-ligand binding site, to anti-CD3 activated T cell blasts.

IL-2 is a biologic that has been used in attempts to boost immune responses in cancer and HIV/AID patients. More recently much lower doses of IL-2 have been used to selectively boost tolerance to suppress unwanted immune responses associated with autoimmune-like attack of self-tissues. Importantly, these low doses of IL-2 have not shown signs of enhancing or re-activation of autoreactive T cells. Nevertheless, IL-2 has important drawbacks as a therapeutic, including a very short-half life in vivo, which limits its efficacy, and toxicity at high doses. For these reasons a new IL-2 biologic has been produced with the goals of improving its pharmacokinetics and durability of responses for use 1)

in low dose IL-2-based therapy to boost regulatory T cells (Tregs) and immune tolerance and 2) in adjuvant therapy with higher doses to boost immune responses and memory. To achieve these goals, IL-2/IL-2Rα fusion proteins have been developed, where these fusions were designed to increase IL-2 availability by increasing persistent IL-2 stimulation of IL-2R-bearing lymphocytes in vivo. These fusions consist of engineered proteins as follows (FIG. 1): 1) a leader sequence of IL-2 that contains an optimized Kozak sequence for efficient translation; 2) the full length sequence of IL-2; 3) a glycine or glycine/serine linker sequence of variable length; 4) the coding sequence of the expressed extracellular domain of IL-2Rα; 5) a 2 amino acid glycine spacer; 6) a six amino acid poly-histidine region for purification; and 7) two termination codons. The predicted protein sequences from these mouse and human cDNAs are shown for IL-2/(GlySer)/IL-2Rα fusion proteins in FIG. 2A and FIG. 2B, respectively. These cDNAs were cloned into the pClneo expression vector and used for expression of these fusion proteins in COS7 cells. Analysis of the culture supernatants indicated that each mouse fusion protein exhibited IL-2 bioactivity in vitro, with optimal activity associated with the IL-2/(Gly$_3$Ser)$_3$/IL-2Rα fusion protein (FIG. 3A). Accordingly, inclusion of anti-IL-2 in this bioassay completely inhibited proliferation (FIG. 3B). Larger amounts of IL-2/(Gly$_3$Ser)$_3$/IL-2Rα and IL-2/(Gly$_4$Ser)$_4$/IL-2Rα were prepared after expression in CHO cells and purified by affinity chromatography through binding of the 6× His tag of the fusion protein to immobilized nickel. The mouse IL-2/(Gly$_3$Ser)$_3$/IL-2Rα fusion protein showed greater IL-2 bioactivity than IL-2/(Gly$_4$Ser)$_4$/IL-2Rα (FIG. 4A) even though both fusion proteins similarly inhibited the binding of two anti-IL2Rα antibodies (PC61 and 7D4) (FIG. 4B) to cells expressing IL-2Rα, confirming greater IL-2 activity is associated with the former fusion protein. The inhibition of binding of PC61 and 7D4 also indicates that IL-2Rα portion of the fusion protein retained sufficient tertiary structure to bind these antibodies. However, these fusion proteins did not inhibit the binding of a monoclonal antibody (3C7) directed to the IL-2 binding site of IL-2Rα, to cells expressing IL-2Rα. This result implies that IL-2 within the IL-2/IL-2Rα fusion protein in spatially near the binding site of IL-2Rα (FIG. 5). Western blot analysis of these fusion proteins showed that IL-2/IL-2Rα was 55-65 kDa, with somewhat faster mobility under non-reducing condition, and that it was approximately 15 kDa larger than that observed for soluble IL-2Rα (FIG. 6A). Correspondingly, direct analysis of the purified mouse IL-2/(Gly$_3$Ser)$_3$/IL-2Rα by SDS-PAGE was consistent with a heterogeneous 55-65 kDa monomer protein (FIG. 6B), which is the expected size for an IL-2 (15 kDa) and IL-2Rα (40-50 kDa) fusion molecule (FIG. 6), where IL-2Rα shows size heterogeneity due to extensive variable glycosylation (Malek and Korty, *J. Immunol.* 136:4092-4098, 1986). An immediate consequence of IL-2-dependent signal transduction is tyrosine phosphorylation of STAT5 (pSTAT5). Treatment of mice with mouse IL-2/(Gly$_3$Ser)$_3$/IL-2Rα resulted in extensive and selective activation of pSTAT5 in Tregs 30 min post-treatment (FIG. 7). Dose-response studies showed that mouse IL-2/(Gly$_3$Ser)$_3$/IL-2Rα affected a number of key activities of Tregs in vivo (FIG. 8). These effects on Tregs included: increased representation (FIG. 8A) and number (not shown) of Tregs in the CD4$^+$ T cell compartment; upregulation of IL-2-dependent CD25 (FIG. 8B); increased proliferation as assess by expression of the proliferative marker Ki67 (FIG. 8C); and increased fraction of IL-2-dependent terminally differentiated Klrg1$^+$ Treg subset (FIG. 8D). These effects were most striking for Tregs in the spleen and the inflamed pancreas of non-obese diabetic (NOD) mice. 1000 units of IL-2 activity, as measured in the standard CTLL IL-2 bioassay, associated with IL-2/(Gly$_3$Ser)$_3$/IL-2Rα showed lower, but readily measurable effects on Tregs (FIG. 8). C57/BL6 mice treated with IL-2/(Gly$_3$Ser)$_3$/IL-2Rα (2000 units of IL-2 activity) were compared to mice that received recombinant IL-2 (25,000 units) or agonist complexes of IL-2/anti-IL-2 (IL2/IC) (10,000 units of IL-2 activity) (FIG. 9). IL-2/(Gly$_3$Ser)$_3$/IL-2Rα was much more effective than recombinant IL-2 and slightly more effective than IL2/IC in inducing persistent augmentation of Tregs and related properties (FIG. 9). These increases in tolerogenic Tregs occurred at 5- and 12.5-fold lower levels of IL-2 activity in comparison to IL2/IC and recombinant IL-2, respectively. When considering IL-2-dependent activation of pSTAT5 in Tregs directly ex vivo (FIG. 9), these data suggest a biological half-life of approximately 72 hours for IL-2/IL-2Rα. Pre-diabetic NOD mice underwent a short course of treatment with low amounts of IL-2/IL-2Rα (FIG. 10). A delay in the onset of diabetes was observed in those mice that were treated with 800 U of IL-2 activity associated with IL-2/IL-2Rα. With respect to immunity, application of a single high dose of IL-2/(Gly$_3$Ser)$_3$/IL-2Rα (12,000 U of IL-2 activity) also substantially boosted CD8$^+$ T cell responses, especially long-lived memory cells (FIG. 11). Early after immunization (day 28), CD44$^{hi}$CD62L$^{lo}$CD127$^{hi}$ effector-memory (EM) cells dominated the memory pool; however, with increasing time CD44$^{hi}$CD62L$^{hi}$CD127$^{hi}$ central memory (CM) cells increased, and CM cells dominated the memory pool 202 days post-immunization (FIG. 12). Thus, IL-2/(Gly$_3$Ser)$_3$/IL-2Rα functions in an analogous manner to recombinant IL-2 to boost tolerogenic and immune suppressive Tregs and immunity through increasing T effector/memory responses, but it exhibits improved pharmacokinetics by delivering such responses: 1) at a lower effective levels of IL-2 activity; 2) with more persistent biological responses; and 3) retaining the hierarchy with Tregs responsive at lower doses than T effector/memory cells. These findings support the notion that IL-2/IL-2Rα fusion proteins represent an improved and new class of drugs to deliver IL-2 activity to selectively boost immune tolerance or immune memory when administered at the proper dose and regimen.

IL-2/IL-2Rα fusion proteins were also produced that comprise human IL-2 and human IL-2Rα (FIG. 1, FIG. 2B). These cDNAs were expressed in CHO cells and the secreted fusion proteins were purified on Nickel affinity chromatography based on the 6×-His tag. Fusion proteins varied in the length of the glycine/serine linkers in an analogous manner to those used for mouse IL-2/IL-2Rα. All 4 of the resulting human IL-2/IL-2Rα fusion proteins exhibited IL-2 bioactivity using the mouse CTLL assay (FIG. 13A). Western blot analysis confirmed that human IL-2/IL-2Rα also showed a heterogeneous band between 55-60 kDa (FIG. 13B), consistent with highly glycosylated molecules expected for IL-2 linked to IL-2Rα. The IL-2/IL-2Rα fusion proteins with the (G$_3$S)$_3$ and especially the (G$_4$S)$_4$ linkers may have greater activity because less fusion protein was seen even though equivalent amount of IL-2 activity was loaded on each lane (FIG. 13B). The capacity of the fusion protein to inhibit the binding of anti-IL-2Rα monoclonal antibodies, M-A257 and BC96, to cells bearing human IL-2Rα indicates that IL-2Rα of the fusion protein retained sufficient tertiary structure to bind these antibodies (FIG. 14). However, these fusion proteins only partially inhibited the binding of a monoclonal antibody (BC96) directed to the IL-2 binding site of IL-2Rα, implying that IL-2 within the IL-2/IL-2Rα fusion protein is spatially near the binding site of IL-2Rα. Moreover, we estimated the specific activity of the mouse and human IL-2/IL-2Rα fusion proteins containing the (G₃S)₃ linker to be 80 and 2000 pM, respectively, for 1 unit/ml of IL-2 bioactivity activity. These values are much higher than the activity of recombinant IL-2, which is 10 pM at 1 unit/ml. The distinct activities between human and mouse IL-2/IL-2Rα is at least partially accounted for by a relative ineffectiveness of the human fusion protein to support the proliferation of mouse CTLL cells in the bioassay compared to the mouse fusion proteins or mouse and human recombinant IL-2 (not shown). These relatively low specific activities and the antibody blocking results (FIG. 5 and FIG. 12) raised the possibility that there is a specific intramolecular interaction between IL-2 and IL-2Rα in the context of the fusion protein that limits the amount of IL-2 in the fusion protein to stimulate cells bearing the IL-2R. To directly test this notion, two arginine residues within the IL-2 binding site of human IL-2Rα (see Robb et al., *Proc. Natl. Acad. Sci. USA*, 85:5654-5658, 1988) were mutated to threonine and serine. We detected much greater bioactivity associated with these mutant IL-2R fusion proteins (FIG. 15); the specific activity of the mutated IL-2/IL-2Rα fusion proteins was estimated to be approximately 5 pM for 1 unit/ml of IL-2 activity, a value very similar to recombinant IL-2. Thus, these data indicate that human IL-2/IL-2Rα is biologically active and one specific mechanism of action that accounts for the prolonged IL-2 activity in these fusion proteins is through a competitive interaction between the IL-2 moiety with the IL-2 binding region of IL-2Rα of the fusion protein and with cells that express the IL-2R.

TABLE 1

Summary of Sequences

| SEQ ID NO | AA/NT | Source | Description | |
|---|---|---|---|---|
| 1 | AA | Human | IL-2-unprocessed | GenBank Acc. No. AAB46883 IL-2<br>myrmqllsci alslalvtns aptssstkkt qlqlehllld lqmilnginn<br>yknpkltrmltfkfympkka telkhlqcle eelkpleevl nlaqsknfhl rprdlisnin<br>vivlelkgsettfmceyade tativeflnr witfcqsiis tlt |
| 2 | AA | Human | IL-2-mature form | GenBank AAB46883 with first 20 aa removed<br>aptssstkkt qlqlehllld lqmilnginn yknpkltrmltfkfympkka telkhlqcle<br>eelkpleevl nlaqsknfhl rprdlisnin vivlelkgse<br>ttfmceyade tativeflnr witfcqsiis tlt |
| 3 | AA | Mouse | IL-2 unprocessed | Acc No. P04351<br>MYSMQLASCV TLTLVLLVNS APTSSSTSSS TAEAQQQQQQ<br>QQQQQQHLEQ LLMDLQELLS RMENYRNLKL PRMLTFKFYL<br>PKQATELKDL QCLEDELGPL RHVLDLTQSK SFQLEDAENF<br>ISNIRVTVVK LKGSDNTFEC QFDDESATVV DFLRRWIAFC QSIISTSPQ |
| 4 | AA | Mouse | IL-2 mature form | Mature form of Acc No. P04351<br>APTSSSTSSS TAEAQQQQQQ<br>QQQQQQHLEQ LLMDLQELLS RMENYRNLKL PRMLTFKFYL<br>PKQATELKDL QCLEDELGPL RHVLDLTQSK SFQLEDAENF<br>ISNIRVTVVK LKGSDNTFEC QFDDESATVV DFLRRWIAFC QSIISTSPQ |
| 5 | AA | Human | IL-2Rα unprocessed form | Genebank Acc No. NP_000408.1<br>mdsyllmwgl ltfimvpgcq aelcdddppe iphatfkama ykegtmlnce<br>ckrgfrriksgslymlctgn sshsswdnqc qctssatrnt tkqvtpqpee<br>qkerkttemq spmqpvdqaslpghcreppp weneateriy hfvvgqmvyy<br>qcvqgyralh rgpaesvckm thgktrwtqpqlictgemet sqfpgeekpq<br>aspegrpese tsclvtttdf qiqtemaatm etsiftteyqvavagcvfll isvlllsglt<br>wqrrqrksrr ti |
| 6 | AA | Human | IL-2Rα mature form | First 1-21 AA removed from NP_000408.1<br>elcdddppe iphatfkama ykegtmlnce ckrgfrriksgslymlctgn<br>sshsswdnqc qctssatrnt tkqvtpqpee qkerkttemq spmqpvdqas<br>lpghcreppp weneateriy hfvvgqmvyy qcvqgyralh rgpaesvckm<br>thgktrwtqpqlictgemet sqfpgeekpq aspegrpese tsclvtttdf<br>qiqtemaatm etsiftteyqvavagcvfll isvlllsglt wqrrqrksrr ti |
| 7 | AA | Human | Mature form of IL-2Rα extracellular domain | ELCDDDPPEIPHATFKAMAYKEGTMLNCECKRGFRRIKSGSLYMLCTGN<br>SSHSSWDNQCQCTSSATRNTTKQVTPQPEEQKERKTTEMQSPMQPVD<br>QASLPGHCREPPPWENEATERIYHFVVGQMVYYQCVQGYRALHRGPA<br>ESVCKMTHGKTRWTQPQLICTGEMETSQFPGEEKPQASPEGRPESETS<br>CLVTTTDFQIQTEMAATMETSIFTTEYQ |
| 8 | AA | Mouse | IL-2Rα unprocessed form | Acc No. NP_032393.3<br>meprllmlgf lsltivpscr aelclydppe vpnatfkals ykngtilnce<br>ckrgfrrlkelvymrclgns wssncqctsn shdksrkqvt aqlehqkeqq<br>tttdmqkptq smhqenltghcrepppwkhe dskriyhfve gqsvhyecip<br>gykalqrgpa isickmkcgk tgwtqpqltcvderehhrfl aseesqgsrn<br>sspesetscp itttdfpqpt ettamtetfv ltmeykvavasclfllisil llsgltwqhr<br>wrksrrti |

TABLE 1-continued

Summary of Sequences

| SEQ ID NO | AA/NT | Source | Description | |
|---|---|---|---|---|
| 9 | AA | Mouse | IL-2Rα mature form | aa 1-21 removed from Acc No. NP_032393.3<br>elclydppe vpnatfkals ykngtilnce ckrgfrrlke lvymrclgns wssncqctsn<br>shdksrkqvt aqlehqkeqq tttdmqkptq smhqenltgh crepppwkhe<br>dskriyhfve gqsvhyecip gykalqrgpa isickmkcgk tgwtqpqltc<br>vderehhrfl aseesqgsrn sspesetscp itttdfpqpt ettamtetfv<br>ltmeykvava sclfllisil llsgltwqhr wrksrrti |
| 10 | AA | Mouse | Mature form of IL-2Rα extracellular domain | elclydppe vpnatfkals ykngtilnce ckrgfrrlke lvymrclgns wssncqctsn<br>shdksrkqvt aqlehqkeqq tttdmqkptq smhqenltgh crepppwkhe<br>dskriyhfve gqsvhyecip gykalqrgpa isickmkcgk tgwtqpqltc<br>vderehhrfl aseesqgsrn sspesetscp itttdfpqpt ettamtetfv ltmeyk |
| 11 | AA | | (Gly3Ser)4 linker | GGGSGGGSGGGSGGGS |
| 12 | AA | | (Gly3Ser)2 linker | GGGSGGGS |
| 13 | AA | | (Gly3Ser)3 linker | GGGSGGGSGGGS |
| 14 | AA | | (Gly3Ser)5 linker | GGGSGGGSGGGSGGGSGGGS |
| 15 | AA | | Gly3 linker | GGG |
| 16 | AA | Mouse | Mature form of IL-2 (Gly4Ser)4-extracellular domain of IL-2 Rα | APTSSSTSSSTAEAQQQQQQQQQQQQHLEQLLMDLQELLSRMENYRN<br>LKLPRMLTFKFYLPKQATELKDLQCLEDELGPLRHVLDLTQSKSFQLEDAE<br>NFISNIRVTVVKLKGSDNTFECQFDDESATVVDFLRRWIAFCQSIISTSPQ<br>GGGGSGGGGSGGGGSGGGGSELCLYDPPEVPNATFKALSYKNGTILNC<br>ECKRGFRRLKELVYMRCLGNSWSSNCQCTSNSHDKSRKQVTAQLEHQK<br>EQQTTTDMQKPTQSMHQENLTGHCREPPPWKHEDSKRIYHFVEGQSV<br>HYECIPGYKALQRGPAISICKMKCGKTGWTQPQLTCVDEREHHRFLASE<br>ESQGSRNSSPESETSCPITTTDFPQPTETTAMTETFVLTMEYK |
| 17 | AA | Mouse | Unprocessed form of IL-2 (Gly4Ser)4-extracellular domain of IL-2 Rα | MDSMQLASCVTLTLVLLVNSAPTSSSTSSSTAEAQQQQQQQQQQQQH<br>LEQLLMDLQELLSRMENYRNLKLPRMLTFKFYLPKQATELKDLQCLEDEL<br>GPLRHVLDLTQSKSFQLEDAENFISNIRVTVVKLKGSDNTFECQFDDESA<br>TVVDFLRRWIAFCQSIISTSPQGGGGSGGGGSGGGGSGGGGSELCLYDP<br>PEVPNATFKALSYKNGTILNCECKRGFRRLKELVYMRCLGNSWSSNCQC<br>TSNSHDKSRKQVTAQLEHQKEQQTTTDMQKPTQSMHQENLTGHCRE<br>PPPWKHEDSKRIYHFVEGQSVHYECIPGYKALQRGPAISICKMKCGKTG<br>WTQPQLTCVDEREHHRFLASEESQGSRNSSPESETSCPITTTDFPQPTET<br>TAMTETFVLTMEYK |
| 18 | AA | Mouse | Mature form of IL-2 (Gly4Ser)5-extracellular domain of IL-2 Rα | APTSSSTSSSTAEAQQQQQQQQQQQQHLEQLLMDLQELLSRMENYRN<br>LKLPRMLTFKFYLPKQATELKDLQCLEDELGPLRHVLDLTQSKSFQLEDAE<br>NFISNIRVTVVKLKGSDNTFECQFDDESATVVDFLRRWIAFCQSIISTSPQ<br>GGGGSGGGGSGGGGSGGGGSGGGGSELCLYDPPEVPNATFKALSYKN<br>GTILNCECKRGFRRLKELVYMRCLGNSWSSNCQCTSNSHDKSRKQVTA<br>QLEHQKEQQTTTDMQKPTQSMHQENLTGHCREPPPWKHEDSKRIYHF<br>VEGQSVHYECIPGYKALQRGPAISICKMKCGKTGWTQPQLTCVDEREH<br>HRFLASEESQGSRNSSPESETSCPITTTDFPQPTETTAMTETFVLTMEYK |
| 19 | AA | Mouse | Unprocessed form of IL-2 (Gly4Ser)5-extracellular domain of IL-2 Rα | MDSMQLASCVTLTLVLLVNSAPTSSSTSSSTAEAQQQQQQQQQQQQH<br>LEQLLMDLQELLSRMENYRNLKLPRMLTFKFYLPKQATELKDLQCLEDEL<br>GPLRHVLDLTQSKSFQLEDAENFISNIRVTVVKLKGSDNTFECQFDDESA<br>TVVDFLRRWIAFCQSIISTSPQGGGGSGGGGSGGGGSGGGGSGGGGSE<br>LCLYDPPEVPNATFKALSYKNGTILNCECKRGFRRLKELVYMRCLGNSWS<br>SNCQCTSNSHDKSRKQVTAQLEHQKEQQTTTDMQKPTQSMHQENLT<br>GHCREPPPWKHEDSKRIYHFVEGQSVHYECIPGYKALQRGPAISICKMKC<br>GKTGWTQPQLTCVDEREHHRFLASEESQGSRNSSPESETSCPITTTDFPQ<br>PTETTAMTETFVLTMEYK |
| 20 | AA | Mouse | Mature form of IL-2 (Gly3Ser)4-extracellular domain of IL-2 Rα | APTSSSTSSSTAEAQQQQQQQQQQQQHLEQLLMDLQELLSRMENYRN<br>LKLPRMLTFKFYLPKQATELKDLQCLEDELGPLRHVLDLTQSKSFQLEDAE<br>NFISNIRVTVVKLKGSDNTFECQFDDESATVVDFLRRWIAFCQSIISTSPQ<br>GGGSGGGSGGGSGGGSELCLYDPPEVPNATFKALSYKNGTILNCECKRG<br>FRRLKELVYMRCLGNSWSSNCQCTSNSHDKSRKQVTAQLEHQKEQQTT<br>TDMQKPTQSMHQENLTGHCREPPPWKHEDSKRIYHFVEGQSVHYECIP<br>GYKALQRGPAISICKMKCGKTGWTQPQLTCVDEREHHRFLASEESQGSR<br>NSSPESETSCPITTTDFPQPTETTAMTETFVLTMEYK |

TABLE 1-continued

Summary of Sequences

| SEQ ID NO | AA/NT | Source | Description | |
|---|---|---|---|---|
| 21 | AA | Mouse | Unprocessed form of IL-2 (Gly3Ser)4-extracellular domain of IL-2 Rα | MDSMQLASCVTLTLVLLVNSAPTSSSTSSSTAEAQQQQQQQQQQQQH LEQQLLMDLQELLSRMENYRNLKLPRMLTFKFYLPKQATELKDLQCLEDEL GPLRHVLDLTQSKSFQLEDAENFISNIRVTVVKLKGSDNTFECQFDDESA TVVDFLRRWIAFCQSIISTSPQGGGSGGGSGGGSGGGSELCLYDPPEVP NATFKALSYKNGTILNCECKRGFRRLKELVYMRCLGNSWSSNCQCTSNS HDKSRKQVTAQLEHQKEQQTTTDMQKPTQSMHQENLTGHCREPPPW KHEDSKRIYHFVEGQSVHYECIPGYKALQRGPAISICKMKCGKTGWTQP QLTCVDEREHHRFLASEESQGSRNSSPESETSCPITTTDFPQPTETTAMTE TFVLTMEYK |
| 22 | AA | human | Mature form IL-2 (Gly4Ser)4-extracellular domain of IL-2 Rα | APTSSSTKKTQLQLEHLLLDLQMILNGINNYKNPKLTRMLTFKFYMPKKA TELKHLQCLEEELKPLEEVLNLAQSKNFHLRPRDLISNINVIVLELKGSETTF MCEYADETATIVEFLNRWITFCQSIISTLTGGGGSGGGGSGGGGSGGGG SELCDDDPPEIPHATFKAMAYKEGTMLNCECKRGFRRIKSGSLYMLCTG NSSHSSWDNQCQCTSSATRNTTKQVTPQPEEQKERKTTEMQSPMQPV DQASLPGHCREPPPWENEATERIYHFVVGQMVYYQCVQGYRALHRGP AESVCKMTHGKTRWTQPQLICTGEMETSQFPGEEKPQASPEGRPESET SCLVTTTDFQIQTEMAATMETSIFTTEYQ |
| 23 | AA | Human | Unprocessed form IL-2 (Gly4Ser)4-extracellular domain of IL-2 Rα | MDRMQLLSCIALSLALVTNSAPTSSSTKKTQLQLEHLLLDLQMILNGINN YKNPKLTRMLTFKFYMPKKATELKHLQCLEEELKPLEEVLNLAQSKNFHL RPRDLISNINVIVLELKGSETTFMCEYADETATIVEFLNRWITFCQSIISTLT GGGGSGGGGSGGGGSGGGGSELCDDDPPEIPHATFKAMAYKEGTML NCECKRGFRRIKSGSLYMLCTGNSSHSSWDNQCQCTSSATRNTTKQVT PQPEEQKERKTTEMQSPMQPVDQASLPGHCREPPPWENEATERIYHFV VGQMVYYQCVQGYRALHRGPAESVCKMTHGKTRWTQPQLICTGEME TSQFPGEEKPQASPEGRPESETSCLVTTTDFQIQTEMAATMETSIFTTEY Q |
| 24 | AA | Human | Mature form IL-2 (Gly3Ser)4-extracellular domain of IL-2 Rα | APTSSSTKKTQLQLEHLLLDLQMILNGINNYKNPKLTRMLTFKFYMPKKA TELKHLQCLEEELKPLEEVLNLAQSKNFHLRPRDLISNINVIVLELKGSETTF MCEYADETATIVEFLNRWITFCQSIISTLTGGGSGGGSGGGSGGGSELCD DDPPEIPHATFKAMAYKEGTMLNCECKRGFRRIKSGSLYMLCTGNSSHS SWDNQCQCTSSATRNTTKQVTPQPEEQKERKTTEMQSPMQPVDQAS LPGHCREPPPWENEATERIYHFVVGQMVYYQCVQGYRALHRGPAESVC KMTHGKTRWTQPQLICTGEMETSQFPGEEKPQASPEGRPESETSCLVTT TDFQIQTEMAATMETSIFTTEYQ |
| 25 | AA | Human | Unprocessed form IL-2 (Gly3Ser)4-extracellular domain of IL-2 Rα | MDRMQLLSCIALSLALVTNSAPTSSSTKKTQLQLEHLLLDLQMILNGINN YKNPKLTRMLTFKFYMPKKATELKHLQCLEEELKPLEEVLNLAQSKNFHL RPRDLISNINVIVLELKGSETTFMCEYADETATIVEFLNRWITFCQSIISTLT GGGSGGGSGGGSGGGSELCDDDPPEIPHATFKAMAYKEGTMLNCECK RGFRRIKSGSLYMLCTGNSSHSSWDNQCQCTSSATRNTTKQVTPQPEE QKERKTTEMQSPMQPVDQASLPGHCREPPPWENEATERIYHFVVGQ MVYYQCVQGYRALHRGPAESVCKMTHGKTRWTQPQLICTGEMETSQF PGEEKPQASPEGRPESETSCLVTTTDFQIQTEMAATMETSIFTTEYQ |
| 26 | AA | Human | Mature form IL-2 (Gly3Ser)3-extracellular domain of IL-2 Rα | APTSSSTKKTQLQLEHLLLDLQMILNGINNYKNPKLTRMLTFKFYMPKKA TELKHLQCLEEELKPLEEVLNLAQSKNFHLRPRDLISNINVIVLELKGSETTF MCEYADETATIVEFLNRWITFCQSIISTLTGGGSGGGSGGGSELCDDDPP EIPHATFKAMAYKEGTMLNCECKRGFRRIKSGSLYMLCTGNSSHSSWD NQCQCTSSATRNTTKQVTPQPEEQKERKTTEMQSPMQPVDQASLPGH CREPPPWENEATERIYHFVVGQMVYYQCVQGYRALHRGPAESVCKMT HGKTRWTQPQLICTGEMETSQFPGEEKPQASPEGRPESETSCLVTTTDF QIQTEMAATMETSIFTTEYQ |
| 27 | AA | Human | Unprocessed form of IL-2 (Gly3Ser)3-extracellular domain of IL-2 Rα | MDRMQLLSCIALSLALVTNSAPTSSSTKKTQLQLEHLLLDLQMILNGINN YKNPKLTRMLTFKFYMPKKATELKHLQCLEEELKPLEEVLNLAQSKNFHL RPRDLISNINVIVLELKGSETTFMCEYADETATIVEFLNRWITFCQSIISTLT GGGSGGGSGGGSELCDDDPPEIPHATFKAMAYKEGTMLNCECKRGFRR IKSGSLYMLCTGNSSHSSWDNQCQCTSSATRNTTKQVTPQPEEQKERKT TEMQSPMQPVDQASLPGHCREPPPWENEATERIYHFVVGQMVYYQC VQGYRALHRGPAESVCKMTHGKTRWTQPQLICTGEMETSQFPGEEKP QASPEGRPESETSCLVTTTDFQIQTEMAATMETSIFTTEYQ |
| 28 | NT | human | IL-2 leader optimized Kozak sequence | gccaccATGGACAGGATGCAACTCCTGTCTTGCATTGCACTAAGTCTTG CACTTGTCACAAACAGT |

TABLE 1-continued

Summary of Sequences

| SEQ ID NO | AA/ NT | Source | Description | |
|---|---|---|---|---|
| 29 | NT | Mouse | Unprocessed form of IL-2 (Gly4Ser)4- extracellular domain of IL-2 Rα | ATGGACAGCATGCAGCTCGCATCCTGTGTCACATTGACACTTGTGCTC CTTGTCAACAGCGCACCCACTTCAAGCTCTACTTCAAGCTCTACAGCG GAAGCACAGCAGCAGCAGCAGCAGCAGCAGCAGCAGCAGCACCTGG AGCAGCTGTTGATGGACCTACAGGAGCTCCTGAGCAGGATGGAGAA TTACAGGAACCTGAAACTCCCCAGGATGCTCACCTTCAAATTTTACTT GCCCAAGCAGGCCACAGAATTGAAAGATCTTCAGTGCCTAGAAGATG AACTTGGACCTCTGCGGCATGTTCTGGATTTGACTCAAAGCAAAAGC TTTCAATTGGAAGATGCTGAGAATTTCATCAGCAATATCAGAGTAACT GTTGTAAAACTAAAGGGCTCTGACAACACATTTGAGTGCCAATTCGA TGATGAGTCAGCAACTGTGGTGGACTTTCTGAGGAGATGGATAGCCT TCTGTCAAAGCATCATCTCAACAAGCCCTCAAggtggaggtggatctggtgg aggtggatcaggtggaggtggatccggtggaggtggatctGAACTGTGTCTGTATG ACCCACCCGAGGTCCCCAATGCCACATTCAAAGCCCTCTCCTACAAGA ACGGCACCATCCTAAACTGTGAATGCAAGAGAGGTTTCCGAAGACTA AAGGAATTGGTCTATATGCGTTGCTTAGGAAACTCCTGGAGCAGCAA CTGCCAGTGCACCAGCAACTCCCATGACAAATCGAGAAAGCAAGTTA CAGCTCAACTTGAACACCAGAAAGAGCAACAAACCACAACAGACATG CAGAAGCCAACACAGTCTATGCACCAAGAGAACCTTACAGGTCACTG CAGGGAGCCACCTCCTTGGAAACATGAAGATTCCAAGAGAATCTATC ATTTCGTGGAAGGACAGAGTGTTCACTACGAGTGTATTCCGGGATAC AAGGCTCTACAGAGAGGTCCTGCTATTAGCATCTGCAAGATGAAGTG TGGGAAAACGGGGTGGACTCAGCCCCAGCTCACATGTGTAGATGAA AGAGAACACCACCGATTTCTGGCTAGTGAGGAATCTCAAGGAAGCA GAAATTCTTCTCCCGAGAGTGAGACTTCCTGCCCCATAACCACCACAG ACTTCCCACAACCCACAGAAACAACTGCAATGACGGAGACATTTGTG CTCACAATGGAGTATAAGGGTGGACATCACCATCACCATCACTAATA A |
| 30 | NT | Mouse | Unprocessed form of IL-2 (Gly3Ser)4- extracellular domain of IL-2 Rα | ATGGACAGCATGCAGCTCGCATCCTGTGTCACATTGACACTTGTGCTC CTTGTCAACAGCGCACCCACTTCAAGCTCTACTTCAAGCTCTACAGCG GAAGCACAGCAGCAGCAGCAGCAGCAGCAGCAGCAGCAGCACCTGG AGCAGCTGTTGATGGACCTACAGGAGCTCCTGAGCAGGATGGAGAA TTACAGGAACCTGAAACTCCCCAGGATGCTCACCTTCAAATTTTACTT GCCCAAGCAGGCCACAGAATTGAAAGATCTTCAGTGCCTAGAAGATG AACTTGGACCTCTGCGGCATGTTCTGGATTTGACTCAAAGCAAAAGC TTTCAATTGGAAGATGCTGAGAATTTCATCAGCAATATCAGAGTAACT GTTGTAAAACTAAAGGGCTCTGACAACACATTTGAGTGCCAATTCGA TGATGAGTCAGCAACTGTGGTGGACTTTCTGAGGAGATGGATAGCCT TCTGTCAAAGCATCATCTCAACAAGCCCTCAAggtggaggttctggtggaggt tcaggtggaggttcgggtggaggttctGAACTGTGTCTGTATGACCCACCCGAG GTCCCCAATGCCACATTCAAAGCCCTCTCCTACAAGAACGGCACCATC CTAAACTGTGAATGCAAGAGAGGTTTCCGAAGACTAAAGGAATTGGT CTATATGCGTTGCTTAGGAAACTCCTGGAGCAGCAACTGCCAGTGCA CCAGCAACTCCCATGACAAATCGAGAAAGCAAGTTACAGCTCAACTT GAACACCAGAAAGAGCAACAAACCACAACAGACATGCAGAAGCCAA CACAGTCTATGCACCAAGAGAACCTTACAGGTCACTGCAGGGAGCCA CCTCCTTGGAAACATGAAGATTCCAAGAGAATCTATCATTTCGTGGAA GGACAGAGTGTTCACTACGAGTGTATTCCGGGATACAAGGCTCTACA GAGAGGTCCTGCTATTAGCATCTGCAAGATGAAGTGTGGGAAAACG GGGTGGACTCAGCCCCAGCTCACATGTGTAGATGAAAGAGAACACC ACCGATTTCTGGCTAGTGAGGAATCTCAAGGAAGCAGAAATTCTTCT CCCGAGAGTGAGACTTCCTGCCCCATAACCACCACAGACTTCCCACAA CCCACAGAAACAACTGCAATGACGGAGACATTTGTGCTCACAATGGA GTATAAGGGTGGACATCACCATCACCATCACTAATAA |
| 31 | NT | Mouse | Unprocessed form of IL-2 (Gly4Ser)5 - extracellular domain of IL-2 Rα | ATGGACAGCATGCAGCTCGCATCCTGTGTCACATTGACACTTGTGCTC CTTGTCAACAGCGCACCCACTTCAAGCTCTACTTCAAGCTCTACAGCG GAAGCACAGCAGCAGCAGCAGCAGCAGCAGCAGCAGCAGCACCTGG AGCAGCTGTTGATGGACCTACAGGAGCTCCTGAGCAGGATGGAGAA TTACAGGAACCTGAAACTCCCCAGGATGCTCACCTTCAAATTTTACTT GCCCAAGCAGGCCACAGAATTGAAAGATCTTCAGTGCCTAGAAGATG AACTTGGACCTCTGCGGCATGTTCTGGATTTGACTCAAAGCAAAAGC TTTCAATTGGAAGATGCTGAGAATTTCATCAGCAATATCAGAGTAACT GTTGTAAAACTAAAGGGCTCTGACAACACATTTGAGTGCCAATTCGA TGATGAGTCAGCAACTGTGGTGGACTTTCTGAGGAGATGGATAGCCT TCTGTCAAAGCATCATCTCAACAAGCCCTCAAggtggaggtggatcaggtgg aggtggatctggtggaggtggatcaggtggaggtggatccggtggaggtggatctGAAC TGTGTCTGTATGACCCACCCGAGGTCCCCAATGCCACATTCAAAGCCC TCTCCTACAAGAACGGCACCATCCTAAACTGTGAATGCAAGAGAGGT TTCCGAAGACTAAAGGAATTGGTCTATATGCGTTGCTTAGGAAACTC CTGGAGCAGCAACTGCCAGTGCACCAGCAACTCCCATGACAAATCGA GAAAGCAAGTTACAGCTCAACTTGAACACCAGAAAGAGCAACAAACC ACAACAGACATGCAGAAGCCAACACAGTCTATGCACCAAGAGAACCT TACAGGTCACTGCAGGGAGCCACCTCCTTGGAAACATGAAGATTCCA |

TABLE 1-continued

Summary of Sequences

| SEQ ID NO | AA/NT | Source | Description | |
|---|---|---|---|---|
| | | | | AGAGAATCTATCATTTCGTGGAAGGACAGAGTGTTCACTACGAGTGT<br>ATTCCGGGATACAAGGCTCTACAGAGAGGTCCTGCTATTAGCATCTG<br>CAAGATGAAGTGTGGGAAAACGGGGTGGACTCAGCCCCAGCTCACA<br>TGTGTAGATGAAAGAGAACACCACCGATTTCTGGCTAGTGAGGAATC<br>TCAAGGAAGCAGAAATTCTTCTCCCGAGAGTGAGACTTCCTGCCCCA<br>TAACCACCACAGACTTCCCACAACCCACAGAAACAACTGCAATGACG<br>GAGACATTTGTGCTCACAATGGAGTATAAGGGTGGACATCACCATCA<br>CCATCACTAATAA |
| 32 | NT | Human | Unprocessed form IL-2 (Gly4Ser)4-extracellular domain of IL-2 Rα | ATGGACAGGATGCAACTCCTGTCTTGCATTGCACTAAGTCTTGCACTT<br>GTCACAAACAGTGCACCTACTTCAAGTTCTACAAAGAAAACACAGCT<br>ACAACTGGAGCATTTACTGCTGGATTTACAGATGATTTTGAATGGAAT<br>TAATAATTACAAGAATCCCAAACTCACCAGGATGCTCACATTTAAGTT<br>TTACATGCCCAAGAAGGCCACAGAACTGAAACATCTTCAGTGTCTAG<br>AAGAAGAACTCAAACCTCTGGAGGAAGTGCTAAATTTAGCTCAAAGC<br>AAAAACTTTCACTTAAGACCCAGGGACTTAATCAGCAATATCAACGTA<br>ATAGTTCTGGAACTAAAGGGATCTGAAACAACATTCATGTGTGAATA<br>TGCTGATGAGACAGCAACCATTGTAGAATTTCTGAACAGATGGATTA<br>CCTTTTGTCAAAGCATCATCTCAACACTGACTggtggaggtggatctggtgga<br>ggtggatcaggtggaggtggatccggtggaggtggatct<br>GAGCTCTGTGACGATGACCCGCCAGAGATCCCACACGCCACATTCAA<br>AGCCATGGCCTACAAGGAAGGAACCATGTTGAACTGTGAATGCAAG<br>AGAGGTTTCCGCAGAATAAAAAGCGGGTCACTCTATATGCTCTGTAC<br>AGGAAACTCTAGCCACTCGTCCTGGGACAACCAATGTCAATGCACAA<br>GCTCTGCCACTCGGAACACAACGAAACAAGTGACACCTCAACCTGAA<br>GAACAGAAAGAAAGGAAAACCACAGAAATGCAAAGTCCAATGCAGC<br>CAGTGGACCAAGCGAGCCTTCCAGGTCACTGCAGGGAACCTCCACCA<br>TGGGAAAATGAAGCCACAGAGAGAATTTATCATTTCGTGGTGGGGC<br>AGATGGTTTATTATCAGTGCGTCCAGGGATACAGGGCTCTACACAGA<br>GGTCCTGCTGAGAGCGTCTGCAAAATGACCCACGGGAAGACAAGGT<br>GGGACCCAGCCCCAGCTCATATGCACAGGTGAAATGGAGACCAGTCA<br>GTTTCCAGGTGAAGAGAAGCCTCAGGCAAGCCCCGAAGGCCGTCCT<br>GAGAGTGAGACTTCCTGCCTCGTCACAACAACAGATTTTCAAATACA<br>GACAGAAATGGCTGCAACCATGGAGACGTCCATATTTACAACAGAGT<br>ACCAGGGTGGACATCACCATCACCATCACTAATAA |
| 33 | NT | Human | Unprocessed form IL-2 (Gly3Ser)4-extracellular domain of IL-2 Rα | ATGGACAGGATGCAACTCCTGTCTTGCATTGCACTAAGTCTTGCACTT<br>GTCACAAACAGTGCACCTACTTCAAGTTCTACAAAGAAAACACAGCT<br>ACAACTGGAGCATTTACTGCTGGATTTACAGATGATTTTGAATGGAAT<br>TAATAATTACAAGAATCCCAAACTCACCAGGATGCTCACATTTAAGTT<br>TTACATGCCCAAGAAGGCCACAGAACTGAAACATCTTCAGTGTCTAG<br>AAGAAGAACTCAAACCTCTGGAGGAAGTGCTAAATTTAGCTCAAAGC<br>AAAAACTTTCACTTAAGACCCAGGGACTTAATCAGCAATATCAACGTA<br>ATAGTTCTGGAACTAAAGGGATCTGAAACAACATTCATGTGTGAATA<br>TGCTGATGAGACAGCAACCATTGTAGAATTTCTGAACAGATGGATTA<br>CCTTTTGTCAAAGCATCATCTCAACACTGACTggtggaggttctggtggaggt<br>tcaggtggaggttcgggtggaggttctGAGCTCTGTGACGATGACCCGCCAGA<br>GATCCCACACGCCACATTCAAAGCCATGGCCTACAAGGAAGGAACCA<br>TGTTGAACTGTGAATGCAAGAGAGGTTTCCGCAGAATAAAAAGCGG<br>GTCACTCTATATGCTCTGTACAGGAAACTCTAGCCACTCGTCCTGGGA<br>CAACCAATGTCAATGCACAAGCTCTGCCACTCGGAACACAACGAAAC<br>AAGTGACACCTCAACCTGAAGAACAGAAAGAAAGGAAAACCACAGA<br>AATGCAAAGTCCAATGCAGCCAGTGGACCAAGCGAGCCTTCCAGGTC<br>ACTGCAGGGAACCTCCACCATGGGAAAATGAAGCCACAGAGAGAAT<br>TTATCATTTCGTGGTGGGCAGATGGTTTATTATCAGTGCGTCCAGG<br>GATACAGGGCTCTACACAGAGGTCCTGCTGAGAGCGTCTGCAAAATG<br>ACCCACGGGAAGACAAGGTGGACCCAGCCCCAGCTCATATGCACAG<br>GTGAAATGGAGACCAGTCAGTTTCCAGGTGAAGAGAAGCCTCAGGC<br>AAGCCCCGAAGGCCGTCCTGAGAGTGAGACTTCCTGCCTCGTCACAA<br>CAACAGATTTTCAAATACAGACAGAAATGGCTGCAACCATGGAGACG<br>TCCATATTTACAACAGAGTACCAGGGTGGACATCACCATCACCATCAC<br>TAATAA |
| 34 | NT | Human | Unprocessed form of IL-2 (Gly3Ser)3-extracellular domain of IL-2 Rα | ATGGACAGGATGCAACTCCTGTCTTGCATTGCACTAAGTCTTGCACTT<br>GTCACAAACAGTGCACCTACTTCAAGTTCTACAAAGAAAACACAGCT<br>ACAACTGGAGCATTTACTGCTGGATTTACAGATGATTTTGAATGGAAT<br>TAATAATTACAAGAATCCCAAACTCACCAGGATGCTCACATTTAAGTT<br>TTACATGCCCAAGAAGGCCACAGAACTGAAACATCTTCAGTGTCTAG<br>AAGAAGAACTCAAACCTCTGGAGGAAGTGCTAAATTTAGCTCAAAGC<br>AAAAACTTTCACTTAAGACCCAGGGACTTAATCAGCAATATCAACGTA<br>ATAGTTCTGGAACTAAAGGGATCTGAAACAACATTCATGTGTGAATA<br>TGCTGATGAGACAGCAACCATTGTAGAATTTCTGAACAGATGGATTA<br>CCTTTTGTCAAAGCATCATCTCAACACTGACTggtggaggttctggtggaggt<br>tcaggtggaggttcgGAGCTCTGTGACGATGACCCGCCAGAGATCCCACA |

TABLE 1-continued

Summary of Sequences

| SEQ ID NO | AA/NT | Source | Description | |
|---|---|---|---|---|
| | | | | CGCCACATTCAAAGCCATGGCCTACAAGGAAGGAACCATGTTGAACT GTGAATGCAAGAGAGGTTTCCGCAGAATAAAAAGCGGGTCACTCTAT ATGCTCTGTACAGGAAACTCTAGCCACTCGTCCTGGGACAACCAATG TCAATGCACAAGCTCTGCCACTCGGAACACAACGAAACAAGTGACAC CTCAACCTGAAGAACAGAAAGAAAGGAAAACCACAGAAATGCAAAG TCCAATGCAGCCAGTGGACCAAGCGAGCCTTCCAGGTCACTGCAGGG AACCTCCACCATGGGAAAATGAAGCCACAGAGAGAATTTATCATTTC GTGGTGGGGCAGATGGTTTATTATCAGTGCGTCCAGGGATACAGGG CTCTACACAGAGGTCCTGCTGAGAGCGTCTGCAAAATGACCCACGGG AAGACAAGGTGGACCCAGCCCCAGCTCATATGCACAGGTGAAATGG AGACCAGTCAGTTTCCAGGTGAAGAGAAGCCTCAGGCAAGCCCCGA AGGCCGTCCTGAGAGTGAGACTTCCTGCCTCGTCACAACAACAGATT TTCAAATACAGACAGAAATGGCTGCAACCATGGAGACGTCCATATTT ACAACAGAGTACCAGGGTGGACATCACCATCACCATCACTAATAA |
| 35 | NT | | Kozak consensus | (gcc)gccRccAUGG |
| 36 | AA | Mouse | unprocessed form of IL-2 (Gly3Ser)3- extracellular domain of IL-2 Rα | MYSMQLASCVTLTLVLLVNSAPTSSSTSSSTAEAQQQQQQQQQQQQH LEQLLMDLQELLSRMENYRNLKLPRMLTFKFYLPKQATELKDLQCLEDEL GPLRHVLDLTQSKSFQLEDAENFISNIRVTVVKLKGSDNTFECQFDDESA TVVDFLRRWIAFCQSIISTSPQGGGSGGGSGGGSELCLYDPPEVPNATFK ALSYKNGTILNCECKRGFRRLKELVYMRCLGNSWSSNCQCTSNSHDKSR KQVTAQLEHQKEQQTTTDMQKPTQSMHQENLTGHCREPPPWKHEDS KRIYHFVEGQSVHYECIPGYKALQRGPAISICKMKCGKTGWTQPQLTC VDEREHHRFLASEESQGSRNSSPESETSCPITTTDFPQPTETTAMTETFVL TMEYK |
| 37 | AA | Mouse | Mature form of IL-2 (Gly3Ser)3- extracellular domain of IL-2 Rα | MDSMQLASCVTLTLVLLVNSAPTSSSTSSSTAEAQQQQQQQQQQQQH LEQLLMDLQELLSRMENYRNLKLPRMLTFKFYLPKQATELKDLQCLEDEL GPLRHVLDLTQSKSFQLEDAENFISNIRVTVVKLKGSDNTFECQFDDESA TVVDFLRRWIAFCQSIISTSPQGGGSGGGSGGGSELCLYDPPEVPNATFK ALSYKNGTILNCECKRGFRRLKELVYMRCLGNSWSSNCQCTSNSHDKSR KQVTAQLEHQKEQQTTTDMQKPTQSMHQENLTGHCREPPPWKHEDS KRIYHFVEGQSVHYECIPGYKALQRGPAISICKMKCGKTGWTQPQLTCV DEREHHRFLASEESQGSRNSSPESETSCPITTTDFPQPTETTAMTETFVLT MEYK |
| 38 | AA | Human | unprocessed form of IL-2 (Gly4Ser)5- extracellular domain of IL-2 Rα | MDRMQLLSCIALSLALVTNSAPTSSSTKKTQLQLEHLLLDLQMILNGINN YKNPKLTRMLTFKFYMPKKATELKHLQCLEEELKPLEEVLNLAQSKNFHL RPRDLISNINVIVLELKGSETTFMCEYADETATIVEFLNRWITFCQSIISTLT GGGGSGGGGSGGGGSGGGGSGGGGSELCDDDPPEIPHATFKAMAYK EGTMLNCECKRGFRRIKSGSLYMLCTGNSSHSSWDNQCQCTSSATRNT TKQVTPQPEEQKERKTTEMQSPMQPVDQASLPGHCREPPPWENEATE RIYHFVVGQMVYYQCVQGYRALHRGPAESVCKMTHGKTRWTQPQLIC TGEMETSQFPGEEKPQASPEGRPESETSCLVTTTDFQIQTEMAATMETS IFTTEYQ |
| 39 | AA | human | Mature form of human IL-2 (Gly4Ser)5- extracellular domain of IL-2 Rα | APTSSSTKKTQLQLEHLLLDLQMILNGINNYKNPKLTRMLTFKFYMPKKA TELKHLQCLEEELKPLEEVLNLAQSKNFHLRPRDLISNINVIVLELKGSETTF MCEYADETATIVEFLNRWITFCQSIISTLTGGGGSGGGGSGGGGSGGGG SGGGGSELCDDDPPEIPHATFKAMAYKEGTMLNCECKRGFRRIKSGSLY MLCTGNSSHSSWDNQCQCTSSATRNTTKQVTPQPEEQKERKTTEMQS PMQPVDQASLPGHCREPPPWENEATERIYHFVVGQMVYYQCVQGYR ALHRGPAESVCKMTHGKTRWTQPQLICTGEMETSQFPGEEKPQASPEG RPESETSCLVTTTDFQIQTEMAATMETSIFTTEYQ |
| 40 | AA | | Linker sequence (Gly4Ser)4 | GGGGSGGGGSGGGGSGGGGS |
| 41 | AA | | Linker sequence (Gly4Ser)5 | GGGGSGGGGSGGGGSGGGGSGGGGS |
| 42 | NT | mouse | Unprocessed form IL-2 (Gly3Ser)3- extracellular domain of IL-2 Rα | ATGGACAGCATGCAGCTCGCATCCTGTGTCACATTGACACTTGTGCTC CTTGTCAACAGCGCACCCACTTCAAGCTCTACTTCAAGCTCTACAGCG GAAGCACAGCAGCAGCAGCAGCAGCAGCAGCAGCAGCAGCACCTGG AGCAGCTGTTGATGGACCTACAGGAGCTCCTGAGCAGGATGGAGAA TTACAGGAACCTGAAACTCCCCAGGATGCTCACCTTCAAATTTTACTT GCCCAAGCAGGCCACAGAATTGAAAGATCTTCAGTGCCTAGAAGATG AACTTGGACCTCTGCGGCATGTTCTGGATTTGACTCAAAGCAAAAGC TTTCAATTGGAAGATGCTGAGAATTTCATCAGCAATATCAGAGTAACT GTTGTAAAACTAAAGGGCTCTGACAACACATTTGAGTGCCAATTCGA |

TABLE 1-continued

Summary of Sequences

| SEQ ID NO | AA/NT | Source | Description | |
|---|---|---|---|---|
| | | | | TGATGAGTCAGCAACTGTGGTGGACTTTCTGAGGAGATGGATAGCCT TCTGTCAAAGCATCATCTCAACAAGCCCTCAAGGTGGAGGTTCTGGT GGAGGTTCAGGTGGAGGTTCGGAACTGTGTCTGTATGACCCACCCGA GGTCCCCAATGCCACATTCAAAGCCCTCTCCTACAAGAACGGCACCAT CCTAAACTGTGAATGCAAGAGAGGTTTCCGAAGACTAAAGGAATTGG TCTATATGCGTTGCTTAGGAAACTCCTGGAGCAGCAACTGCCAGTGC ACCAGCAACTCCCATGACAAATCGAGAAAGCAAGTTACAGCTCAACT TGAACACCAGAAAGAGCAACAAACCACAACAGACATGCAGAAGCCA ACACAGTCTATGCACCAAGAGAACCTTACAGGTCACTGCAGGGAGCC ACCTCCTTGGAAACATGAAGATTCCAAGAGAATCTATCATTTCGTGGA AGGACAGAGTGTTCACTACGAGTGTATTCCGGGATACAAGGCTCTAC AGAGAGGTCCTGCTATTAGCATCTGCAAGATGAAGTGTGGGAAAAC GGGGTGGACTCAGCCCCAGCTCACATGTGTAGATGAAAGAGAACAC CACCGATTTCTGGCTAGTGAGGAATCTCAAGGAAGCAGAAATTCTTC TCCCGAGAGTGAGACTTCCTGCCCCATAACCACCACAGACTTCCCACA ACCCACAGAAACAACTGCAATGACGGAGACATTTGTGCTCACAATGG AGTATAAGGGTGGACATCACCATCACCATCACTAATAA |
| 43 | AA | Human | Mature form IL-2 (Gly3Ser)2-extracellular domain of IL-2 Rα | APTSSSTKKTQLQLEHLLLDLQMILNGINNYKNPKLTRMLTFKFYMPKKA TELKHLQCLEEELKPLEEVLNLAQSKNFHLRPRDLISNINVIVLELKGSETTF MCEYADETATIVEFLNRWITFCQSIISTLTGGGSGGGSELCDDDPPEIPHA TFKAMAYKEGTMLNCECKRGFRRIKSGSLYMLCTGNSSHSSWDNQCQC TSSSATRNTTKQVTPQPEEQKERKTTEMQSPMQPVDQASLPGHCREPPP WENEATERIYHFVVGQMVYYQCVQGYRALHRGPAESVCKMTHGKTR WTQPQLICTGEMETSQFPGEEKPQASPEGRPESETSCLVTTTDFQIQTE MAATMETSIFTTEYQ |
| 44 | AA | Human | Unprocessed form IL-2 (Gly3Ser)2-extracellular domain of IL-2 Rα | MDRMQLLSCIALSLALVTNSAPTSSSTKKTQLQLEHLLLDLQMILNGINN YKNPKLTRMLTFKFYMPKKATELKHLQCLEEELKPLEEVLNLAQSKNFHL RPRDLISNINVIVLELKGSETTFMCEYADETATIVEFLNRWITFCQSIISTLT GGGSGGGSELCDDDPPEIPHATFKAMAYKEGTMLNCECKRGFRRIKSGS LYMLCTGNSSHSSWDNQCQCTSSATRNTTKQVTPQPEEQKERKTTEM QSPMQPVDQASLPGHCREPPPWENEATERIYHFVVGQMVYYQCVQG YRALHRGPAESVCKMTHGKTRWTQPQLICTGEMETSQFPGEEKPQASP EGRPESETSCLVTTTDFQIQTEMAATMETSIFTTEYQ |
| 45 | AA | Human | Mature form IL-2 (Gly3)-extracellular domain of IL-2 Rα | APTSSSTKKTQLQLEHLLLDLQMILNGINNYKNPKLTRMLTFKFYMPKKA TELKHLQCLEEELKPLEEVLNLAQSKNFHLRPRDLISNINVIVLELKGSETTF MCEYADETATIVEFLNRWITFCQSIISTLTGGGELCDDDPPEIPHATFKA MAYKEGTMLNCECKRGFRRIKSGSLYMLCTGNSSHSSWDNQCQCTSSA TRNTTKQVTPQPEEQKERKTTEMQSPMQPVDQASLPGHCREPPPWEN EATERIYHFVVGQMVYYQCVQGYRALHRGPAESVCKMTHGKTRWTQP QLICTGEMETSQFPGEEKPQASPEGRPESETSCLVTTTDFQIQTEMAAT METSIFTTEYQ |
| 46 | AA | Human | Unprocessed form IL-2 (Gly3)-extracellular domain of IL-2 Rα | MDRMQLLSCIALSLALVTNSAPTSSSTKKTQLQLEHLLLDLQMILNGINN YKNPKLTRMLTFKFYMPKKATELKHLQCLEEELKPLEEVLNLAQSKNFHL RPRDLISNINVIVLELKGSETTFMCEYADETATIVEFLNRWITFCQSIISTLT GGGELCDDDPPEIPHATFKAMAYKEGTMLNCECKRGFRRIKSGSLYMLC TGNSSHSSWDNQCQCTSSATRNTTKQVTPQPEEQKERKTTEMQSPMQ PVDQASLPGHCREPPPWENEATERIYHFVVGQMVYYQCVQGYRALHR GPAESVCKMTHGKTRWTQPQLICTGEMETSQFPGEEKPQASPEGRPES ETSCLVTTTDFQIQTEMAATMETSIFTTEYQ |
| 47 | NT | Human | Unprocessed form IL-2 (Gly3Ser)2-extracellular domain of IL-2 Rα | ATGGACAGGATGCAACTCCTGTCTTGCATTGCACTAAGTCTTGCACTT GTCACAAACAGTGCACCTACTTCAAGTTCTACAAAGAAAACACAGCT ACAACTGGAGCATTTGCTGCTGGATTTACAGATGATTTTGAATGGAAT TAATAATTACAAGAATCCCAAACTCACCAGGATGCTCACATTTAAGTT TTACATGCCCAAGAAGGCCACAGAACTGAAACATCTTCAGTGTCTAG AAGAAGAACTCAAACCTCTGGAGGAAGTGCTAAATTTAGCTCAAAGC AAAAACTTTCACTTAAGACCCAGGGACTTAATCAGCAATATCAACGTA ATAGTTCTGGAACTAAAGGGATCTGAAACAACATTCATGTGTGAATA TGCTGATGAGACAGCAACCATTGTAGAATTTCTGAACAGATGATTA CCTTTTGTCAAAGCATCATCTCAACACTGACTggtggaggttctggtggaggt tcaGAGCTCTGTGACGATGACCCGCCAGAGATCCCACACGCCACATTC AAAGCCATGGCCTACAAGGAAGGAACCATGTTGAACTGTGAATGCA AGAGAGGTTTCCGCAGAATAAAAAGCGGGTCACTCTATATGCTCTGT ACAGGAAACTCTAGCCACTCGTCCTGGGACAACCAATGTCAATGCAC AAGCTCTGCCACTCGGAACTACAACGAAACAAGTGACACCTCAACCTG AAGAACAGAAAGAAAGGAAAACCACAGAAATGCAAAGTCCAATGCA GCCAGTGACCAAGCGAGCCTTCCAGGTCACTGCAGGGAACCTCCAC CATGGGAAAATGAAGCCACAGAGAGAATTTATCATTTCGTGGTGGG GCAGATGGTTTATTATCAGTGCGTCCAGGGATACAGGGCTCTACACA GAGGTCCTGCTGAGAGCGTCTGCAAAATGACCCACGGGAAGACAAG |

TABLE 1-continued

Summary of Sequences

| SEQ ID NO | AA/NT | Source | Description | |
|---|---|---|---|---|
| | | | | GTGGACCCAGCCCCAGCTCATATGCACAGGTGAAATGGAGACCAGTC AGTTTCCAGGTGAAGAGAAGCCTCAGGCAAGCCCCGAAGGCCGTCC TGAGAGTGAGACTTCCTGCCTCGTCACAACAACAGATTTTCAAATACA GACAGAAATGGCTGCAACCATGGAGACGTCCATATTTACAACAGAGT ACCAGGGTGGACATCACCATCACCATCACTAATAA |
| 48 | NT | Human | Unprocessed form IL-2 (Gly3)- extracellular domain of IL-2 Rα | ATGGACAGGATGCAACTCCTGTCTTGCATTGCACTAAGTCTTGCACTT GTCACAAACAGTGCACCTACTTCAAGTTCTACAAAGAAAACACAGCT ACAACTGGAGCATTTACTGCTGGATTTACAGATGATTTTGAATGGAAT TAATAATTACAAGAATCCCAAACTCACCAGGATGCTCACATTTAAGTT TTACATGCCCAAGAAGGCCACAGAACTGAAACATCTTCAGTGTCTAG AAGAAGAACTCAAACCTCTGGAGGAAGTGCTAAATTTAGCTCAAAGC AAAAACTTTCACTTAAGACCCAGGGACTTAATCAGCAATATCAACGTA ATAGTTCTGGAACTAAAGGGATCTGAAACAACATTCATGTGTGAATA TGCTGATGAGACAGCAACCATTGTAGAATTTCTGAACAGATGGATTA CCTTTTGTCAAAGCATCATCTCAACACTGACTggtggaggtGAGCTCTGT GACGATGACCCGCCAGAGATCCCACACGCCACATTCAAAGCCATGGC CTACAAGGAAGGAACCATGTTGAACTGTGAATGCAAGAGAGGTTTCC GCAGAATAAAAAGCGGGTCACTCTATATGCTCTGTACAGGAAACTCT AGCCACTCGTCCTGGGACAACCAATGTCAATGCACAAGCTCTGCCAC TCGGAACACAACGAAACAAGTGACACCTCAACCTGAAGAACAGAAA GAAAGGAAAACCACAGAAATGCAAAGTCCAATGCAGCCAGTGGACC AAGCGAGCCTTCCAGGTCACTGCAGGGAACCTCCACCATGGGAAAT GAAGCCACAGAGAGAATTTATCATTTCGTGGTGGGGCAGATGGTTTA TTATCAGTGCGTCCAGGGATACAGGGCTCTACACAGAGGTCCTGCTG AGAGCGTCTGCAAAATGACCCACGGGAAGACAAGGTGGACCCAGCC CCAGCTCATATGCACAGGTGAAATGGAGACCAGTCAGTTTCCAGGTG AAGAGAAGCCTCAGGCAAGCCCCGAAGGCCGTCCTGAGAGTGAGAC TTCCTGCCTCGTCACAACAACAGATTTTCAAATACAGACAGAAATGGC TGCAACCATGGAGACGTCCATATTTACAACAGAGTACCAGGGTGGAC ATCACCATCACCATCACTAATAA |
| 49 | NT | Human | Unprocessed form IL-2 (Gly4Ser)5- extracellular domain of IL-2 Rα | ATGGACAGGATGCAACTCCTGTCTTGCATTGCACTAAGTCTTGCACTT GTCACAAACAGTGCACCTACTTCAAGTTCTACAAAGAAAACACAGCT ACAACTGGAGCATTTACTGCTGGATTTACAGATGATTTTGAATGGAAT TAATAATTACAAGAATCCCAAACTCACCAGGATGCTCACATTTAAGTT TTACATGCCCAAGAAGGCCACAGAACTGAAACATCTTCAGTGTCTAG AAGAAGAACTCAAACCTCTGGAGGAAGTGCTAAATTTAGCTCAAAGC AAAAACTTTCACTTAAGACCCAGGGACTTAATCAGCAATATCAACGTA ATAGTTCTGGAACTAAAGGGATCTGAAACAACATTCATGTGTGAATA TGCTGATGAGACAGCAACCATTGTAGAATTTCTGAACAGATGGATTA CCTTTTGTCAAAGCATCATCTCAACACTGACTggtggaggtggatcaggtgga ggtggatctggtggaggtggatcaggtggaggtggatccggtggaggtggatctGAGCT CTGTGACGATGACCCGCCAGAGATCCCACACGCCACATTCAAAGCCA TGGCCTACAAGGAAGGAACCATGTTGAACTGTGAATGCAAGAGAGG TTTCCGCAGAATAAAAAGCGGGTCACTCTATATGCTCTGTACAGGAA ACTCTAGCCACTCGTCCTGGGACAACCAATGTCAATGCACAAGCTCTG CCACTCGGAACACAACGAAACAAGTGACACCTCAACCTGAAGAACAG AAAGAAAGGAAAACCACAGAAATGCAAAGTCCAATGCAGCCAGTGG ACCAAGCGAGCCTTCCAGGTCACTGCAGGGAACCTCCACCATGGGAA AATGAAGCCACAGAGAGAATTTATCATTTCGTGGTGGGGCAGATGGT TTATTATCAGTGCGTCCAGGGATACAGGGCTCTACACAGAGGTCCTG CTGAGAGCGTCTGCAAAATGACCCACGGGAAGACAAGGTGGACCCA GCCCCAGCTCATATGCACAGGTGAAATGGAGACCAGTCAGTTTCCAG GTGAAGAGAAGCCTCAGGCAAGCCCCGAAGGCCGTCCTGAGAGTGA GACTTCCTGCCTCGTCACAACAACAGATTTTCAAATACAGACAGAAAT GGCTGCAACCATGGAGACGTCCATATTTACAACAGAGTACCAGGGTG GACATCACCATCACCATCACTAATAA |
| 50 | AA | | (Gly4Ser)3 linker | GGGGSGGGGSGGGGS |
| 51 | AA | | (Gly4Ser)2 linker | GGGGSGGGGS |
| 52 | AA | | (Gly4Ser)1 linker | GGGGS |
| 53 | NT | | Kozak sequence | gccaccATGG |
| 54 | AA | Mouse | Unprocessed form of IL-2 (Gly4Ser)4- | MDSMQLASCVTLTLVLLVNSAPTSSSTSSSTAEAQQQQQQQQQQQQH LEQLLMDLQELLSRMENYRNLKLPRMLTFKFYLPKQATELKDLQCLEDEL GPLRHVLDLTQSKSFQLEDAENFISNIRVTVVKLKGSDNTFECQFDDESA |

TABLE 1-continued

Summary of Sequences

| SEQ ID NO | AA/NT | Source | Description | |
|---|---|---|---|---|
| | | | extracellular domain of IL-2 Rα + glycine spacer and poly-histidine region | TVVDFLRRWIAFCQSIISTSPQGGGGSGGGGSGGGGSGGGGSELCLYDP PEVPNATFKALSYKNGTILNCECKRGFRRLKELVYMRCLGNSWSSNCQC TSNSHDKSRKQVTAQLEHQKEQQTTTDMQKPTQSMHQENLTGHCRE PPPWKHEDSKRIYHFVEGQSVHYECIPGYKALQRGPAISICKMKCGKTG WTQPQLTCVDEREHHRFLASEESQGSRNSSPESETSCPITTTDFPQPTET TAMTETFVLTMEYKGGHHHHHH |
| 55 | AA | Mouse | Unprocessed form of IL-2 (Gly4Ser)5- extracellular domain of IL-2 Rα + glycine spacer and poly-histidine region | MDSMQLASCVTLTLVLLVNSAPTSSSTSSSTAEAQQQQQQQQQQQQH LEQLLMDLQELLSRMENYRNLKLPRMLTFKFYLPKQATELKDLQCLEDEL GPLRHVLDLTQSKSFQLEDAENFISNIRVTVVKLKGSDNTFECQFDDESA TVVDFLRRWIAFCQSIISTSPQGGGGSGGGGSGGGGSGGGGSGGGGSE LCLYDPPEVPNATFKALSYKNGTILNCECKRGFRRLKELVYMRCLGNSWS SNCQCTSNSHDKSRKQVTAQLEHQKEQQTTTDMQKPTQSMHQENLT GHCREPPPWKHEDSKRIYHFVEGQSVHYECIPGYKALQRGPAISICKMKC GKTGWTQPQLTCVDEREHHRFLASEESQGSRNSSPESETSCPITTTDFPQ PTETTAMTETFVLTMEYKGGHHHHHH |
| 56 | AA | Mouse | Unprocessed form of IL-2 (Gly3Ser)4- extracellular domain of IL-2 Rα + glycine spacer and poly-histidine region | MDSMQLASCVTLTLVLLVNSAPTSSSTSSSTAEAQQQQQQQQQQQQH LEQLLMDLQELLSRMENYRNLKLPRMLTFKFYLPKQATELKDLQCLEDEL GPLRHVLDLTQSKSFQLEDAENFISNIRVTVVKLKGSDNTFECQFDDESA TVVDFLRRWIAFCQSIISTSPQGGGSGGGSGGGSGGGSELCLYDPPEVP NATFKALSYKNGTILNCECKRGFRRLKELVYMRCLGNSWSSNCQCTSNS HDKSRKQVTAQLEHQKEQQTTTDMQKPTQSMHQENLTGHCREPPPW KHEDSKRIYHFVEGQSVHYECIPGYKALQRGPAISICKMKCGKTGWTQP QLTCVDEREHHRFLASEESQGSRNSSPESETSCPITTTDFPQPTETTAMTE TFVLTMEYKGGHHHHHH |
| 57 | AA | Mouse | Unprocessed form of IL-2 (Gly3Ser)3- extracellular domain of IL-2 Rα + glycine spacer and poly-histidine region | MDSMQLASCVTLTLVLLVNSAPTSSSTSSSTAEAQQQQQQQQQQQQH LEQLLMDLQELLSRMENYRNLKLPRMLTFKFYLPKQATELKDLQCLEDEL GPLRHVLDLTQSKSFQLEDAENFISNIRVTVVKLKGSDNTFECQFDDESA TVVDFLRRWIAFCQSIISTSPQGGGSGGGSGGGSELCLYDPPEVPNATFK ALSYKNGTILNCECKRGFRRLKELVYMRCLGNSWSSNCQCTSNSHDKSR KQVTAQLEHQKEQQTTTDMQKPTQSMHQENLTGHCREPPPWKHEDS KRIYHFVEGQSVHYECIPGYKALQRGPAISICKMKCGKTGWTQPQLTCV DEREHHRFLASEESQGSRNSSPESETSCPITTTDFPQPTETTAMTETFVLT MEYKGGHHHHHH |
| 58 | AA | Human | Unprocessed form IL-2 (Gly3Ser)2- extracellular domain of IL-2 Rα + glycine spacer and poly-histidine region | MDRMQLLSCIALSLALVTNSAPTSSSTKKTQLQLEHLLLDLQMILNGINN YKNPKLTRMLTFKFYMPKKATELKHLQCLEEELKPLEEVLNLAQSKNFHL RPRDLISNINIVIVLELKGSETTFMCEYADETATIVEFLNRWITFCQSIISTLT GGGSGGGSELCDDDPPEIPHATFKAMAYKEGTMLNCECKRGFRRIKSGS LYMLCTGNSSHSSWDNQCQCTSSATRNTTKQVTPQPEEQKERKTTTEM QSPMQPVDQASLPGHCREPPPWENEATERIYHFVVGQMVYYQCVQG YRALHRGPAESVCKMTHGKTRWTQPQLICTGEMETSQFPGEEKPQASP EGRPESETSCLVTTTDFQIQTEMAATMETSIFTTEYQGGHHHHHH |
| 59 | AA | Human | Unprocessed form of IL-2 (Gly3Ser)3- extracellular domain of IL-2 Rα + glycine spacer and poly-histidine region | MDRMQLLSCIALSLALVTNSAPTSSSTKKTQLQLEHLLLDLQMILNGINN YKNPKLTRMLTFKFYMPKKATELKHLQCLEEELKPLEEVLNLAQSKNFHL RPRDLISNINIVIVLELKGSETTFMCEYADETATIVEFLNRWITFCQSIISTLT GGGSGGGSGGGSELCDDDPPEIPHATFKAMAYKEGTMLNCECKRGFRR IKSGSLYMLCTGNSSHSSWDNQCQCTSSATRNTTKQVTPQPEEQKERKT TEMQSPMQPVDQASLPGHCREPPPWENEATERIYHFVVGQMVYYQC VQGYRALHRGPAESVCKMTHGKTRWTQPQLICTGEMETSQFPGEEKP QASPEGRPESETSCLVTTTDFQIQTEMAATMETSIFTTEYQGGHHHHHH |
| 60 | AA | Human | Unprocessed form IL-2 (Gly3Ser)4- extracellular domain of IL-2 Rα + glycine spacer and poly-histidine region | MDRMQLLSCIALSLALVTNSAPTSSSTKKTQLQLEHLLLDLQMILNGINN YKNPKLTRMLTFKFYMPKKATELKHLQCLEEELKPLEEVLNLAQSKNFHL RPRDLISNINIVIVLELKGSETTFMCEYADETATIVEFLNRWITFCQSIISTLT GGGSGGGSGGGSGGGSELCDDDPPEIPHATFKAMAYKEGTMLNCECK RGFRRIKSGSLYMLCTGNSSHSSWDNQCQCTSSATRNTTKQVTPQPEE QKERKTTEMQSPMQPVDQASLPGHCREPPPWENEATERIYHFVVGQ MVYYQCVQGYRALHRGPAESVCKMTHGKTRWTQPQLICTGEMETSQF PGEEKPQASPEGRPESETSCLVTTTDFQIQTEMAATMETSIFTTEYQGGH HHHHH |
| 61 | AA | Human | Unprocessed form IL-2 (Gly4Ser)4- extracellular domain of IL-2 Rα + glycine spacer and | MDRMQLLSCIALSLALVTNSAPTSSSTKKTQLQLEHLLLDLQMILNGINN YKNPKLTRMLTFKFYMPKKATELKHLQCLEEELKPLEEVLNLAQSKNFHL RPRDLISNINIVIVLELKGSETTFMCEYADETATIVEFLNRWITFCQSIISTLT GGGGSGGGGSGGGGSGGGGSELCDDDPPEIPHATFKAMAYKEGTML NCECKRGFRRIKSGSLYMLCTGNSSHSSWDNQCQCTSSATRNTTKQVT PQPEEQKERKTTEMQSPMQPVDQASLPGHCREPPPWENEATERIYHFV VGQMVYYQCVQGYRALHRGPAESVCKMTHGKTRWTQPQLICTGEME |

TABLE 1-continued

Summary of Sequences

| SEQ ID NO | AA/NT | Source | Description | |
|---|---|---|---|---|
| | | | poly-histidine region | TSQFPGEEKPQASPEGRPESETSCLVTTTDFQ1QTEMAATMETSIFTTEY QGGHHHHHH |
| 62 | AA | Human | Mature form IL-2 (Gly3Ser)3-extracellular domain of mutIL-2 Rα | APTSSSTKKTQLQLEHLLLDLQMILNGINNYKNPKLTRMLTFKFYMPKKA TELKHLQCLEEELKPLEEVLNLAQSKNFHLRPRDLISNINVIVLELKGSETTF MCEYADETATIVEFLNRWITFCQSIISTLTGGGSGGGSGGGSELCDDDPP EIPHATFKAMAYKEGTMLNCECKRGFTSIKSGSLYMLCTGNSSHSSWDN QCQCTSSATRNTTKQVTPQPEEQKERKTTEMQSPMQPVDQASLPGHC RaREPPPWENEATERIYHFVVGQMVYYQCVQGYRALHRGPAESVCKMTH GKTRWTQPQLICTGEMETSQFPGEEKPQASPEGRPESETSCLVTTTDFQI QTEMAATMETSIFTTEYQ |
| 63 | NT | Human | Unprocessed form IL-2 (Gly3Ser)3-extracellular domain of mutIL-2 Rα Mut | ATGGACAGGATGCAACTCCTGTCTTGCATTGCACTAAGTCTTGCACTT GTCACAAACAGTGCACCTACTTCAAGTTCTACAAAGAAAACACAGCT ACAACTGGAGCATTTACTGCTGGATTTACAGATGATTTTGAATGGAAT TAATAATTACAAGAATCCCAAACTCACCAGGATGCTCACATTTAAGTT TTACATGCCCAAGAAGGCCACAGAACTGAAACATCTTCAGTGTCTAG RaAAGAAGAACTCAAACCTCTGGAGGAAGTGCTAAATTTAGCTCAAAGC AAAAACTTTCACTTAAGACCCAGGGACTTAATCAGCAATATCAACGTA ATAGTTCTGGAACTAAAGGGATCTGAAACAACATTCATGTGTGAATA TGCTGATGAGACAGCAACCATTGTAGAATTTCTGAACAGATGGATTA CCTTTTGTCAAAGCATCATCTCAACACTGACTggtggaggttctggtggaggt tcaggtggaggttcgGAGCTCTGTGACGATGACCCGCCAGAGATCCCACA CGCCACATTCAAAGCCATGGCCTACAAGGAAGGAACCATGTTGAACT GTGAATGCAAGAGAGGTTTCACCTCAATAAAAAGCGGGTCACTCTAT ATGCTCTGTACAGGAAACTCTAGCCACTCGTCCTGGGACAACCAATG TCAATGCACAAGCTCTGCCACTCGGAACACAACGAAACAAGTGACAC CTCAACCTGAAGAACAGAAAGAAAGGAAAACCACAGAAATGCAAAG TCCAATGCAGCCAGTGGACCAAGCGAGCCTTCCAGGTCACTGCAGGG AACCTCCACCATGGGAAAATGAAGCCACAGAGAGAATTTATCATTTC GTGGTGGGGCAGATGGTTTATTATCAGTGCGTCCAGGGATACAGGG CTCTACACAGAGGTCCTGCTGAGAGCGTCTGCAAAATGACCCACGGG AAGACAAGGTGGACCCAGCCCCAGCTCATATGCACAGGTGAAATGG AGACCAGTCAGTTTCCAGGTGAAGAAGCCTCAGGCAAGCCCCGA AGGCCGTCCTGAGAGTGAGACTTCCTGCCTCGTCACAACAACAGATT TTCAAATACAGACAGAAATGGCTGCAACCATGGAGACGTCCATATTT ACAACAGAGTACCAGGGTGGACATCACCATCACCATCACTAATAA |
| 64 | AA | Human | Mature form IL-2 (Gly4Ser)4-extracellular domain of mutIL-2 Rα | APTSSSTKKTQLQLEHLLLDLQMILNGINNYKNPKLTRMLTFKFYMPKKA TELKHLQCLEEELKPLEEVLNLAQSKNFHLRPRDLISNINVIVLELKGSETTF MCEYADETATIVEFLNRWITFCQSIISTLTGGGSGGGSGGGSGGGS SELCDDDPPEIPHATFKAMAYKEGTMLNCECKRGFTSIKSGSLYMLCTG NSSHSSWDNQCQCTSSATRNTTKQVTPQPEEQKERKTTEMQSPMQPV DQASLPGHCREPPPWENEATERIYHFVVGQMVYYQCVQGYRALHRGP AESVCKMTHGKTRWTQPQLICTGEMETSQFPGEEKPQASPEGRPESET SCLVTTTDFQIQTEMAATMETSIFTTEYQ |
| 65 | NT | Human | Unprocessed form IL-2 (Gly4Ser)4-extracellular domain of mutIL-2 Rα | ATGGACAGGATGCAACTCCTGTCTTGCATTGCACTAAGTCTTGCACTT GTCACAAACAGTGCACCTACTTCAAGTTCTACAAAGAAAACACAGCT ACAACTGGAGCATTTACTGCTGGATTTACAGATGATTTTGAATGGAAT TAATAATTACAAGAATCCCAAACTCACCAGGATGCTCACATTTAAGTT TTACATGCCCAAGAAGGCCACAGAACTGAAACATCTTCAGTGTCTAG AAGAAGAACTCAAACCTCTGGAGGAAGTGCTAAATTTAGCTCAAAGC AAAAACTTTCACTTAAGACCCAGGGACTTAATCAGCAATATCAACGTA ATAGTTCTGGAACTAAAGGGATCTGAAACAACATTCATGTGTGAATA TGCTGATGAGACAGCAACCATTGTAGAATTTCTGAACAGATGGATTA CCTTTTGTCAAAGCATCATCTCAACACTGACTggtggaggtggatctggtgga ggtggatcaggtggaggtggatccggtggaggtggatct GAGCTCTGTGACGATGACCCGCCAGAGATCCCACACGCCACATTCAA AGCCATGGCCTACAAGGAAGGAACCATGTTGAACTGTGAATGCAAG AGAGGTTTCACCTCAATAAAAAGCGGGTCACTCTATATGCTCTGTACA GGAAACTCTAGCCACTCGTCCTGGGACAACCAATGTCAATGCACAAG CTCTGCCACTCGGAACACAACGAAACAAGTGACACCTCAACCTGAAG AACAGAAAGAAAGGAAAACCACAGAAATGCAAAGTCCAATGCAGCC AGTGGACCAAGCGAGCCTTCCAGGTCACTGCAGGGAACCTCCACCAT GGGAAAATGAAGCCACAGAGAGAATTTATCATTTCGTGGTGGGGCA GATGGTTTATTATCAGTGCGTCCAGGGATACAGGGCTCTACACAGAG GTCCTGCTGAGAGCGTCTGCAAAATGACCCACGGGAAGACAAGGTG |

TABLE 1-continued

Summary of Sequences

| SEQ ID NO | AA/ NT | Source | Description |
|---|---|---|---|
| | | | GACCCAGCCCCAGCTCATATGCACAGGTGAAATGGAGACCAGTCAGT TTCCAGGTGAAGAGAAGCCTCAGGCAAGCCCCGAAGGCCGTCCTGA GAGTGAGACTTCCTGCCTCGTCACAACAACAGATTTTCAAATACAGAC AGAAATGGCTGCAACCATGGAGACGTCCATATTTACAACAGAGTACC AGGGTGGACATCACCATCACCATCACTAATAA |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A fusion protein comprising:
   (a) a first polypeptide comprising an Interleukin-2 (IL-2); and
   (b) a second polypeptide, fused in frame to the first polypeptide by a linker, wherein the linker consists of the amino acid sequence set forth as SEQ ID NO: 13, and wherein the second polypeptide comprises the extracellular domain of Interleukin-2 Receptor alpha (IL-2Rα), which has the IL-2Rα extracellular domain activity, wherein the fusion protein increases T regulatory cell activity.

2. The fusion protein of claim 1, wherein the fusion protein has an increased IL-2 potency when compared to a polypeptide consisting of the IL-2.

3. The fusion protein of claim 1, wherein the fusion protein has an increased persistent IL-2 stimulation of IL-2R bearing lymphocytes in vivo when compared to a polypeptide consisting of the IL-2.

4. The fusion protein of claim 1, wherein the fusion protein further comprises a leader peptide.

5. The fusion protein of claim 1, wherein the first polypeptide comprising IL-2 comprises an amino acid sequence that has at least 95% sequence identity to the amino acid sequence set forth as SEQ ID NO: 2.

6. The fusion protein of claim 5, wherein the first polypeptide comprising IL-2 comprises the amino acid sequence set forth as SEQ ID NO: 2.

7. The fusion protein of claim 5, wherein the second polypeptide comprising the extracellular domain of IL-2Rα comprises the amino acid sequence set forth as SEQ ID NO: 7.

8. A pharmaceutical composition comprising the fusion protein of claim 5 and a pharmaceutically acceptable carrier.

9. The fusion protein of claim 1, wherein the first polypeptide comprises an amino acid sequence having 1-5 amino acid deletions or truncations relative to the amino acid sequence set forth as SEQ ID NO: 2.

10. The fusion protein of claim 1, wherein the fusion protein comprises an amino acid sequence having at least 95% sequence identity to the amino acid sequence set forth as SEQ ID NO: 62.

11. The fusion protein of claim 1, wherein the fusion protein comprises the amino acid sequence set forth as SEQ ID NO: 62.

12. The fusion protein of claim 1, wherein the fusion protein comprises the amino acid sequence set forth as any one of SEQ ID NO: 26, 27, 36, 37, 57 or 59.

13. A pharmaceutical composition comprising the fusion protein of claim 12 and a pharmaceutically acceptable carrier.

14. The fusion protein of claim 1, wherein the fusion protein comprises the amino acid sequence set forth as SEQ ID NO: 26.

15. A pharmaceutical composition comprising the fusion protein of claim 1 and a pharmaceutically acceptable carrier.

* * * * *

SEQUENCE LISTING

<160> NUMBER OF SEQ ID NOS: 65

<210> SEQ ID NO 1
<211> LENGTH: 153
<212> TYPE: PRT
<213> ORGANISM: Homo sapeins

<400> SEQUENCE: 1

```
Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

<210> SEQ ID NO 2
<211> LENGTH: 133
<212> TYPE: PRT
<213> ORGANISM: Homo sapiens

<400> SEQUENCE: 2

```
Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

```
<210> SEQ ID NO 3
<211> LENGTH: 169
<212> TYPE: PRT
<213> ORGANISM: Mus musculus

<400> SEQUENCE: 3

Met Tyr Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
                20                  25                  30

Glu Ala Gln Gln Gln Gln Gln Gln Gln Gln Gln Gln Gln His Leu
            35                  40                  45

Glu Gln Leu Leu Met Asp Leu Gln Glu Leu Leu Ser Arg Met Glu Asn
        50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
        115                 120                 125

Val Lys Leu Lys Gly Ser Asp Asn Thr Phe Glu Cys Gln Phe Asp Asp
    130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln
                165
```

```
<210> SEQ ID NO 4
<211> LENGTH: 149
<212> TYPE: PRT
<213> ORGANISM: Mus musculus

<400> SEQUENCE: 4

Ala Pro Thr Ser Ser Ser Thr Ser Ser Thr Ala Glu Ala Gln Gln
1               5                   10                  15
```

```
Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
            35                  40                  45

Lys Leu Pro Arg Met Leu Thr Phe Lys Phe Tyr Leu Pro Lys Gln Ala
 50                  55                  60

Thr Glu Leu Lys Asp Leu Gln Cys Leu Glu Asp Glu Leu Gly Pro Leu
 65                  70                  75                  80

Arg His Val Leu Asp Leu Thr Gln Ser Lys Ser Phe Gln Leu Glu Asp
                 85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Glu Ser Ala Thr
            115                 120                 125

Val Val Asp Phe Leu Arg Arg Trp Ile Ala Phe Cys Gln Ser Ile Ile
            130                 135                 140

Ser Thr Ser Pro Gln
145

<210> SEQ ID NO 5
<211> LENGTH: 272
<212> TYPE: PRT
<213> ORGANISM: Homo sapiens

<400> SEQUENCE: 5

Met Asp Ser Tyr Leu Leu Met Trp Gly Leu Leu Thr Phe Ile Met Val
 1               5                  10                  15

Pro Gly Cys Gln Ala Glu Leu Cys Asp Asp Asp Pro Pro Glu Ile Pro
            20                  25                  30

His Ala Thr Phe Lys Ala Met Ala Tyr Lys Glu Gly Thr Met Leu Asn
            35                  40                  45

Cys Glu Cys Lys Arg Gly Phe Arg Arg Ile Lys Ser Gly Ser Leu Tyr
 50                  55                  60

Met Leu Cys Thr Gly Asn Ser Ser His Ser Ser Trp Asp Asn Gln Cys
 65                  70                  75                  80

Gln Cys Thr Ser Ser Ala Thr Arg Asn Thr Thr Lys Gln Val Thr Pro
                 85                  90                  95

Gln Pro Glu Glu Gln Lys Glu Arg Lys Thr Thr Glu Met Gln Ser Pro
            100                 105                 110

Met Gln Pro Val Asp Gln Ala Ser Leu Pro Gly His Cys Arg Glu Pro
            115                 120                 125

Pro Pro Trp Glu Asn Glu Ala Thr Glu Arg Ile Tyr His Phe Val Val
            130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
            180                 185                 190

Phe Pro Gly Glu Glu Lys Pro Gln Ala Ser Pro Glu Gly Arg Pro Glu
            195                 200                 205

Ser Glu Thr Ser Cys Leu Val Thr Thr Thr Asp Phe Gln Ile Gln Thr
            210                 215                 220

Glu Met Ala Ala Thr Met Glu Thr Ser Ile Phe Thr Thr Glu Tyr Gln
```

Val Ala Val Ala Gly Cys Val Phe Leu Leu Ile Ser Val Leu Leu Leu
225                 230                 235                 240
                        245                 250                 255

Ser Gly Leu Thr Trp Gln Arg Arg Gln Arg Lys Ser Arg Arg Thr Ile
                        260                 265                 270

<210> SEQ ID NO 6
<211> LENGTH: 251
<212> TYPE: PRT
<213> ORGANISM: Homo sapiens

<400> SEQUENCE: 6

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
                20                  25                  30

Gly Phe Arg Arg Ile Lys Ser Gly Ser Leu Tyr Met Leu Cys Thr Gly
            35                  40                  45

Asn Ser Ser His Ser Ser Trp Asp Asn Gln Cys Gln Cys Thr Ser Ser
50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Trp Glu Asn
                100                 105                 110

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
            180                 185                 190

Leu Val Thr Thr Thr Asp Phe Gln Ile Gln Thr Glu Met Ala Ala Thr
                195                 200                 205

Met Glu Thr Ser Ile Phe Thr Thr Glu Tyr Gln Val Ala Val Ala Gly
210                 215                 220

Cys Val Phe Leu Leu Ile Ser Val Leu Leu Leu Ser Gly Leu Thr Trp
225                 230                 235                 240

Gln Arg Arg Gln Arg Lys Ser Arg Arg Thr Ile
                245                 250

<210> SEQ ID NO 7
<211> LENGTH: 219
<212> TYPE: PRT
<213> ORGANISM: Homo sapiens

<400> SEQUENCE: 7

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
                20                  25                  30

Gly Phe Arg Arg Ile Lys Ser Gly Ser Leu Tyr Met Leu Cys Thr Gly

```
            35                  40                  45
Asn Ser Ser His Ser Ser Trp Asp Asn Gln Cys Gln Cys Thr Ser Ser
 50                  55                  60

Ala Thr Arg Asn Thr Thr Lys Gln Val Thr Pro Gln Pro Glu Glu Gln
 65                  70                  75                  80

Lys Glu Arg Lys Thr Thr Glu Met Gln Ser Pro Met Gln Pro Val Asp
                 85                  90                  95

Gln Ala Ser Leu Pro Gly His Cys Arg Glu Pro Pro Pro Trp Glu Asn
             100                 105                 110

Glu Ala Thr Glu Arg Ile Tyr His Phe Val Val Gly Gln Met Val Tyr
         115                 120                 125

Tyr Gln Cys Val Gln Gly Tyr Arg Ala Leu His Arg Gly Pro Ala Glu
     130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
            180                 185                 190

Leu Val Thr Thr Thr Asp Phe Gln Ile Gln Thr Glu Met Ala Ala Thr
        195                 200                 205

Met Glu Thr Ser Ile Phe Thr Thr Glu Tyr Gln
    210                 215

<210> SEQ ID NO 8
<211> LENGTH: 268
<212> TYPE: PRT
<213> ORGANISM: Mus musculus

<400> SEQUENCE: 8

Met Glu Pro Arg Leu Leu Met Leu Gly Phe Leu Ser Leu Thr Ile Val
  1               5                  10                  15

Pro Ser Cys Arg Ala Glu Leu Cys Leu Tyr Asp Pro Pro Glu Val Pro
                 20                  25                  30

Asn Ala Thr Phe Lys Ala Leu Ser Tyr Lys Asn Gly Thr Ile Leu Asn
             35                  40                  45

Cys Glu Cys Lys Arg Gly Phe Arg Arg Leu Lys Glu Leu Val Tyr Met
 50                  55                  60

Arg Cys Leu Gly Asn Ser Trp Ser Ser Asn Cys Gln Cys Thr Ser Asn
 65                  70                  75                  80

Ser His Asp Lys Ser Arg Lys Gln Val Thr Ala Gln Leu Glu His Gln
                 85                  90                  95

Lys Glu Gln Gln Thr Thr Thr Asp Met Gln Lys Pro Thr Gln Ser Met
            100                 105                 110

His Gln Glu Asn Leu Thr Gly His Cys Arg Glu Pro Pro Pro Trp Lys
        115                 120                 125

His Glu Asp Ser Lys Arg Ile Tyr His Phe Val Glu Gly Gln Ser Val
    130                 135                 140

His Tyr Glu Cys Ile Pro Gly Tyr Lys Ala Leu Gln Arg Gly Pro Ala
145                 150                 155                 160

Ile Ser Ile Cys Lys Met Lys Cys Gly Lys Thr Gly Trp Thr Gln Pro
                165                 170                 175

Gln Leu Thr Cys Val Asp Glu Arg Glu His His Arg Phe Leu Ala Ser
            180                 185                 190
```

```
Glu Glu Ser Gln Gly Ser Arg Asn Ser Ser Pro Glu Ser Glu Thr Ser
            195                 200                 205

Cys Pro Ile Thr Thr Thr Asp Phe Pro Gln Pro Thr Glu Thr Thr Ala
210                 215                 220

Met Thr Glu Thr Phe Val Leu Thr Met Glu Tyr Lys Val Ala Val Ala
225                 230                 235                 240

Ser Cys Leu Phe Leu Leu Ile Ser Ile Leu Leu Ser Gly Leu Thr
                245                 250                 255

Trp Gln His Arg Trp Arg Lys Ser Arg Arg Thr Ile
            260                 265

<210> SEQ ID NO 9
<211> LENGTH: 247
<212> TYPE: PRT
<213> ORGANISM: Mus musculus

<400> SEQUENCE: 9

Glu Leu Cys Leu Tyr Asp Pro Glu Val Pro Asn Ala Thr Phe Lys
1               5                   10                  15

Ala Leu Ser Tyr Lys Asn Gly Thr Ile Leu Asn Cys Glu Cys Lys Arg
            20                  25                  30

Gly Phe Arg Arg Leu Lys Glu Leu Val Tyr Met Arg Cys Leu Gly Asn
            35                  40                  45

Ser Trp Ser Ser Asn Cys Gln Cys Thr Ser Asn Ser His Asp Lys Ser
50                  55                  60

Arg Lys Gln Val Thr Ala Gln Leu Glu His Gln Lys Glu Gln Gln Thr
65                  70                  75                  80

Thr Thr Asp Met Gln Lys Pro Thr Gln Ser Met His Gln Glu Asn Leu
                85                  90                  95

Thr Gly His Cys Arg Glu Pro Pro Trp Lys His Glu Asp Ser Lys
            100                 105                 110

Arg Ile Tyr His Phe Val Glu Gly Gln Ser Val His Tyr Glu Cys Ile
            115                 120                 125

Pro Gly Tyr Lys Ala Leu Gln Arg Gly Pro Ala Ile Ser Ile Cys Lys
130                 135                 140

Met Lys Cys Gly Lys Thr Gly Trp Thr Gln Pro Gln Leu Thr Cys Val
145                 150                 155                 160

Asp Glu Arg Glu His His Arg Phe Leu Ala Ser Glu Glu Ser Gln Gly
            165                 170                 175

Ser Arg Asn Ser Ser Pro Glu Ser Glu Thr Ser Cys Pro Ile Thr Thr
            180                 185                 190

Thr Asp Phe Pro Gln Pro Thr Glu Thr Thr Ala Met Thr Glu Thr Phe
            195                 200                 205

Val Leu Thr Met Glu Tyr Lys Val Ala Val Ala Ser Cys Leu Phe Leu
            210                 215                 220

Leu Ile Ser Ile Leu Leu Leu Ser Gly Leu Thr Trp Gln His Arg Trp
225                 230                 235                 240

Arg Lys Ser Arg Arg Thr Ile
                245

<210> SEQ ID NO 10
<211> LENGTH: 215
<212> TYPE: PRT
<213> ORGANISM: Mus musculus

<400> SEQUENCE: 10
```

```
Glu Leu Cys Leu Tyr Asp Pro Pro Glu Val Pro Asn Ala Thr Phe Lys
1               5                   10                  15

Ala Leu Ser Tyr Lys Asn Gly Thr Ile Leu Asn Cys Glu Cys Lys Arg
            20                  25                  30

Gly Phe Arg Arg Leu Lys Glu Leu Val Tyr Met Arg Cys Leu Gly Asn
        35                  40                  45

Ser Trp Ser Ser Asn Cys Gln Cys Thr Ser Asn Ser His Asp Lys Ser
50                  55                  60

Arg Lys Gln Val Thr Ala Gln Leu Glu His Gln Lys Glu Gln Gln Thr
65                  70                  75                  80

Thr Thr Asp Met Gln Lys Pro Thr Gln Ser Met His Gln Glu Asn Leu
                85                  90                  95

Thr Gly His Cys Arg Glu Pro Pro Trp Lys His Glu Asp Ser Lys
                100                 105                 110

Arg Ile Tyr His Phe Val Glu Gly Gln Ser Val His Tyr Glu Cys Ile
            115                 120                 125

Pro Gly Tyr Lys Ala Leu Gln Arg Gly Pro Ala Ile Ser Ile Cys Lys
        130                 135                 140

Met Lys Cys Gly Lys Thr Gly Trp Thr Gln Pro Gln Leu Thr Cys Val
145                 150                 155                 160

Asp Glu Arg Glu His His Arg Phe Leu Ala Ser Glu Glu Ser Gln Gly
                165                 170                 175

Ser Arg Asn Ser Ser Pro Glu Ser Glu Thr Ser Cys Pro Ile Thr Thr
            180                 185                 190

Thr Asp Phe Pro Gln Pro Thr Glu Thr Thr Ala Met Thr Glu Thr Phe
        195                 200                 205

Val Leu Thr Met Glu Tyr Lys
    210                 215

<210> SEQ ID NO 11
<211> LENGTH: 16
<212> TYPE: PRT
<213> ORGANISM: Artificial Sequence
<220> FEATURE:
<223> OTHER INFORMATION: (Gly3Ser)4 linker

<400> SEQUENCE: 11

Gly Gly Gly Ser Gly Gly Gly Ser Gly Gly Gly Ser Gly Gly Gly Ser
1               5                   10                  15

<210> SEQ ID NO 12
<211> LENGTH: 8
<212> TYPE: PRT
<213> ORGANISM: Artificial Sequence
<220> FEATURE:
<223> OTHER INFORMATION: (Gly3Ser)2 linker

<400> SEQUENCE: 12

Gly Gly Gly Ser Gly Gly Gly Ser
1               5

<210> SEQ ID NO 13
<211> LENGTH: 12
<212> TYPE: PRT
<213> ORGANISM: Artificial Sequence
<220> FEATURE:
<223> OTHER INFORMATION: (Gly3Ser)3 linker

<400> SEQUENCE: 13

Gly Gly Gly Ser Gly Gly Gly Ser Gly Gly Gly Ser
```

<210> SEQ ID NO 14
<211> LENGTH: 20
<212> TYPE: PRT
<213> ORGANISM: Artificial Sequence
<220> FEATURE:
<223> OTHER INFORMATION: (Gly3Ser)5 linker

<400> SEQUENCE: 14

Gly Gly Gly Ser Gly Gly Gly Ser Gly Gly Gly Ser Gly Gly Gly Ser
1               5                   10                  15
Gly Gly Gly Ser
            20

<210> SEQ ID NO 15
<211> LENGTH: 3
<212> TYPE: PRT
<213> ORGANISM: Artificial Sequence
<220> FEATURE:
<223> OTHER INFORMATION: Gly3 linker

<400> SEQUENCE: 15

Gly Gly Gly
1

<210> SEQ ID NO 16
<211> LENGTH: 384
<212> TYPE: PRT
<213> ORGANISM: Artificial Sequence
<220> FEATURE:
<223> OTHER INFORMATION: Synthesized Mature form of IL-2
      (Gly4Ser)4-extracellular domain of IL-2 R

<400> SEQUENCE: 16

Ala Pro Thr Ser Ser Ser Thr Ser Ser Ser Thr Ala Glu Ala Gln Gln
1               5                   10                  15

Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
        35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Glu Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
        115                 120                 125

Val Val Asp Phe Leu Arg Arg Trp Ile Ala Phe Cys Gln Ser Ile Ile
    130                 135                 140

Ser Thr Ser Pro Gln Gly Gly Gly Gly Ser Gly Gly Gly Gly Ser Gly
145                 150                 155                 160

Gly Gly Ser Gly Gly Gly Ser Glu Leu Cys Leu Tyr Asp Pro
                165                 170                 175

Pro Glu Val Pro Asn Ala Thr Phe Lys Ala Leu Ser Tyr Lys Asn Gly
            180                 185                 190

Thr Ile Leu Asn Cys Glu Cys Lys Arg Gly Phe Arg Arg Leu Lys Glu

-continued

```
                195                 200                 205
Leu Val Tyr Met Arg Cys Leu Gly Asn Ser Trp Ser Ser Asn Cys Gln
            210                 215                 220
Cys Thr Ser Asn Ser His Asp Lys Ser Arg Lys Gln Val Thr Ala Gln
225                 230                 235                 240
Leu Glu His Gln Lys Glu Gln Gln Thr Thr Thr Asp Met Gln Lys Pro
                245                 250                 255
Thr Gln Ser Met His Gln Glu Asn Leu Thr Gly His Cys Arg Glu Pro
            260                 265                 270
Pro Pro Trp Lys His Glu Asp Ser Lys Arg Ile Tyr His Phe Val Glu
            275                 280                 285
Gly Gln Ser Val His Tyr Glu Cys Ile Pro Gly Tyr Lys Ala Leu Gln
            290                 295                 300
Arg Gly Pro Ala Ile Ser Ile Cys Lys Met Lys Cys Gly Lys Thr Gly
305                 310                 315                 320
Trp Thr Gln Pro Gln Leu Thr Cys Val Asp Glu Arg Glu His His Arg
                325                 330                 335
Phe Leu Ala Ser Glu Glu Ser Gln Gly Ser Arg Asn Ser Ser Pro Glu
            340                 345                 350
Ser Glu Thr Ser Cys Pro Ile Thr Thr Thr Asp Phe Pro Gln Pro Thr
                355                 360                 365
Glu Thr Thr Ala Met Thr Glu Thr Phe Val Leu Thr Met Glu Tyr Lys
            370                 375                 380

<210> SEQ ID NO 17
<211> LENGTH: 404
<212> TYPE: PRT
<213> ORGANISM: Artificial Sequence
<220> FEATURE:
<223> OTHER INFORMATION: Synthesized unprocessed form of IL-2
      (Gly4Ser)4-extracellular domain of IL-2 R

<400> SEQUENCE: 17

Met Asp Ser Met Gln Leu Ala Ser Cys Val Thr Leu Thr Leu Val Leu
1               5                   10                  15
Leu Val Asn Ser Ala Pro Thr Ser Ser Thr Ser Ser Ser Thr Ala
                20                  25                  30
Glu Ala Gln Gln Gln Gln Gln Gln Gln Gln Gln Gln Gln His Leu
            35                  40                  45
Glu Gln Leu Leu Met Asp Leu Gln Glu Leu Leu Ser Arg Met Glu Asn
        50                  55                  60
Tyr Arg Asn Leu Lys Leu Pro Arg Met Leu Thr Phe Lys Phe Tyr Leu
65                  70                  75                  80
Pro Lys Gln Ala Thr Glu Leu Lys Asp Leu Gln Cys Leu Glu Asp Glu
                85                  90                  95
Leu Gly Pro Leu Arg His Val Leu Asp Leu Thr Gln Ser Lys Ser Phe
            100                 105                 110
Gln Leu Glu Asp Ala Glu Asn Phe Ile Ser Asn Ile Arg Val Thr Val
        115                 120                 125
Val Lys Leu Lys Gly Ser Asp Asn Thr Phe Glu Cys Gln Phe Asp Asp
130                 135                 140
Glu Ser Ala Thr Val Val Asp Phe Leu Arg Arg Trp Ile Ala Phe Cys
145                 150                 155                 160
Gln Ser Ile Ile Ser Thr Ser Pro Gln Gly Gly Gly Ser Gly Gly
                165                 170                 175
```

```
Gly Gly Ser Gly Gly Gly Ser Gly Gly Gly Ser Glu Leu Cys
            180             185             190

Leu Tyr Asp Pro Pro Glu Val Pro Asn Ala Thr Phe Lys Ala Leu Ser
        195                 200                 205

Tyr Lys Asn Gly Thr Ile Leu Asn Cys Glu Cys Lys Arg Gly Phe Arg
        210                 215                 220

Arg Leu Lys Glu Leu Val Tyr Met Arg Cys Leu Gly Asn Ser Trp Ser
225                 230                 235                 240

Ser Asn Cys Gln Cys Thr Ser Asn Ser His Asp Lys Ser Arg Lys Gln
                245                 250                 255

Val Thr Ala Gln Leu Glu His Gln Lys Glu Gln Gln Thr Thr Thr Asp
        260                 265                 270

Met Gln Lys Pro Thr Gln Ser Met His Gln Glu Asn Leu Thr Gly His
        275                 280                 285

Cys Arg Glu Pro Pro Trp Lys His Glu Asp Ser Lys Arg Ile Tyr
        290                 295                 300

His Phe Val Glu Gly Gln Ser Val His Tyr Glu Cys Ile Pro Gly Tyr
305                 310                 315                 320

Lys Ala Leu Gln Arg Gly Pro Ala Ile Ser Ile Cys Lys Met Lys Cys
                325                 330                 335

Gly Lys Thr Gly Trp Thr Gln Pro Gln Leu Thr Cys Val Asp Glu Arg
                340                 345                 350

Glu His His Arg Phe Leu Ala Ser Glu Glu Ser Gln Gly Ser Arg Asn
            355                 360                 365

Ser Ser Pro Glu Ser Glu Thr Ser Cys Pro Ile Thr Thr Thr Asp Phe
        370                 375                 380

Pro Gln Pro Thr Glu Thr Thr Ala Met Thr Glu Thr Phe Val Leu Thr
385                 390                 395                 400

Met Glu Tyr Lys

<210> SEQ ID NO 18
<211> LENGTH: 389
<212> TYPE: PRT
<213> ORGANISM: Artificial Sequence
<220> FEATURE:
<223> OTHER INFORMATION: Synthesized mature form of IL-2
      (Gly4Ser)5- extracellular domain of IL-2 R

<400> SEQUENCE: 18

Ala Pro Thr Ser Ser Thr Ser Ser Ser Thr Ala Glu Ala Gln Gln
1               5                   10                  15

Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
        35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Glu Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
        115                 120                 125
```

```
Val Val Asp Phe Leu Arg Arg Trp Ile Ala Phe Cys Gln Ser Ile Ile
    130                 135                 140

Ser Thr Ser Pro Gln Gly Gly Gly Ser Gly Gly Gly Gly Ser Gly
145                 150                 155                 160

Gly Gly Gly Ser Gly Gly Gly Gly Ser Gly Gly Gly Gly Ser Glu Leu
                165                 170                 175

Cys Leu Tyr Asp Pro Pro Glu Val Pro Asn Ala Thr Phe Lys Ala Leu
            180                 185                 190

Ser Tyr Lys Asn Gly Thr Ile Leu Asn Cys Glu Cys Lys Arg Gly Phe
        195                 200                 205

Arg Arg Leu Lys Glu Leu Val Tyr Met Arg Cys Leu Gly Asn Ser Trp
    210                 215                 220

Ser Ser Asn Cys Gln Cys Thr Ser Asn Ser His Asp Lys Ser Arg Lys
225                 230                 235                 240

Gln Val Thr Ala Gln Leu Glu His Gln Lys Glu Gln Gln Thr Thr Thr
                245                 250                 255

Asp Met Gln Lys Pro Thr Gln Ser Met His Gln Glu Asn Leu Thr Gly
            260                 265                 270

His Cys Arg Glu Pro Pro Pro Trp Lys His Glu Asp Ser Lys Arg Ile
        275                 280                 285

Tyr His Phe Val Glu Gly Gln Ser Val His Tyr Glu Cys Ile Pro Gly
    290                 295                 300

Tyr Lys Ala Leu Gln Arg Gly Pro Ala Ile Ser Ile Cys Lys Met Lys
305                 310                 315                 320

Cys Gly Lys Thr Gly Trp Thr Gln Pro Gln Leu Thr Cys Val Asp Glu
                325                 330                 335

Arg Glu His His Arg Phe Leu Ala Ser Glu Glu Ser Gln Gly Ser Arg
            340                 345                 350

Asn Ser Ser Pro Glu Ser Glu Thr Ser Cys Pro Ile Thr Thr Thr Asp
        355                 360                 365

Phe Pro Gln Pro Thr Glu Thr Thr Ala Met Thr Glu Thr Phe Val Leu
    370                 375                 380

Thr Met Glu Tyr Lys
385

<210> SEQ ID NO 19
<211> LENGTH: 409
<212> TYPE: PRT
<213> ORGANISM: Artificial Sequence
<220> FEATURE:
<223> OTHER INFORMATION: Synthesized unprocessed form of IL-2
      (Gly4Ser)5- extracellular domain of IL-2 R

<400> SEQUENCE: 19

Met Asp Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
                20                  25                  30

Glu Ala Gln Gln Gln Gln Gln Gln Gln Gln Gln Gln Gln His Leu
            35                  40                  45

Glu Gln Leu Leu Met Asp Leu Gln Glu Leu Leu Ser Arg Met Glu Asn
50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95
```

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
            115                 120                 125

Val Lys Leu Lys Gly Ser Asp Asn Thr Phe Glu Cys Gln Phe Asp Asp
130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln Gly Gly Gly Ser Gly Gly Gly
            165                 170                 175

Gly Gly Ser Gly Gly Gly Gly Ser Gly Gly Gly Gly Ser Gly Gly Gly
            180                 185                 190

Gly Ser Glu Leu Cys Leu Tyr Asp Pro Pro Glu Val Pro Asn Ala Thr
            195                 200                 205

Phe Lys Ala Leu Ser Tyr Lys Asn Gly Thr Ile Leu Asn Cys Glu Cys
            210                 215                 220

Lys Arg Gly Phe Arg Arg Leu Lys Glu Leu Val Tyr Met Arg Cys Leu
225                 230                 235                 240

Gly Asn Ser Trp Ser Ser Asn Cys Gln Cys Thr Ser Asn Ser His Asp
            245                 250                 255

Lys Ser Arg Lys Gln Val Thr Ala Gln Leu Glu His Gln Lys Glu Gln
            260                 265                 270

Gln Thr Thr Thr Asp Met Gln Lys Pro Thr Gln Ser Met His Gln Glu
            275                 280                 285

Asn Leu Thr Gly His Cys Arg Glu Pro Pro Trp Lys His Glu Asp
            290                 295                 300

Ser Lys Arg Ile Tyr His Phe Val Glu Gly Gln Ser Val His Tyr Glu
305                 310                 315                 320

Cys Ile Pro Gly Tyr Lys Ala Leu Gln Arg Gly Pro Ala Ile Ser Ile
            325                 330                 335

Cys Lys Met Lys Cys Gly Lys Thr Gly Trp Thr Gln Pro Gln Leu Thr
            340                 345                 350

Cys Val Asp Glu Arg Glu His His Arg Phe Leu Ala Ser Glu Glu Ser
            355                 360                 365

Gln Gly Ser Arg Asn Ser Ser Pro Glu Ser Glu Thr Ser Cys Pro Ile
            370                 375                 380

Thr Thr Thr Asp Phe Pro Gln Pro Thr Glu Thr Thr Ala Met Thr Glu
385                 390                 395                 400

Thr Phe Val Leu Thr Met Glu Tyr Lys
            405

<210> SEQ ID NO 20
<211> LENGTH: 380
<212> TYPE: PRT
<213> ORGANISM: Artificial Sequence
<220> FEATURE:
<223> OTHER INFORMATION: Synthesized mature form of IL-2
      (Gly3Ser)4- extracellular domain of IL-2 R

<400> SEQUENCE: 20

Ala Pro Thr Ser Ser Ser Thr Ser Ser Ser Thr Ala Glu Ala Gln Gln
1               5                   10                  15

Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu

```
            35                  40                  45
Lys Leu Pro Arg Met Leu Thr Phe Lys Phe Tyr Leu Pro Lys Gln Ala
 50                  55                  60

Thr Glu Leu Lys Asp Leu Gln Cys Leu Glu Asp Glu Leu Gly Pro Leu
 65                  70                  75                  80

Arg His Val Leu Asp Leu Thr Gln Ser Lys Ser Phe Gln Leu Glu Asp
                 85                  90                  95

Ala Glu Asn Phe Ile Ser Asn Ile Arg Val Thr Val Val Lys Leu Lys
                100                 105                 110

Gly Ser Asp Asn Thr Phe Glu Cys Gln Phe Asp Asp Glu Ser Ala Thr
                115                 120                 125

Val Val Asp Phe Leu Arg Arg Trp Ile Ala Phe Cys Gln Ser Ile Ile
                130                 135                 140

Ser Thr Ser Pro Gln Gly Gly Ser Gly Gly Ser Gly Gly Gly
145                 150                 155                 160

Ser Gly Gly Gly Ser Glu Leu Cys Leu Tyr Asp Pro Pro Glu Val Pro
                165                 170                 175

Asn Ala Thr Phe Lys Ala Leu Ser Tyr Lys Asn Gly Thr Ile Leu Asn
                180                 185                 190

Cys Glu Cys Lys Arg Gly Phe Arg Arg Leu Lys Glu Leu Val Tyr Met
                195                 200                 205

Arg Cys Leu Gly Asn Ser Trp Ser Ser Asn Cys Gln Cys Thr Ser Asn
210                 215                 220

Ser His Asp Lys Ser Arg Lys Gln Val Thr Ala Gln Leu Glu His Gln
225                 230                 235                 240

Lys Glu Gln Gln Thr Thr Thr Asp Met Gln Lys Pro Thr Gln Ser Met
                245                 250                 255

His Gln Glu Asn Leu Thr Gly His Cys Arg Glu Pro Pro Trp Lys
                260                 265                 270

His Glu Asp Ser Lys Arg Ile Tyr His Phe Val Glu Gly Gln Ser Val
                275                 280                 285

His Tyr Glu Cys Ile Pro Gly Tyr Lys Ala Leu Gln Arg Gly Pro Ala
                290                 295                 300

Ile Ser Ile Cys Lys Met Lys Cys Gly Lys Thr Gly Trp Thr Gln Pro
305                 310                 315                 320

Gln Leu Thr Cys Val Asp Glu Arg Glu His His Arg Phe Leu Ala Ser
                325                 330                 335

Glu Glu Ser Gln Gly Ser Arg Asn Ser Ser Pro Glu Ser Glu Thr Ser
                340                 345                 350

Cys Pro Ile Thr Thr Thr Asp Phe Pro Gln Pro Thr Glu Thr Thr Ala
                355                 360                 365

Met Thr Glu Thr Phe Val Leu Thr Met Glu Tyr Lys
                370                 375                 380

<210> SEQ ID NO 21
<211> LENGTH: 400
<212> TYPE: PRT
<213> ORGANISM: Artificial Sequence
<220> FEATURE:
<223> OTHER INFORMATION: Synthesized unprocessed form of IL-2
      (Gly3Ser)4- extracellular domain of IL-2 R

<400> SEQUENCE: 21

Met Asp Ser Met Gln Leu Ala Ser Cys Val Thr Leu Thr Leu Val Leu
 1               5                  10                  15
```

Leu Val Asn Ser Ala Pro Thr Ser Ser Ser Thr Ser Ser Thr Ala
            20                  25                  30

Glu Ala Gln Gln Gln Gln Gln Gln Gln Gln Gln Gln Gln His Leu
        35                  40                  45

Glu Gln Leu Leu Met Asp Leu Gln Glu Leu Leu Ser Arg Met Glu Asn
50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
        115                 120                 125

Val Lys Leu Lys Gly Ser Asp Asn Thr Phe Glu Cys Gln Phe Asp Asp
    130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln Gly Gly Gly Ser Gly Gly Gly
                165                 170                 175

Ser Gly Gly Gly Ser Gly Gly Ser Glu Leu Cys Leu Tyr Asp Pro
            180                 185                 190

Pro Glu Val Pro Asn Ala Thr Phe Lys Ala Leu Ser Tyr Lys Asn Gly
        195                 200                 205

Thr Ile Leu Asn Cys Glu Cys Lys Arg Gly Phe Arg Arg Leu Lys Glu
210                 215                 220

Leu Val Tyr Met Arg Cys Leu Gly Asn Ser Trp Ser Ser Asn Cys Gln
225                 230                 235                 240

Cys Thr Ser Asn Ser His Asp Lys Ser Arg Lys Gln Val Thr Ala Gln
                245                 250                 255

Leu Glu His Gln Lys Glu Gln Gln Thr Thr Thr Asp Met Gln Lys Pro
        260                 265                 270

Thr Gln Ser Met His Gln Glu Asn Leu Thr Gly His Cys Arg Glu Pro
    275                 280                 285

Pro Pro Trp Lys His Glu Asp Ser Lys Arg Ile Tyr His Phe Val Glu
290                 295                 300

Gly Gln Ser Val His Tyr Glu Cys Ile Pro Gly Tyr Lys Ala Leu Gln
305                 310                 315                 320

Arg Gly Pro Ala Ile Ser Ile Cys Lys Met Lys Cys Gly Lys Thr Gly
                325                 330                 335

Trp Thr Gln Pro Gln Leu Thr Cys Val Asp Glu Arg Glu His His Arg
        340                 345                 350

Phe Leu Ala Ser Glu Glu Ser Gln Gly Ser Arg Asn Ser Ser Pro Glu
    355                 360                 365

Ser Glu Thr Ser Cys Pro Ile Thr Thr Thr Asp Phe Pro Gln Pro Thr
370                 375                 380

Glu Thr Thr Ala Met Thr Glu Thr Phe Val Leu Thr Met Glu Tyr Lys
385                 390                 395                 400

<210> SEQ ID NO 22
<211> LENGTH: 372
<212> TYPE: PRT
<213> ORGANISM: Artificial Sequence
<220> FEATURE:
<223> OTHER INFORMATION: Synthesized mature form IL-2

(Gly4Ser)4- extracellular domain of IL-2 R

<400> SEQUENCE: 22

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr Gly Gly Gly Gly Ser Gly Gly Gly Ser Gly
130                 135                 140

Gly Gly Ser Gly Gly Gly Gly Ser Glu Leu Cys Asp Asp Asp Pro
145                 150                 155                 160

Pro Glu Ile Pro His Ala Thr Phe Lys Ala Met Ala Tyr Lys Glu Gly
                165                 170                 175

Thr Met Leu Asn Cys Glu Cys Lys Arg Gly Phe Arg Arg Ile Lys Ser
            180                 185                 190

Gly Ser Leu Tyr Met Leu Cys Thr Gly Asn Ser Ser His Ser Ser Trp
            195                 200                 205

Asp Asn Gln Cys Gln Cys Thr Ser Ser Ala Thr Arg Asn Thr Thr Lys
210                 215                 220

Gln Val Thr Pro Gln Pro Glu Glu Gln Lys Glu Arg Lys Thr Thr Glu
225                 230                 235                 240

Met Gln Ser Pro Met Gln Pro Val Asp Gln Ala Ser Leu Pro Gly His
                245                 250                 255

Cys Arg Glu Pro Pro Pro Trp Glu Asn Glu Ala Thr Glu Arg Ile Tyr
            260                 265                 270

His Phe Val Val Gly Gln Met Val Tyr Tyr Gln Cys Val Gln Gly Tyr
            275                 280                 285

Arg Ala Leu His Arg Gly Pro Ala Glu Ser Val Cys Lys Met Thr His
290                 295                 300

Gly Lys Thr Arg Trp Thr Gln Pro Gln Leu Ile Cys Thr Gly Glu Met
305                 310                 315                 320

Glu Thr Ser Gln Phe Pro Gly Glu Glu Lys Pro Gln Ala Ser Pro Glu
                325                 330                 335

Gly Arg Pro Glu Ser Glu Thr Ser Cys Leu Val Thr Thr Thr Asp Phe
            340                 345                 350

Gln Ile Gln Thr Glu Met Ala Ala Thr Met Glu Thr Ser Ile Phe Thr
            355                 360                 365

Thr Glu Tyr Gln
370

<210> SEQ ID NO 23
<211> LENGTH: 392

<212> TYPE: PRT
<213> ORGANISM: Artificial Sequence
<220> FEATURE:
<223> OTHER INFORMATION: Synthesized unprocessed form IL-2
    (Gly4Ser)4- extracellular domain of IL-2 R

<400> SEQUENCE: 23

```
Met Asp Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr Gly Gly Gly Gly Ser Gly Gly
145                 150                 155                 160

Gly Gly Ser Gly Gly Gly Gly Ser Gly Gly Gly Gly Ser Glu Leu Cys
                165                 170                 175

Asp Asp Asp Pro Pro Glu Ile Pro His Ala Thr Phe Lys Ala Met Ala
            180                 185                 190

Tyr Lys Glu Gly Thr Met Leu Asn Cys Glu Cys Lys Arg Gly Phe Arg
        195                 200                 205

Arg Ile Lys Ser Gly Ser Leu Tyr Met Leu Cys Thr Gly Asn Ser Ser
210                 215                 220

His Ser Ser Trp Asp Asn Gln Cys Gln Cys Thr Ser Ser Ala Thr Arg
225                 230                 235                 240

Asn Thr Thr Lys Gln Val Thr Pro Gln Pro Glu Glu Gln Lys Glu Arg
                245                 250                 255

Lys Thr Thr Glu Met Gln Ser Pro Met Gln Pro Val Asp Gln Ala Ser
            260                 265                 270

Leu Pro Gly His Cys Arg Glu Pro Pro Pro Trp Glu Asn Glu Ala Thr
        275                 280                 285

Glu Arg Ile Tyr His Phe Val Val Gly Gln Met Val Tyr Tyr Gln Cys
290                 295                 300

Val Gln Gly Tyr Arg Ala Leu His Arg Gly Pro Ala Glu Ser Val Cys
305                 310                 315                 320

Lys Met Thr His Gly Lys Thr Arg Trp Thr Gln Pro Gln Leu Ile Cys
                325                 330                 335

Thr Gly Glu Met Glu Thr Ser Gln Phe Pro Gly Glu Glu Lys Pro Gln
            340                 345                 350

Ala Ser Pro Glu Gly Arg Pro Glu Ser Glu Thr Ser Cys Leu Val Thr
        355                 360                 365

Thr Thr Asp Phe Gln Ile Gln Thr Glu Met Ala Ala Thr Met Glu Thr
370                 375                 380
```

Ser Ile Phe Thr Thr Glu Tyr Gln
385                 390

<210> SEQ ID NO 24
<211> LENGTH: 368
<212> TYPE: PRT
<213> ORGANISM: Artificial Sequence
<220> FEATURE:
<223> OTHER INFORMATION: Synthesized mature form IL-2
      (Gly3Ser)4- extracellular domain of IL-2 R

<400> SEQUENCE: 24

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
                115                 120                 125

Ile Ser Thr Leu Thr Gly Gly Gly Ser Gly Gly Gly Ser Gly Gly Gly
130                 135                 140

Ser Gly Gly Gly Ser Glu Leu Cys Asp Asp Asp Pro Pro Glu Ile Pro
145                 150                 155                 160

His Ala Thr Phe Lys Ala Met Ala Tyr Lys Glu Gly Thr Met Leu Asn
                165                 170                 175

Cys Glu Cys Lys Arg Gly Phe Arg Arg Ile Lys Ser Gly Ser Leu Tyr
                180                 185                 190

Met Leu Cys Thr Gly Asn Ser Ser His Ser Ser Trp Asp Asn Gln Cys
                195                 200                 205

Gln Cys Thr Ser Ser Ala Thr Arg Asn Thr Thr Lys Gln Val Thr Pro
                210                 215                 220

Gln Pro Glu Glu Gln Lys Glu Arg Lys Thr Thr Glu Met Gln Ser Pro
225                 230                 235                 240

Met Gln Pro Val Asp Gln Ala Ser Leu Pro Gly His Cys Arg Glu Pro
                245                 250                 255

Pro Pro Trp Glu Asn Glu Ala Thr Glu Arg Ile Tyr His Phe Val Val
                260                 265                 270

Gly Gln Met Val Tyr Tyr Gln Cys Val Gln Gly Tyr Arg Ala Leu His
                275                 280                 285

Arg Gly Pro Ala Glu Ser Val Cys Lys Met Thr His Gly Lys Thr Arg
                290                 295                 300

Trp Thr Gln Pro Gln Leu Ile Cys Thr Gly Glu Met Glu Thr Ser Gln
305                 310                 315                 320

Phe Pro Gly Glu Glu Lys Pro Gln Ala Ser Pro Glu Gly Arg Pro Glu
                325                 330                 335

Ser Glu Thr Ser Cys Leu Val Thr Thr Thr Asp Phe Gln Ile Gln Thr

```
                 340              345              350
Glu Met Ala Ala Thr Met Glu Thr Ser Ile Phe Thr Thr Glu Tyr Gln
            355              360              365

<210> SEQ ID NO 25
<211> LENGTH: 388
<212> TYPE: PRT
<213> ORGANISM: Artificial Sequence
<220> FEATURE:
<223> OTHER INFORMATION: Synthesized unprocessed form IL-2
      (Gly3Ser)4- extracellular domain of IL-2 R

<400> SEQUENCE: 25

Met Asp Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr Gly Gly Gly Ser Gly Gly Gly
145                 150                 155                 160

Ser Gly Gly Gly Ser Gly Gly Gly Ser Glu Leu Cys Asp Asp Asp Pro
                165                 170                 175

Pro Glu Ile Pro His Ala Thr Phe Lys Ala Met Ala Tyr Lys Glu Gly
            180                 185                 190

Thr Met Leu Asn Cys Glu Cys Lys Arg Gly Phe Arg Arg Ile Lys Ser
        195                 200                 205

Gly Ser Leu Tyr Met Leu Cys Thr Gly Asn Ser Ser His Ser Ser Trp
210                 215                 220

Asp Asn Gln Cys Gln Cys Thr Ser Ser Ala Thr Arg Asn Thr Thr Lys
225                 230                 235                 240

Gln Val Thr Pro Gln Pro Glu Glu Gln Lys Glu Arg Lys Thr Thr Glu
                245                 250                 255

Met Gln Ser Pro Met Gln Pro Val Asp Gln Ala Ser Leu Pro Gly His
            260                 265                 270

Cys Arg Glu Pro Pro Pro Trp Glu Asn Glu Ala Thr Glu Arg Ile Tyr
        275                 280                 285

His Phe Val Val Gly Gln Met Val Tyr Tyr Gln Cys Val Gln Gly Tyr
290                 295                 300

Arg Ala Leu His Arg Gly Pro Ala Glu Ser Val Cys Lys Met Thr His
305                 310                 315                 320

Gly Lys Thr Arg Trp Thr Gln Pro Gln Leu Ile Cys Thr Gly Glu Met
                325                 330                 335
```

```
Glu Thr Ser Gln Phe Pro Gly Glu Glu Lys Pro Gln Ala Ser Pro Glu
                340                 345                 350

Gly Arg Pro Glu Ser Glu Thr Ser Cys Leu Val Thr Thr Thr Asp Phe
            355                 360                 365

Gln Ile Gln Thr Glu Met Ala Ala Thr Met Glu Thr Ser Ile Phe Thr
        370                 375                 380

Thr Glu Tyr Gln
385

<210> SEQ ID NO 26
<211> LENGTH: 364
<212> TYPE: PRT
<213> ORGANISM: Artificial Sequence
<220> FEATURE:
<223> OTHER INFORMATION: Synthesized mature form IL-2
      (Gly3Ser)3- extracellular domain of IL-2 R

<400> SEQUENCE: 26

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Ser Gly Gly Gly Ser Gly Gly Gly
130                 135                 140

Ser Glu Leu Cys Asp Asp Asp Pro Pro Glu Ile Pro His Ala Thr Phe
145                 150                 155                 160

Lys Ala Met Ala Tyr Lys Glu Gly Thr Met Leu Asn Cys Glu Cys Lys
                165                 170                 175

Arg Gly Phe Arg Arg Ile Lys Ser Gly Ser Leu Tyr Met Leu Cys Thr
            180                 185                 190

Gly Asn Ser Ser His Ser Ser Trp Asp Asn Gln Cys Gln Cys Thr Ser
        195                 200                 205

Ser Ala Thr Arg Asn Thr Thr Lys Gln Val Thr Pro Gln Pro Glu Glu
    210                 215                 220

Gln Lys Glu Arg Lys Thr Thr Glu Met Gln Ser Pro Met Gln Pro Val
225                 230                 235                 240

Asp Gln Ala Ser Leu Pro Gly His Cys Arg Glu Pro Pro Pro Trp Glu
                245                 250                 255

Asn Glu Ala Thr Glu Arg Ile Tyr His Phe Val Val Gly Gln Met Val
            260                 265                 270

Tyr Tyr Gln Cys Val Gln Gly Tyr Arg Ala Leu His Arg Gly Pro Ala
        275                 280                 285

Glu Ser Val Cys Lys Met Thr His Gly Lys Thr Arg Trp Thr Gln Pro
    290                 295                 300
```

```
Gln Leu Ile Cys Thr Gly Glu Met Glu Thr Ser Gln Phe Pro Gly Glu
305                 310                 315                 320

Glu Lys Pro Gln Ala Ser Pro Glu Gly Arg Pro Glu Ser Glu Thr Ser
                325                 330                 335

Cys Leu Val Thr Thr Asp Phe Gln Ile Gln Thr Glu Met Ala Ala
            340                 345                 350

Thr Met Glu Thr Ser Ile Phe Thr Thr Glu Tyr Gln
        355                 360

<210> SEQ ID NO 27
<211> LENGTH: 384
<212> TYPE: PRT
<213> ORGANISM: Artificial Sequence
<220> FEATURE:
<223> OTHER INFORMATION: Synthesized unprocessed form of IL-2
      (Gly3Ser)3- extracellular domain of IL-2 R

<400> SEQUENCE: 27

Met Asp Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr Gly Gly Gly Ser Gly Gly Gly
145                 150                 155                 160

Ser Gly Gly Gly Ser Glu Leu Cys Asp Asp Asp Pro Pro Glu Ile Pro
                165                 170                 175

His Ala Thr Phe Lys Ala Met Ala Tyr Lys Glu Gly Thr Met Leu Asn
            180                 185                 190

Cys Glu Cys Lys Arg Gly Phe Arg Arg Ile Lys Ser Gly Ser Leu Tyr
        195                 200                 205

Met Leu Cys Thr Gly Asn Ser Ser His Ser Ser Trp Asp Asn Gln Cys
210                 215                 220

Gln Cys Thr Ser Ser Ala Thr Arg Asn Thr Thr Lys Gln Val Thr Pro
225                 230                 235                 240

Gln Pro Glu Glu Gln Lys Glu Arg Lys Thr Thr Glu Met Gln Ser Pro
                245                 250                 255

Met Gln Pro Val Asp Gln Ala Ser Leu Pro Gly His Cys Arg Glu Pro
            260                 265                 270

Pro Pro Trp Glu Asn Glu Ala Thr Glu Arg Ile Tyr His Phe Val Val
        275                 280                 285

Gly Gln Met Val Tyr Tyr Gln Cys Val Gln Gly Tyr Arg Ala Leu His
```

```
                290                 295                 300
Arg Gly Pro Ala Glu Ser Val Cys Lys Met Thr His Gly Lys Thr Arg
305                 310                 315                 320

Trp Thr Gln Pro Gln Leu Ile Cys Thr Gly Glu Met Glu Thr Ser Gln
                325                 330                 335

Phe Pro Gly Glu Glu Lys Pro Gln Ala Ser Pro Glu Gly Arg Pro Glu
                340                 345                 350

Ser Glu Thr Ser Cys Leu Val Thr Thr Thr Asp Phe Gln Ile Gln Thr
                355                 360                 365

Glu Met Ala Ala Thr Met Glu Thr Ser Ile Phe Thr Thr Glu Tyr Gln
                370                 375                 380

<210> SEQ ID NO 28
<211> LENGTH: 66
<212> TYPE: DNA
<213> ORGANISM: Artificial Sequence
<220> FEATURE:
<223> OTHER INFORMATION: IL-2 leader optimized Kozak sequence

<400> SEQUENCE: 28
gccaccatgg acaggatgca actcctgtct tgcattgcac taagtcttgc acttgtcaca      60
aacagt                                                                66

<210> SEQ ID NO 29
<211> LENGTH: 1239
<212> TYPE: DNA
<213> ORGANISM: Artificial Sequence
<220> FEATURE:
<223> OTHER INFORMATION: Synthesized unprocessed form of IL-2
      (Gly4Ser)4-extracellular domain of IL-2 R

<400> SEQUENCE: 29
atggacagca tgcagctcgc atcctgtgtc acattgacac ttgtgctcct tgtcaacagc      60
gcacccactt caagctctac ttcaagctct acagcggaag cacagcagca gcagcagcag     120
cagcagcagc agcagcacct ggagcagctg ttgatggacc tacaggagct cctgagcagg     180
atggagaatt acaggaacct gaaactcccc aggatgctca ccttcaaatt ttacttgccc     240
aagcaggcca cagaattgaa agatcttcag tgcctagaag atgaacttgg acctctgcgg     300
catgttctgg atttgactca aagcaaaagc tttcaattgg aagatgctga aatttcatc      360 agcaatatca gagtaactgt tgtaaaacta aagggctctg acaacacatt tgagtgccaa     420
ttcgatgatg agtcagcaac tgtggtggac tttctgagga tggatagc cttctgtcaa       480 agcatcatct caacaagccc tcaaggtgga ggtggatctg gtggaggtgg atcaggtgga     540
ggtggatccg gtggaggtgg atctgaactg tgtctgtatg acccaccgga ggtccccaat     600
gccacattca aagccctctc ctacaagaac ggcaccatcc taaactgtga atgcaagaga     660
ggtttccgaa gactaaagga attggtctat atgcgttgct taggaaactc ctggagcagc     720
aactgccagt gcaccagcaa ctcccatgac aaatcgagaa agcaagttac agctcaactt     780
gaacaccaga aagagcaaca accacaacaa gacatgcaga agccaacaca gtctatgcac     840
caagagaacc ttacaggtca ctgcagggag ccacctcctt ggaaacatga agattccaag     900
agaatctatc atttcgtgga aggacagagt gttcactacg agtgtattcc gggatacaag     960
gctctacaga gaggtcctgc tattagcatc tgcaagatga gtgtgggaa aacggggtgg    1020 actcagcccc agctcacatg tgtagatgaa agaacacc accgatttct ggctagtgag    1080
gaatctcaag gaagcagaaa ttcttctccc gagagtgaga cttcctgccc cataaccacc    1140
```

```
acagacttcc cacaacccac agaaacaact gcaatgacgg agacatttgt gctcacaatg    1200
gagtataagg gtggacatca ccatcaccat cactaataa                           1239
```

<210> SEQ ID NO 30
<211> LENGTH: 1227
<212> TYPE: DNA
<213> ORGANISM: Artificial Sequence
<220> FEATURE:
<223> OTHER INFORMATION: Synthesized unprocessed form of IL-2
      (Gly3Ser)4- extracellular domain of IL-2 R

<400> SEQUENCE: 30

```
atggacagca tgcagctcgc atcctgtgtc acattgacac ttgtgctcct tgtcaacagc     60
gcacccactt caagctctac ttcaagctct acagcggaag cacagcagca gcagcagcag    120
cagcagcagc agcagcacct ggagcagctg ttgatggacc tacaggagct cctgagcagg    180
atggagaatt acaggaacct gaaactcccc aggatgctca ccttcaaatt ttacttgccc    240
aagcaggcca cagaattgaa agatcttcag tgcctagaag atgaacttgg acctctgcgg    300
catgttctgg atttgactca aagcaaaagc tttcaattgg aagatgctga gaatttcatc    360
agcaatatca gagtaactgt tgtaaaacta aagggctctg acaacacatt tgagtgccaa    420
ttcgatgatg agtcagcaac tgtggtggac tttctgagga gatggatagc cttctgtcaa    480
agcatcatct caacaagccc tcaaggtgga ggttctggtg gaggttcagg tggaggttcg    540
ggtggaggtt ctgaactgtg tctgtatgac ccacccgagg tccccaatgc acattcaaa    600 gccctctcct acaagaacgg caccatccta actgtgaat gcaagagagg tttccgaaga    660
ctaaaggaat tggtctatat gcgttgctta ggaaactcct ggagcagcaa ctgccagtgc    720
accagcaact cccatgacaa atcgagaaag caagttacag ctcaacttga acaccagaaa    780
gagcaacaaa ccacaacaga catgcagaag ccaacacagt ctatgcacca agagaacctt    840
acaggtcact gcagggagcc acctccttgg aaacatgaag attccaagag aatctatcat    900
ttcgtggaag acagagtgt tcactacgag tgtattccgg atacaaggc tctacagaga    960 ggtcctgcta ttagcatctg caagatgaag tgtgggaaaa cggggtggac tcagcccag   1020 ctcacatgtg tagatgaaag agaacaccac cgatttctgg ctagtgagga atctcaagga   1080
agcagaaatt cttctcccga gagtgagact tcctgcccca taaccaccac agacttccca   1140
caacccacag aaacaactgc aatgacggag acatttgtgc tcacaatgga gtataagggt   1200
ggacatcacc atcaccatca ctaataa                                       1227
```

<210> SEQ ID NO 31
<211> LENGTH: 1254
<212> TYPE: DNA
<213> ORGANISM: Artificial Sequence
<220> FEATURE:
<223> OTHER INFORMATION: Synthesized unprocessed form of IL-2
      (Gly4Ser)5- extracellular domain of IL-2 R

<400> SEQUENCE: 31

```
atggacagca tgcagctcgc atcctgtgtc acattgacac ttgtgctcct tgtcaacagc     60
gcacccactt caagctctac ttcaagctct acagcggaag cacagcagca gcagcagcag    120
cagcagcagc agcagcacct ggagcagctg ttgatggacc tacaggagct cctgagcagg    180
atggagaatt acaggaacct gaaactcccc aggatgctca ccttcaaatt ttacttgccc    240
aagcaggcca cagaattgaa agatcttcag tgcctagaag atgaacttgg acctctgcgg    300
```

```
catgttctgg atttgactca aagcaaaagc tttcaattgg aagatgctga gaatttcatc    360
agcaatatca gagtaactgt tgtaaaacta aagggctctg acaacacatt tgagtgccaa    420
ttcgatgatg agtcagcaac tgtggtggac tttctgagga gatggatagc cttctgtcaa    480
agcatcatct caacaagccc tcaaggtgga ggtggatcag gtggaggtgg atctggtgga    540
ggtggatcag gtggaggtgg atccggtgga ggtggatctg aactgtgtct gtatgaccca    600
cccgaggtcc ccaatgccac attcaaagcc ctctcctaca gaacggcac catcctaaac     660 tgtgaatgca agagaggttt ccgaagacta aaggaattgg tctatatgcg ttgcttagga    720
aactcctgga gcagcaactg ccagtgcacc agcaactccc atgacaaatc gagaaagcaa    780
gttacagctc aacttgaaca ccagaaagag caacaaacca acagacat gcagaagcca      840 acacagtcta tgcaccaaga gaaccttaca ggtcactgca gggagccacc tccttggaaa    900
catgaagatt ccaagagaat ctatcatttc gtggaaggac agagtgttca ctacgagtgt    960
attccgggat acaaggctct acagagaggt cctgctatta gcatctgcaa gatgaagtgt    1020
gggaaaacgg ggtggactca gccccagctc acatgtgtag atgaaagaga acaccaccga   1080
tttctggcta gtgaggaatc tcaaggaagc agaaattctt ctcccgagag tgagacttcc    1140
tgccccataa ccaccacaga cttcccacaa cccacagaaa caactgcaat gacggagaca    1200
tttgtgctca aatggagta aagggtgga catcaccatc accatcacta ataa            1254
```

<210> SEQ ID NO 32
<211> LENGTH: 1206
<212> TYPE: DNA
<213> ORGANISM: Artificial Sequence
<220> FEATURE:
<223> OTHER INFORMATION: Synthesized unprocessed form IL-2 (Gly4Ser)4- extracellular domain of IL-2 R

<400> SEQUENCE: 32

```
atggacagga tgcaactcct gtcttgcatt gcactaagtc ttgcacttgt cacaaacagt     60
gcacctactt caagttctac aaagaaaaca cagctacaac tggagcattt actgctggat    120
ttacagatga ttttgaatgg aattaataat tacaagaatc ccaaactcac caggatgctc    180
acatttaagt tttacatgcc caagaaggcc acagaactga acatcttca gtgtctagaa     240 gaagaactca aacctctgga ggaagtgcta aatttagctc aaagcaaaaa ctttcactta    300 agacccagg acttaatcag caatatcaac gtaatagttc tggaactaaa gggatctgaa     360
acaacattca tgtgtgaata tgctgatgag acagcaacca ttgtagaatt tctgaacaga    420
tggattacct tttgtcaaag catcatctca cactgactg tggaggtgg atctggtgga      480 ggtggatcag gtggaggtgg atccggtgga ggtggatctg agctctgtga cgatgacccg    540
ccagagatcc cacacgccac attcaaagcc atggcctaca ggaaggaac catgttgaac     600 tgtgaatgca agagaggttt ccgcagaata aaaagcgggt cactctatat gctctgtaca    660
ggaaactcta gccactcgtc ctgggacaac caatgtcaat gcacaagctc tgccactcgg    720
aacacaacga acaagtgac acctcaacct gaagaacaga agaaaggaa accacagaa       780 atgcaaagtc caatgcagcc agtggaccaa gcgagccttc caggtcactg cagggaacct    840
ccaccatggg aaaatgaagc cacagagaga atttatcatt tcgtggtggg gcagatggtt    900
tattatcagt gcgtccaggg atacagggct ctacacagag gtcctgctga gagcgtctgc    960
aaaatgaccc acgggaagac aaggtggacc cagcccagc tcatatgcac aggtgaaatg     1020
gagaccagtc agtttccagg tgaagagaag cctcaggca gccccgaagg ccgtcctgag    1080
```

-continued

| agtgagactt cctgcctcgt cacaacaaca gattttcaaa tacagacaga aatggctgca | 1140 |
| accatggaga cgtccatatt tacaacagag taccagggtg acatcacca tcaccatcac | 1200 |
| taataa | 1206 |

<210> SEQ ID NO 33
<211> LENGTH: 1194
<212> TYPE: DNA
<213> ORGANISM: Artificial Sequence
<220> FEATURE:
<223> OTHER INFORMATION: Synthesized unprocessed form IL-2
      (Gly3Ser)4- extracellular domain of IL-2 R

<400> SEQUENCE: 33

| atggacagga tgcaactcct gtcttgcatt gcactaagtc ttgcacttgt cacaaacagt | 60 |
| gcacctactt caagttctac aaagaaaaca cagctacaac tggagcattt actgctggat | 120 |
| ttacagatga ttttgaatgg aattaataat acaagaatc ccaaactcac caggatgctc | 180 |
| acatttaagt tttacatgcc caagaaggcc acagaactga acatcttca gtgtctagaa | 240 |
| gaagaactca aacctctgga ggaagtgcta aatttagctc aaagcaaaaa ctttcactta | 300 |
| agacccaggg acttaatcag caatatcaac gtaatagttc tggaactaaa gggatctgaa | 360 |
| acaacattca tgtgtgaata tgctgatgag acagcaacca ttgtagaatt tctgaacaga | 420 |
| tggattacct tttgtcaaag catcatctca cactgactg gtgaggttc tggtggaggt | 480 |
| tcaggtggag gttcgggtgg aggttctgag ctctgtgacg atgacccgcc agagatccca | 540 |
| cacgccacat tcaaagccat ggcctacaag gaaggaacca tgttgaactg tgaatgcaag | 600 |
| agaggtttcc gcagaataaa aagcgggtca ctctatatgc tctgtacagg aaactctagc | 660 |
| cactcgtcct gggacaacca atgtcaatgc acaagctctg ccactcggaa cacaacgaaa | 720 |
| caagtgacac ctcaacctga gaacagaaaa gaaggaaaa ccacagaaat gcaaagtcca | 780 |
| atgcagccag tggaccaagc gagccttcca ggtcactgca gggaacctcc accatgggaa | 840 |
| aatgaagcca cagagagaat ttatcatttc gtggtggggc agatggttta ttatcagtgc | 900 |
| gtccagggat acagggctct acacagaggt cctgctgaga gcgtctgcaa aatgacccac | 960 |
| gggaagacaa ggtggaccca gccccagctc atatgcacag tgaaatgga ccagtcag | 1020 |
| tttccaggtg aagagaagcc tcaggcaagc cccgaaggcc gtcctgagag tgagacttcc | 1080 |
| tgcctcgtca acaacagat tttcaaata cagacagaaa tggctgcaac catggagacg | 1140 |
| tccatattta acagagta ccagggtgga catcaccatc accatcacta ataa | 1194 |

<210> SEQ ID NO 34
<211> LENGTH: 1182
<212> TYPE: DNA
<213> ORGANISM: Artificial Sequence
<220> FEATURE:
<223> OTHER INFORMATION: Synthesized unprocessed form of IL-2
      (Gly3Ser)3- extracellular domain of IL-2 R

<400> SEQUENCE: 34

| atggacagga tgcaactcct gtcttgcatt gcactaagtc ttgcacttgt cacaaacagt | 60 |
| gcacctactt caagttctac aaagaaaaca cagctacaac tggagcattt actgctggat | 120 |
| ttacagatga ttttgaatgg aattaataat acaagaatc ccaaactcac caggatgctc | 180 |
| acatttaagt tttacatgcc caagaaggcc acagaactga acatcttca gtgtctagaa | 240 |
| gaagaactca aacctctgga ggaagtgcta aatttagctc aaagcaaaaa ctttcactta | 300 |
| agacccaggg acttaatcag caatatcaac gtaatagttc tggaactaaa gggatctgaa | 360 |

```
acaacattca tgtgtgaata tgctgatgag acagcaacca ttgtagaatt tctgaacaga    420
tggattacct tttgtcaaag catcatctca acactgactg gtggaggttc tggtggaggt    480
tcaggtggag gttcggagct ctgtgacgat gacccgccag agatcccaca cgccacattc    540
aaagccatgg cctacaagga aggaaccatg ttgaactgtg aatgcaagag aggtttccgc    600
agaataaaaa gcgggtcact ctatatgctc tgtacaggaa actctagcca ctcgtcctgg    660
gacaaccaat gtcaatgcac aagctctgcc actcggaaca caacgaaaca agtgacacct    720
caacctgaag aacagaaaga aggaaaaacc acagaaatgc aaagtccaat gcagccagtg    780
gaccaagcga gccttccagg tcactgcagg gaacctccac catgggaaaa tgaagccaca    840
gagagaattt atcatttcgt ggtggggcag atggtttatt atcagtgcgt ccagggatac    900
agggctctac acagaggtcc tgctgagagc gtctgcaaaa tgacccacgg aagacaagg     960 tggacccagc cccagctcat atgcacaggt gaaatggaga ccagtcagtt tccaggtgaa    1020
gagaagcctc aggcaagccc cgaaggccgt cctgagagtg agacttcctg cctcgtcaca    1080
acaacagatt ttcaaataca gacagaaatg gctgcaacca tggagacgtc catatttaca    1140
acagagtacc agggtggaca tcaccatcac catcactaat aa                       1182
```

<210> SEQ ID NO 35
<211> LENGTH: 13
<212> TYPE: DNA
<213> ORGANISM: Artificial Sequence
<220> FEATURE:
<223> OTHER INFORMATION: Kozak consensus

<400> SEQUENCE: 35

```
gccgccrcca ugg                                                         13
```

<210> SEQ ID NO 36
<211> LENGTH: 396
<212> TYPE: PRT
<213> ORGANISM: Artificial Sequence
<220> FEATURE:
<223> OTHER INFORMATION: Synthesized unprocessed form of IL-2
      (Gly3Ser)3- extracellular domain of IL-2 R

<400> SEQUENCE: 36

```
Met Tyr Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
            20                  25                  30

Glu Ala Gln Gln Gln Gln Gln Gln Gln Gln Gln Gln Gln His Leu
        35                  40                  45

Glu Gln Leu Leu Met Asp Leu Gln Glu Leu Leu Ser Arg Met Glu Asn
    50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
        115                 120                 125

Val Lys Leu Lys Gly Ser Asp Asn Thr Phe Glu Cys Gln Phe Asp Asp
    130                 135                 140
```

Glu Ser Ala Thr Val Val Asp Phe Leu Arg Arg Trp Ile Ala Phe Cys
145                 150                 155                 160

Gln Ser Ile Ile Ser Thr Ser Pro Gln Gly Gly Ser Gly Gly Gly Gly
                165                 170                 175

Ser Gly Gly Gly Ser Glu Leu Cys Leu Tyr Asp Pro Pro Glu Val Pro
            180                 185                 190

Asn Ala Thr Phe Lys Ala Leu Ser Tyr Lys Asn Gly Thr Ile Leu Asn
        195                 200                 205

Cys Glu Cys Lys Arg Gly Phe Arg Arg Leu Lys Glu Leu Val Tyr Met
    210                 215                 220

Arg Cys Leu Gly Asn Ser Trp Ser Ser Asn Cys Gln Cys Thr Ser Asn
225                 230                 235                 240

Ser His Asp Lys Ser Arg Lys Gln Val Thr Ala Gln Leu Glu His Gln
                245                 250                 255

Lys Glu Gln Gln Thr Thr Thr Asp Met Gln Lys Pro Thr Gln Ser Met
            260                 265                 270

His Gln Glu Asn Leu Thr Gly His Cys Arg Glu Pro Pro Pro Trp Lys
        275                 280                 285

His Glu Asp Ser Lys Arg Ile Tyr His Phe Val Glu Gly Gln Ser Val
    290                 295                 300

His Tyr Glu Cys Ile Pro Gly Tyr Lys Ala Leu Gln Arg Gly Pro Ala
305                 310                 315                 320

Ile Ser Ile Cys Lys Met Lys Cys Gly Lys Thr Gly Trp Thr Gln Pro
                325                 330                 335

Gln Leu Thr Cys Val Asp Glu Arg Glu His His Arg Phe Leu Ala Ser
            340                 345                 350

Glu Glu Ser Gln Gly Ser Arg Asn Ser Ser Pro Glu Ser Glu Thr Ser
        355                 360                 365

Cys Pro Ile Thr Thr Thr Asp Phe Pro Gln Pro Thr Glu Thr Thr Ala
    370                 375                 380

Met Thr Glu Thr Phe Val Leu Thr Met Glu Tyr Lys
385                 390                 395

<210> SEQ ID NO 37
<211> LENGTH: 396
<212> TYPE: PRT
<213> ORGANISM: Artificial Sequence
<220> FEATURE:
<223> OTHER INFORMATION: Synthesized mature form of IL-2
      (Gly3Ser)3- extracellular domain of IL-2 R

<400> SEQUENCE: 37

Met Asp Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
                20                  25                  30

Glu Ala Gln Gln Gln Gln Gln Gln Gln Gln Gln Gln Gln His Leu
            35                  40                  45

Glu Gln Leu Leu Met Asp Leu Gln Glu Leu Leu Ser Arg Met Glu Asn
        50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
        115                 120                 125

Val Lys Leu Lys Gly Ser Asp Asn Thr Phe Glu Cys Gln Phe Asp Asp
130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln Gly Gly Gly Ser Gly Gly Gly
        165                 170                 175

Ser Gly Gly Gly Ser Glu Leu Cys Leu Tyr Asp Pro Pro Glu Val Pro
        180                 185                 190

Asn Ala Thr Phe Lys Ala Leu Ser Tyr Lys Asn Gly Thr Ile Leu Asn
        195                 200                 205

Cys Glu Cys Lys Arg Gly Phe Arg Arg Leu Lys Glu Leu Val Tyr Met
        210                 215                 220

Arg Cys Leu Gly Asn Ser Trp Ser Ser Asn Cys Gln Cys Thr Ser Asn
225                 230                 235                 240

Ser His Asp Lys Ser Arg Lys Gln Val Thr Ala Gln Leu Glu His Gln
        245                 250                 255

Lys Glu Gln Gln Thr Thr Thr Asp Met Gln Lys Pro Thr Gln Ser Met
        260                 265                 270

His Gln Glu Asn Leu Thr Gly His Cys Arg Glu Pro Pro Pro Trp Lys
        275                 280                 285

His Glu Asp Ser Lys Arg Ile Tyr His Phe Val Glu Gly Gln Ser Val
        290                 295                 300

His Tyr Glu Cys Ile Pro Gly Tyr Lys Ala Leu Gln Arg Gly Pro Ala
305                 310                 315                 320

Ile Ser Ile Cys Lys Met Lys Cys Gly Lys Thr Gly Trp Thr Gln Pro
                325                 330                 335

Gln Leu Thr Cys Val Asp Glu Arg Glu His His Arg Phe Leu Ala Ser
        340                 345                 350

Glu Glu Ser Gln Gly Ser Arg Asn Ser Ser Pro Glu Ser Glu Thr Ser
        355                 360                 365

Cys Pro Ile Thr Thr Thr Asp Phe Pro Gln Pro Thr Glu Thr Thr Ala
        370                 375                 380

Met Thr Glu Thr Phe Val Leu Thr Met Glu Tyr Lys
385                 390                 395

<210> SEQ ID NO 38
<211> LENGTH: 397
<212> TYPE: PRT
<213> ORGANISM: Artificial Sequence
<220> FEATURE:
<223> OTHER INFORMATION: Synthesized unprocessed form of IL-2
      (Gly4Ser)5- extracellular domain of IL-2 R

<400> SEQUENCE: 38

Met Asp Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu

```
                65                  70                  75                  80
Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
                100                 105                 110

Val Leu Glu Leu Lys Gly Ser Glu Thr Thr Phe Met Cys Glu Tyr Ala
                115                 120                 125

Asp Glu Thr Ala Thr Ile Val Glu Phe Leu Asn Arg Trp Ile Thr Phe
                130                 135                 140

Cys Gln Ser Ile Ile Ser Thr Leu Thr Gly Gly Gly Ser Gly Gly
145                 150                 155                 160

Gly Gly Ser Gly Gly Gly Ser Gly Gly Gly Ser Gly Gly
                165                 170                 175

Gly Ser Glu Leu Cys Asp Asp Pro Pro Glu Ile Pro His Ala Thr
                180                 185                 190

Phe Lys Ala Met Ala Tyr Lys Glu Gly Thr Met Leu Asn Cys Glu Cys
                195                 200                 205

Lys Arg Gly Phe Arg Arg Ile Lys Ser Gly Ser Leu Tyr Met Leu Cys
210                 215                 220

Thr Gly Asn Ser Ser His Ser Ser Trp Asp Asn Gln Cys Gln Cys Thr
225                 230                 235                 240

Ser Ser Ala Thr Arg Asn Thr Thr Lys Gln Val Thr Pro Gln Pro Glu
                245                 250                 255

Glu Gln Lys Glu Arg Lys Thr Thr Glu Met Gln Ser Pro Met Gln Pro
                260                 265                 270

Val Asp Gln Ala Ser Leu Pro Gly His Cys Arg Glu Pro Pro Pro Trp
                275                 280                 285

Glu Asn Glu Ala Thr Glu Arg Ile Tyr His Phe Val Val Gly Gln Met
                290                 295                 300

Val Tyr Tyr Gln Cys Val Gln Gly Tyr Arg Ala Leu His Arg Gly Pro
305                 310                 315                 320

Ala Glu Ser Val Cys Lys Met Thr His Gly Lys Thr Arg Trp Thr Gln
                325                 330                 335

Pro Gln Leu Ile Cys Thr Gly Glu Met Glu Thr Ser Gln Phe Pro Gly
                340                 345                 350

Glu Glu Lys Pro Gln Ala Ser Pro Glu Gly Arg Pro Glu Ser Glu Thr
                355                 360                 365

Ser Cys Leu Val Thr Thr Thr Asp Phe Gln Ile Gln Thr Glu Met Ala
                370                 375                 380

Ala Thr Met Glu Thr Ser Ile Phe Thr Thr Glu Tyr Gln
385                 390                 395

<210> SEQ ID NO 39
<211> LENGTH: 377
<212> TYPE: PRT
<213> ORGANISM: Artificial Sequence
<220> FEATURE:
<223> OTHER INFORMATION: Synthesized mature form of human IL-2
      (Gly4Ser)5- extracellular domain of IL-2 R

<400> SEQUENCE: 39

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30
```

Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Gly Ser Gly Gly Gly Gly Ser Gly
130                 135                 140

Gly Gly Gly Ser Gly Gly Gly Ser Gly Gly Gly Ser Glu Leu
145                 150                 155                 160

Cys Asp Asp Pro Pro Glu Ile Pro His Ala Thr Phe Lys Ala Met
                165                 170                 175

Ala Tyr Lys Glu Gly Thr Met Leu Asn Cys Glu Cys Lys Arg Gly Phe
            180                 185                 190

Arg Arg Ile Lys Ser Gly Ser Leu Tyr Met Leu Cys Thr Gly Asn Ser
195                 200                 205

Ser His Ser Ser Trp Asp Asn Gln Cys Gln Cys Thr Ser Ser Ala Thr
        210                 215                 220

Arg Asn Thr Thr Lys Gln Val Thr Pro Gln Pro Glu Glu Gln Lys Glu
225                 230                 235                 240

Arg Lys Thr Thr Glu Met Gln Ser Pro Met Gln Pro Val Asp Gln Ala
                245                 250                 255

Ser Leu Pro Gly His Cys Arg Glu Pro Pro Trp Glu Asn Glu Ala
            260                 265                 270

Thr Glu Arg Ile Tyr His Phe Val Val Gly Gln Met Val Tyr Tyr Gln
            275                 280                 285

Cys Val Gln Gly Tyr Arg Ala Leu His Arg Gly Pro Ala Glu Ser Val
290                 295                 300

Cys Lys Met Thr His Gly Lys Thr Arg Trp Thr Gln Pro Gln Leu Ile
305                 310                 315                 320

Cys Thr Gly Glu Met Glu Thr Ser Gln Phe Pro Gly Glu Glu Lys Pro
                325                 330                 335

Gln Ala Ser Pro Glu Gly Arg Pro Glu Ser Glu Thr Ser Cys Leu Val
            340                 345                 350

Thr Thr Thr Asp Phe Gln Ile Gln Thr Glu Met Ala Ala Thr Met Glu
        355                 360                 365

Thr Ser Ile Phe Thr Thr Glu Tyr Gln
        370                 375

<210> SEQ ID NO 40
<211> LENGTH: 20
<212> TYPE: PRT
<213> ORGANISM: Artificial Sequence
<220> FEATURE:
<223> OTHER INFORMATION: Linker sequence (Gly4Ser)4

<400> SEQUENCE: 40

Gly Gly Gly Gly Ser Gly Gly Gly Gly Ser Gly Gly Gly Gly Ser Gly
1               5                   10                  15

-continued

Gly Gly Gly Ser
        20

<210> SEQ ID NO 41
<211> LENGTH: 25
<212> TYPE: PRT
<213> ORGANISM: Artificial Sequence
<220> FEATURE:
<223> OTHER INFORMATION: Linker sequence (Gly4Ser)5

<400> SEQUENCE: 41

Gly Gly Gly Gly Ser Gly Gly Gly Gly Ser Gly Gly Gly Gly Ser Gly
1               5                   10                  15

Gly Gly Gly Ser Gly Gly Gly Gly Ser
        20                  25

<210> SEQ ID NO 42
<211> LENGTH: 1215
<212> TYPE: DNA
<213> ORGANISM: Artificial Sequence
<220> FEATURE:
<223> OTHER INFORMATION: Synthesized unprocessed form IL-2
      (Gly3Ser)3- extracellular domain of IL-2 R

<400> SEQUENCE: 42

```
atggacagca tgcagctcgc atcctgtgtc acattgacac ttgtgctcct tgtcaacagc      60
gcacccactt caagctctac ttcaagctct cagcggaag cacagcagca gcagcagcag     120
cagcagcagc agcagcacct ggagcagctg ttgatggacc tacaggagct cctgagcagg     180
atggagaatt acaggaacct gaaactcccc aggatgctca ccttcaaatt ttacttgccc     240
aagcaggcca cagaattgaa agatcttcag tgcctagaag atgaacttgg acctctgcgg     300
catgttctgg atttgactca aagcaaaagc tttcaattgg aagatgctga gaatttcatc     360
agcaatatca gagtaactgt tgtaaaacta aagggctctg acaacacatt tgagtgccaa     420
ttcgatgatg agtcagcaac tgtggtggac tttctgagga gatggatagc cttctgtcaa     480
agcatcatct caacaagccc tcaaggtgga ggttctggtg aggttcagg tggaggttcg     540 gaactgtgtc tgtatgaccc acccgaggtc cccaatgcca cattcaaagc cctctcctac     600
aagaacggca ccatcctaaa ctgtgaatgc aagagaggtt ccgaagact aaaggaattg     660 gtctatatgc gttgcttagg aaactcctgg agcagcaact gccagtgcac cagcaactcc     720
catgacaaat cgagaaagca agttacagct caacttgaac accagaaaga gcaacaaacc     780
acaacagaca tgcagaagcc aacacagtct atgcaccaag agaaccttac aggtcactgc     840
agggagccac ctccttggaa acatgaagat tccaagagaa tctatcattt cgtggaagga     900
cagagtgttc actacgagtg tattccggga tacaaggctc tacagagagg tcctgctatt     960
agcatctgca agatgaagtg tgggaaaacg gggtggactc agccccagct cacatgtgta    1020
gatgaaagag aacaccaccg atttctggct agtgaggaat ctcaaggaag cagaaattct    1080
tctcccgaga gtgagacttc ctgccccata accaccacag acttcccaca acccacagaa    1140
acaactgcaa tgacggagac atttgtgctc aaatggagt ataagggtgg acatcaccat    1200
caccatcact aataa                                                     1215
```

<210> SEQ ID NO 43
<211> LENGTH: 360
<212> TYPE: PRT
<213> ORGANISM: Artificial Sequence
<220> FEATURE:
<223> OTHER INFORMATION: Synthesized mature form IL-2

(Gly3Ser)2- extracellular domain of IL-2 R

<400> SEQUENCE: 43

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20

<223> OTHER INFORMATION: Synthesized unprocessed form IL-2
      (Gly3Ser)2- extracellular domain of IL-2 R

<400> SEQUENCE: 44

```
Met Asp Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr Gly Gly Gly Ser Gly Gly Gly
145                 150                 155                 160

Ser Glu Leu Cys Asp Asp Asp Pro Pro Glu Ile Pro His Ala Thr Phe
                165                 170                 175

Lys Ala Met Ala Tyr Lys Glu Gly Thr Met Leu Asn Cys Glu Cys Lys
            180                 185                 190

Arg Gly Phe Arg Arg Ile Lys Ser Gly Ser Leu Tyr Met Leu Cys Thr
        195                 200                 205

Gly Asn Ser Ser His Ser Ser Trp Asp Asn Gln Cys Gln Cys Thr Ser
210                 215                 220

Ser Ala Thr Arg Asn Thr Thr Lys Gln Val Thr Pro Gln Pro Glu Glu
225                 230                 235                 240

Gln Lys Glu Arg Lys Thr Thr Glu Met Gln Ser Pro Met Gln Pro Val
                245                 250                 255

Asp Gln Ala Ser Leu Pro Gly His Cys Arg Glu Pro Pro Pro Trp Glu
            260                 265                 270

Asn Glu Ala Thr Glu Arg Ile Tyr His Phe Val Val Gly Gln Met Val
        275                 280                 285

Tyr Tyr Gln Cys Val Gln Gly Tyr Arg Ala Leu His Arg Gly Pro Ala
290                 295                 300

Glu Ser Val Cys Lys Met Thr His Gly Lys Thr Arg Trp Thr Gln Pro
305                 310                 315                 320

Gln Leu Ile Cys Thr Gly Glu Met Glu Thr Ser Gln Phe Pro Gly Glu
                325                 330                 335

Glu Lys Pro Gln Ala Ser Pro Glu Gly Arg Pro Glu Ser Glu Thr Ser
            340                 345                 350

Cys Leu Val Thr Thr Thr Asp Phe Gln Ile Gln Thr Glu Met Ala Ala
        355                 360                 365

Thr Met Glu Thr Ser Ile Phe Thr Thr Glu Tyr Gln
370                 375                 380
```

<210> SEQ ID NO 45

<211> LENGTH: 355
<212> TYPE: PRT
<213> ORGANISM: Artificial Sequence
<220> FEATURE:
<223> OTHER INFORMATION: Synthesized mature form IL-2
      (Gly3)- extracellular domain of IL-2 R

<400> SEQUENCE: 45

```
Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Glu Leu Cys Asp Asp Pro Pro
    130                 135                 140

Glu Ile Pro His Ala Thr Phe Lys Ala Met Ala Tyr Lys Glu Gly Thr
145                 150                 155                 160

Met Leu Asn Cys Glu Cys Lys Arg Gly Phe Arg Arg Ile Lys Ser Gly
                165                 170                 175

Ser Leu Tyr Met Leu Cys Thr Gly Asn Ser Ser His Ser Ser Trp Asp
            180                 185                 190

Asn Gln Cys Gln Cys Thr Ser Ser Ala Thr Arg Asn Thr Thr Lys Gln
        195                 200                 205

Val Thr Pro Gln Pro Glu Glu Gln Lys Glu Arg Lys Thr Thr Glu Met
    210                 215                 220

Gln Ser Pro Met Gln Pro Val Asp Gln Ala Ser Leu Pro Gly His Cys
225                 230                 235                 240

Arg Glu Pro Pro Pro Trp Glu Asn Glu Ala Thr Glu Arg Ile Tyr His
                245                 250                 255

Phe Val Val Gly Gln Met Val Tyr Tyr Gln Cys Val Gln Gly Tyr Arg
            260                 265                 270

Ala Leu His Arg Gly Pro Ala Glu Ser Val Cys Lys Met Thr His Gly
        275                 280                 285

Lys Thr Arg Trp Thr Gln Pro Gln Leu Ile Cys Thr Gly Glu Met Glu
    290                 295                 300

Thr Ser Gln Phe Pro Gly Glu Glu Lys Pro Gln Ala Ser Pro Glu Gly
305                 310                 315                 320

Arg Pro Glu Ser Glu Thr Ser Cys Leu Val Thr Thr Thr Asp Phe Gln
                325                 330                 335

Ile Gln Thr Glu Met Ala Ala Thr Met Glu Thr Ser Ile Phe Thr Thr
            340                 345                 350

Glu Tyr Gln
        355
```

```
<210> SEQ ID NO 46
<211> LENGTH: 375
<212> TYPE: PRT
<213> ORGANISM: Artificial Sequence
<220> FEATURE:
<223> OTHER INFORMATION: Synthesized unprocessed form IL-2
      (Gly3)- extracellular domain of IL-2 R

<400> SEQUENCE: 46

Met Asp Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Gly Gly Gly Glu Leu Cys Asp
145                 150                 155                 160

Asp Asp Pro Pro Glu Ile Pro His Ala Thr Phe Lys Ala Met Ala Tyr
                165                 170                 175

Lys Glu Gly Thr Met Leu Asn Cys Glu Cys Lys Arg Gly Phe Arg Arg
            180                 185                 190

Ile Lys Ser Gly Ser Leu Tyr Met Leu Cys Thr Gly Asn Ser Ser His
        195                 200                 205

Ser Ser Trp Asp Asn Gln Cys Gln Cys Thr Ser Ser Ala Thr Arg Asn
    210                 215                 220

Thr Thr Lys Gln Val Thr Pro Gln Pro Glu Glu Gln Lys Glu Arg Lys
225                 230                 235                 240

Thr Thr Glu Met Gln Ser Pro Met Gln Pro Val Asp Gln Ala Ser Leu
                245                 250                 255

Pro Gly His Cys Arg Glu Pro Pro Pro Trp Glu Asn Glu Ala Thr Glu
            260                 265                 270

Arg Ile Tyr His Phe Val Val Gly Gln Met Val Tyr Tyr Gln Cys Val
        275                 280                 285

Gln Gly Tyr Arg Ala Leu His Arg Gly Pro Ala Glu Ser Val Cys Lys
    290                 295                 300

Met Thr His Gly Lys Thr Arg Trp Thr Gln Pro Gln Leu Ile Cys Thr
305                 310                 315                 320

Gly Glu Met Glu Thr Ser Gln Phe Pro Gly Glu Glu Lys Pro Gln Ala
                325                 330                 335

Ser Pro Glu Gly Arg Pro Glu Ser Glu Thr Ser Cys Leu Val Thr Thr
            340                 345                 350

Thr Asp Phe Gln Ile Gln Thr Glu Met Ala Ala Thr Met Glu Thr Ser
        355                 360                 365
```

Ile Phe Thr Thr Glu Tyr Gln
    370              375

<210> SEQ ID NO 47
<211> LENGTH: 1170
<212> TYPE: DNA
<213> ORGANISM: Artificial Sequence
<220> FEATURE:
<223> OTHER INFORMATION: Synthesized unprocessed form IL-2
      (Gly3Ser)2- extracellular domain of IL-2 R

<400> SEQUENCE: 47

| | | |
|---|---|---|
| atggacagga tgcaactcct gtcttgcatt gcactaagtc ttgcacttgt cacaaacagt | 60 |
| gcacctactt caagttctac aaagaaaaca cagctacaac tggagcattt actgctggat | 120 |
| ttacagatga ttttgaatgg aattaataat tacaagaatc ccaaactcac caggatgctc | 180 |
| acatttaagt tttacatgcc caagaaggcc acagaactga acatcttca gtgtctagaa | 240 |
| gaagaactca aacctctgga ggaagtgcta aatttagctc aaagcaaaaa ctttcactta | 300 |
| agacccaggg acttaatcag caatatcaac gtaatagttc tggaactaaa gggatctgaa | 360 |
| acaacattca tgtgtgaata tgctgatgag acagcaacca ttgtagaatt tctgaacaga | 420 |
| tggattacct ttgtcaaag catcatctca cactgactg gtggaggttc tggtggaggt | 480 |
| tcagagctct gtgacgatga cccgccagag atcccacacg ccacattcaa agccatggcc | 540 |
| tacaaggaag gaaccatgtt gaactgtgaa tgcaagagag gtttccgcag aataaaaagc | 600 |
| gggtcactct atatgctctg tacaggaaac tctagccact cgtcctggga caaccaatgt | 660 |
| caatgcacaa gctctgccac tcggaacaca acgaaacaag tgacacctca acctgaagaa | 720 |
| cagaaagaaa ggaaaaccac agaaatgcaa agtccaatgc agccagtgga ccaagcgagc | 780 |
| cttccaggtc actgcaggga acctccacca tgggaaaatg aagccacaga gagaatttat | 840 |
| catttcgtgg tggggcagat ggtttattat cagtgcgtcc agggatacag ggctctacac | 900 |
| agaggtcctg ctgagagcgt ctgcaaaatg acccacggga gacaaggtg acccagccc | 960 |
| cagctcatat gcacaggtga atggagacc agtcagtttc aggtgaaga aagcctcag | 1020 |
| gcaagccccg aaggccgtcc tgagagtgag acttcctgcc tcgtcacaac aacagatttt | 1080 |
| caaatacaga cagaaatggc tgcaaccatg gagacgtcca tatttacaac agagtaccag | 1140 |
| ggtggacatc accatcacca tcactaataa | 1170 |

<210> SEQ ID NO 48
<211> LENGTH: 1155
<212> TYPE: DNA
<213> ORGANISM: Artificial Sequence
<220> FEATURE:
<223> OTHER INFORMATION: Synthesized unprocessed form IL-2
      (Gly3)- extracellular domain of IL-2 R

<400> SEQUENCE: 48

| | | |
|---|---|---|
| atggacagga tgcaactcct gtcttgcatt gcactaagtc ttgcacttgt cacaaacagt | 60 |
| gcacctactt caagttctac aaagaaaaca cagctacaac tggagcattt actgctggat | 120 |
| ttacagatga ttttgaatgg aattaataat tacaagaatc ccaaactcac caggatgctc | 180 |
| acatttaagt tttacatgcc caagaaggcc acagaactga acatcttca gtgtctagaa | 240 |
| gaagaactca aacctctgga ggaagtgcta aatttagctc aaagcaaaaa ctttcactta | 300 |
| agacccaggg acttaatcag caatatcaac gtaatagttc tggaactaaa gggatctgaa | 360 |
| acaacattca tgtgtgaata tgctgatgag acagcaacca ttgtagaatt tctgaacaga | 420 |

```
tggattacct tttgtcaaag catcatctca acactgactg gtggaggtga gctctgtgac    480
gatgacccgc cagagatccc acacgccaca ttcaaagcca tggcctacaa ggaaggaacc    540
atgttgaact gtgaatgcaa gagaggtttc cgcagaataa aaagcgggtc actctatatg    600
ctctgtacag gaaactctag ccactcgtcc tgggacaacc aatgtcaatg cacaagctct    660
gccactcgga acacaacgaa acaagtgaca cctcaacctg aagaacagaa agaaaggaaa    720
accacagaaa tgcaaagtcc aatgcagcca gtggaccaag cgagccttcc aggtcactgc    780
agggaacctc caccatggga aaatgaagcc acagagagaa tttatcattt cgtggtgggg    840
cagatggttt attatcagtg cgtccaggga tacagggctc tacacagagg tcctgctgag    900
agcgtctgca aaatgaccca cgggaagaca aggtggaccc agccccagct catatgcaca    960
ggtgaaatgg agaccagtca gtttccaggt gaagagaagc tcaggcaag ccccgaaggc   1020 cgtcctgaga gtgagacttc ctgcctcgtc acaacaacag attttcaaat acagacagaa   1080
atggctgcaa ccatggagac gtccatattt acaacagagt accagggtgg acatcaccat   1140
caccatcact aataa                                                    1155
```

<210> SEQ ID NO 49
<211> LENGTH: 1221
<212> TYPE: DNA
<213> ORGANISM: Artificial Sequence
<220> FEATURE:
<223> OTHER INFORMATION: Synthesized unprocessed form IL-2
      (Gly4Ser)5- extracellular domain of IL-2 R

<400> SEQUENCE: 49

```
atggacagga tgcaactcct gtcttgcatt gcactaagtc ttgcacttgt cacaaacagt     60
gcacctactt caagttctac aaagaaaaca cagctacaac tggagcattt actgctggat    120
ttacagatga ttttgaatgg aattaataat tacaagaatc ccaaactcac caggatgctc    180
acatttaagt tttacatgcc caagaaggcc acagaactga acatcttcca gtgtctagaa    240
gaagaactca aacctctgga ggaagtgcta aatttagctc aaagcaaaaa ctttcactta    300
agacccaggg acttaatcag caatatcaac gtaatagttc tggaactaaa gggatctgaa    360
acaacattca tgtgtgaata tgctgatgag acagcaacca ttgtagaatt ctgaacaga    420 tggattacct tttgtcaaag catcatctca acactgactg gtggaggtgg atcaggtgga    480
ggtggatctg gtggaggtgg atcaggtgga ggtggatccg gtggaggtgg atctgagctc    540
tgtgacgatg acccgccaga gatcccacac gccacattca aagccatggc ctacaaggaa    600
ggaaccatgt tgaactgtga atgcaagaga ggtttccgca gaataaaaag cgggtcactc    660
tatatgctct gtacaggaaa ctctagccac tcgtcctggg acaaccaatg tcaatgcaca    720
agctctgcca ctcggaacac aacgaaacaa gtgacacctc aacctgaaga acagaaagaa    780
aggaaaacca cagaaatgca aagtccaatg cagccagtgg accaagcgag ccttccaggt    840
cactgcaggg aacctccacc atgggaaaat gaagccacag agagaattta tcatttcgtg    900
gtggggcaga tggtttatta tcagtgcgtc cagggataca gggctctaca cagaggtcct    960
gctgagagcg tctgcaaaat gacccacggg aagacaaggt ggacccagcc ccagctcata   1020
tgcacaggtg aaatggagac cagtcagttt ccaggtgaag agaagcctca ggcaagcccc   1080
gaaggccgtc ctgagagtga gacttcctgc ctcgtcacaa caacagattt tcaaatacag   1140
acagaaatgg ctgcaaccat ggagacgtcc atatttacaa cagagtacca gggtggacat   1200
caccatcacc atcactaata a                                             1221
```

<210> SEQ ID NO 50
<211> LENGTH: 15
<212> TYPE: PRT
<213> ORGANISM: Artificial Sequence
<220> FEATURE:
<223> OTHER INFORMATION: (Gly4Ser)3 linker

<400> SEQUENCE: 50

Gly Gly Gly Gly Ser Gly Gly Gly Gly Ser Gly Gly Gly Gly Ser
1               5                   10                  15

<210> SEQ ID NO 51
<211> LENGTH: 10
<212> TYPE: PRT
<213> ORGANISM: Artificial Sequence
<220> FEATURE:
<223> OTHER INFORMATION: (Gly4Ser)2 linker

<400> SEQUENCE: 51

Gly Gly Gly Gly Ser Gly Gly Gly Gly Ser
1               5                   10

<210> SEQ ID NO 52
<211> LENGTH: 5
<212> TYPE: PRT
<213> ORGANISM: Artificial Sequence
<220> FEATURE:
<223> OTHER INFORMATION: (Gly4Ser)1 linker

<400> SEQUENCE: 52

Gly Gly Gly Gly Ser
1               5

<210> SEQ ID NO 53
<211> LENGTH: 10
<212> TYPE: DNA
<213> ORGANISM: Artificial Sequence
<220> FEATURE:
<223> OTHER INFORMATION: Kozak sequence

<400> SEQUENCE: 53
gccaccatgg                                                              10

<210> SEQ ID NO 54
<211> LENGTH: 412
<212> TYPE: PRT
<213> ORGANISM: Artificial Sequence
<220> FEATURE:
<223> OTHER INFORMATION: Synthesized unprocessed form of IL-2
      (Gly4Ser)4-extracellular domain of IL-2 R + glycine spacer and
      poly-histidine region

<400> SEQUENCE: 54

Met Asp Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
                20                  25                  30

Glu Ala Gln Gln Gln Gln Gln Gln Gln Gln Gln Gln Gln His Leu
        35                  40                  45

Glu Gln Leu Leu Met Asp Leu Gln Glu Leu Leu Ser Arg Met Glu Asn
    50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu

```
                    85                  90                  95
Leu Gly Pro Leu Arg His Val Leu Asp Leu Thr Gln Ser Lys Ser Phe
                100                 105                 110
Gln Leu Glu Asp Ala Glu Asn Phe Ile Ser Asn Ile Arg Val Thr Val
            115                 120                 125
Val Lys Leu Lys Gly Ser Asp Asn Thr Phe Glu Cys Gln Phe Asp Asp
130                 135                 140
Glu Ser Ala Thr Val Val Asp Phe Leu Arg Arg Trp Ile Ala Phe Cys
145                 150                 155                 160
Gln Ser Ile Ile Ser Thr Ser Pro Gln Gly Gly Gly Ser Gly Gly
                165                 170                 175
Gly Gly Ser Gly Gly Gly Ser Gly Gly Gly Ser Glu Leu Cys
                180                 185                 190
Leu Tyr Asp Pro Pro Glu Val Pro Asn Ala Thr Phe Lys Ala Leu Ser
            195                 200                 205
Tyr Lys Asn Gly Thr Ile Leu Asn Cys Glu Cys Lys Arg Gly Phe Arg
        210                 215                 220
Arg Leu Lys Glu Leu Val Tyr Met Arg Cys Leu Gly Asn Ser Trp Ser
225                 230                 235                 240
Ser Asn Cys Gln Cys Thr Ser Asn Ser His Asp Lys Ser Arg Lys Gln
                245                 250                 255
Val Thr Ala Gln Leu Glu His Gln Lys Glu Gln Gln Thr Thr Thr Asp
            260                 265                 270
Met Gln Lys Pro Thr Gln Ser Met His Gln Glu Asn Leu Thr Gly His
        275                 280                 285
Cys Arg Glu Pro Pro Pro Trp Lys His Glu Asp Ser Lys Arg Ile Tyr
290                 295                 300
His Phe Val Glu Gly Gln Ser Val His Tyr Glu Cys Ile Pro Gly Tyr
305                 310                 315                 320
Lys Ala Leu Gln Arg Gly Pro Ala Ile Ser Ile Cys Lys Met Lys Cys
                325                 330                 335
Gly Lys Thr Gly Trp Thr Gln Pro Gln Leu Thr Cys Val Asp Glu Arg
            340                 345                 350
Glu His His Arg Phe Leu Ala Ser Glu Glu Ser Gln Gly Ser Arg Asn
        355                 360                 365
Ser Ser Pro Glu Ser Glu Thr Ser Cys Pro Ile Thr Thr Thr Asp Phe
370                 375                 380
Pro Gln Pro Thr Glu Thr Thr Ala Met Thr Glu Thr Phe Val Leu Thr
385                 390                 395                 400
Met Glu Tyr Lys Gly Gly His His His His His
                405                 410

<210> SEQ ID NO 55
<211> LENGTH: 417
<212> TYPE: PRT
<213> ORGANISM: Artificial Sequence
<220> FEATURE:
<223> OTHER INFORMATION: Synthesized unprocessed form of IL-2
      (Gly4Ser)5- extracellular domain of IL-2 R + glycine spacer and
      poly-histidine region

<400> SEQUENCE: 55

Met Asp Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
            20                  25                  30
```

-continued

Glu Ala Gln Gln Gln Gln Gln Gln Gln Gln Gln Gln His Leu
            35                  40                  45

Glu Gln Leu Leu Met Asp Leu Gln Leu Leu Ser Arg Met Glu Asn
 50                  55                  60

Tyr Arg Asn Leu Lys Leu Pro Arg Met Leu Thr Phe Lys Phe Tyr Leu
65                   70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
            115                 120                 125

Val Lys Leu Lys Gly Ser Asp Asn Thr Phe Glu Cys Gln Phe Asp Asp
130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln Gly Gly Gly Ser Gly Gly
                165                 170                 175

Gly Gly Ser Gly Gly Gly Gly Ser Gly Gly Gly Gly Ser Gly Gly Gly
            180                 185                 190

Gly Ser Glu Leu Cys Leu Tyr Asp Pro Pro Glu Val Pro Asn Ala Thr
            195                 200                 205

Phe Lys Ala Leu Ser Tyr Lys Asn Gly Thr Ile Leu Asn Cys Glu Cys
210                 215                 220

Lys Arg Gly Phe Arg Arg Leu Lys Glu Leu Val Tyr Met Arg Cys Leu
225                 230                 235                 240

Gly Asn Ser Trp Ser Ser Asn Cys Gln Cys Thr Ser Asn Ser His Asp
                245                 250                 255

Lys Ser Arg Lys Gln Val Thr Ala Gln Leu Glu His Gln Lys Glu Gln
            260                 265                 270

Gln Thr Thr Thr Asp Met Gln Lys Pro Thr Gln Ser Met His Gln Glu
            275                 280                 285

Asn Leu Thr Gly His Cys Arg Glu Pro Pro Trp Lys His Glu Asp
            290                 295                 300

Ser Lys Arg Ile Tyr His Phe Val Glu Gly Gln Ser Val His Tyr Glu
305                 310                 315                 320

Cys Ile Pro Gly Tyr Lys Ala Leu Gln Arg Gly Pro Ala Ile Ser Ile
                325                 330                 335

Cys Lys Met Lys Cys Gly Lys Thr Gly Trp Thr Gln Pro Gln Leu Thr
            340                 345                 350

Cys Val Asp Glu Arg Glu His His Arg Phe Leu Ala Ser Glu Glu Ser
            355                 360                 365

Gln Gly Ser Arg Asn Ser Ser Pro Glu Ser Glu Thr Ser Cys Pro Ile
370                 375                 380

Thr Thr Thr Asp Phe Pro Gln Pro Thr Glu Thr Thr Ala Met Thr Glu
385                 390                 395                 400

Thr Phe Val Leu Thr Met Glu Tyr Lys Gly Gly His His His His
                405                 410                 415

His

<210> SEQ ID NO 56
<211> LENGTH: 408
<212> TYPE: PRT

<213> ORGANISM: Artificial Sequence
<220> FEATURE:
<223> OTHER INFORMATION: Synthesized unprocessed form of IL-2
    (Gly3Ser)4- extracellular domain of IL-2 R + glycine spacer and
    poly-histidine region

<400> SEQUENCE: 56

```
Met Asp Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
            20                  25                  30

Glu Ala Gln Gln Gln Gln Gln Gln Gln Gln Gln Gln Gln Gln His Leu
        35                  40                  45

Glu Gln Leu Leu Met Asp Leu Gln Glu Leu Leu Ser Arg Met Glu Asn
50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
        115                 120                 125

Val Lys Leu Lys Gly Ser Asp Asn Thr Phe Glu Cys Gln Phe Asp Asp
130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln Gly Gly Ser Gly Gly Gly Gly
                165                 170                 175

Ser Gly Gly Gly Ser Gly Gly Ser Glu Leu Cys Leu Tyr Asp Pro
            180                 185                 190

Pro Glu Val Pro Asn Ala Thr Phe Lys Ala Leu Ser Tyr Lys Asn Gly
        195                 200                 205

Thr Ile Leu Asn Cys Glu Cys Lys Arg Gly Phe Arg Arg Leu Lys Glu
210                 215                 220

Leu Val Tyr Met Arg Cys Leu Gly Asn Ser Trp Ser Asn Cys Gln
225                 230                 235                 240

Cys Thr Ser Asn Ser His Asp Lys Ser Arg Lys Gln Val Thr Ala Gln
                245                 250                 255

Leu Glu His Gln Lys Glu Gln Gln Thr Thr Thr Asp Met Gln Lys Pro
            260                 265                 270

Thr Gln Ser Met His Gln Glu Asn Leu Thr Gly His Cys Arg Glu Pro
        275                 280                 285

Pro Pro Trp Lys His Glu Asp Ser Lys Arg Ile Tyr His Phe Val Glu
290                 295                 300

Gly Gln Ser Val His Tyr Glu Cys Ile Pro Gly Tyr Lys Ala Leu Gln
305                 310                 315                 320

Arg Gly Pro Ala Ile Ser Ile Cys Lys Met Lys Cys Gly Lys Thr Gly
                325                 330                 335

Trp Thr Gln Pro Gln Leu Thr Cys Val Asp Glu Arg Glu His His Arg
            340                 345                 350

Phe Leu Ala Ser Glu Glu Ser Gln Gly Ser Arg Asn Ser Ser Pro Glu
        355                 360                 365

Ser Glu Thr Ser Cys Pro Ile Thr Thr Thr Asp Phe Pro Gln Pro Thr
370                 375                 380
```

Glu Thr Thr Ala Met Thr Glu Thr Phe Val Leu Thr Met Glu Tyr Lys
385                 390                 395                 400

Gly Gly His His His His His
                405

<210> SEQ ID NO 57
<211> LENGTH: 404
<212> TYPE: PRT
<213> ORGANISM: Artificial Sequence
<220> FEATURE:
<223> OTHER INFORMATION: Synthesized unprocessed form of IL-2
      (Gly3Ser)3- extracellular domain of IL-2 R + glycine spacer and
      poly-histidine region

<400> SEQUENCE: 57

Met Asp Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
                20                  25                  30

Glu Ala Gln Gln Gln Gln Gln Gln Gln Gln Gln Gln His Leu
            35                  40                  45

Glu Gln Leu Leu Met Asp Leu Gln Glu Leu Leu Ser Arg Met Glu Asn
50                  55                  60

Tyr Arg Asn Leu Lys Leu Pro Arg Met Leu Thr Phe Lys Phe Tyr Leu
65                  70                  75                  80

Pro Lys Gln Ala Thr Glu Leu Lys Asp Leu Gln Cys Leu Glu Asp Glu
                85                  90                  95

Leu Gly Pro Leu Arg His Val Leu Asp Leu Thr Gln Ser Lys Ser Phe
            100                 105                 110

Gln Leu Glu Asp Ala Glu Asn Phe Ile Ser Asn Ile Arg Val Thr Val
            115                 120                 125

Val Lys Leu Lys Gly Ser Asp Asn Thr Phe Glu Cys Gln Phe Asp Asp
130                 135                 140

Glu Ser Ala Thr Val Val Asp Phe Leu Arg Arg Trp Ile Ala Phe Cys
145                 150                 155                 160

Gln Ser Ile Ile Ser Thr Ser Pro Gln Gly Gly Gly Ser Gly Gly Gly
                165                 170                 175

Ser Gly Gly Gly Ser Glu Leu Cys Leu Tyr Asp Pro Pro Glu Val Pro
            180                 185                 190

Asn Ala Thr Phe Lys Ala Leu Ser Tyr Lys Asn Gly Thr Ile Leu Asn
            195                 200                 205

Cys Glu Cys Lys Arg Gly Phe Arg Arg Leu Lys Glu Leu Val Tyr Met
210                 215                 220

Arg Cys Leu Gly Asn Ser Trp Ser Ser Asn Cys Gln Cys Thr Ser Asn
225                 230                 235                 240

Ser His Asp Lys Ser Arg Lys Gln Val Thr Ala Gln Leu Glu His Gln
                245                 250                 255

Lys Glu Gln Gln Thr Thr Thr Asp Met Gln Lys Pro Thr Gln Ser Met
            260                 265                 270

His Gln Glu Asn Leu Thr Gly His Cys Arg Glu Pro Pro Trp Lys
            275                 280                 285

His Glu Asp Ser Lys Arg Ile Tyr His Phe Val Glu Gly Gln Ser Val
            290                 295                 300

His Tyr Glu Cys Ile Pro Gly Tyr Lys Ala Leu Gln Arg Gly Pro Ala
305                 310                 315                 320

```
Ile Ser Ile Cys Lys Met Lys Cys Gly Lys Thr Gly Trp Thr Gln Pro
                325                 330                 335

Gln Leu Thr Cys Val Asp Glu Arg Glu His His Arg Phe Leu Ala Ser
            340                 345                 350

Glu Glu Ser Gln Gly Ser Arg Asn Ser Ser Pro Glu Ser Glu Thr Ser
        355                 360                 365

Cys Pro Ile Thr Thr Thr Asp Phe Pro Gln Pro Thr Glu Thr Thr Ala
370                 375                 380

Met Thr Glu Thr Phe Val Leu Thr Met Glu Tyr Lys Gly Gly His His
385                 390                 395                 400

His His His His

<210> SEQ ID NO 58
<211> LENGTH: 388
<212> TYPE: PRT
<213> ORGANISM: Artificial Sequence
<220> FEATURE:
<223> OTHER INFORMATION: Synthesized unprocessed form IL-2
      (Gly3Ser)2- extracellular domain of IL-2 R + glycine spacer and
      poly-histidine region

<400> SEQUENCE: 58

Met Asp Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
            85                  90                  95

Asn Phe His Leu Arg Pro Arg Asp Leu Ile Ser Asn Ile Asn Val Ile
        100                 105                 110

Val Leu Glu Leu Lys Gly Ser Glu Thr Thr Phe Met Cys Glu Tyr Ala
    115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr Gly Gly Gly Ser Gly Gly Gly
145                 150                 155                 160

Ser Glu Leu Cys Asp Asp Asp Pro Pro Glu Ile Pro His Ala Thr Phe
            165                 170                 175

Lys Ala Met Ala Tyr Lys Glu Gly Thr Met Leu Asn Cys Glu Cys Lys
        180                 185                 190

Arg Gly Phe Arg Arg Ile Lys Ser Gly Ser Leu Tyr Met Leu Cys Thr
    195                 200                 205

Gly Asn Ser Ser His Ser Ser Trp Asp Asn Gln Cys Gln Cys Thr Ser
210                 215                 220

Ser Ala Thr Arg Asn Thr Thr Lys Gln Val Thr Pro Gln Pro Glu Glu
225                 230                 235                 240

Gln Lys Glu Arg Lys Thr Thr Glu Met Gln Ser Pro Met Gln Pro Val
            245                 250                 255

Asp Gln Ala Ser Leu Pro Gly His Cys Arg Glu Pro Pro Pro Trp Glu
        260                 265                 270
```

```
Asn Glu Ala Thr Glu Arg Ile Tyr His Phe Val Val Gly Gln Met Val
            275                 280                 285
Tyr Tyr Gln Cys Val Gln Gly Tyr Arg Ala Leu His Arg Gly Pro Ala
290                 295                 300
Glu Ser Val Cys Lys Met Thr His Gly Lys Thr Arg Trp Thr Gln Pro
305                 310                 315                 320
Gln Leu Ile Cys Thr Gly Glu Met Glu Thr Ser Gln Phe Pro Gly Glu
                325                 330                 335
Glu Lys Pro Gln Ala Ser Pro Glu Gly Arg Pro Glu Ser Glu Thr Ser
                340                 345                 350
Cys Leu Val Thr Thr Thr Asp Phe Gln Ile Gln Thr Glu Met Ala Ala
                355                 360                 365
Thr Met Glu Thr Ser Ile Phe Thr Thr Glu Tyr Gln Gly Gly His His
                370                 375                 380
His His His His
385

<210> SEQ ID NO 59
<211> LENGTH: 392
<212> TYPE: PRT
<213> ORGANISM: Artificial Sequence
<220> FEATURE:
<223> OTHER INFORMATION: Synthesized unprocessed form of IL-2
      (Gly3Ser)3- extracellular domain of IL-2 R + glycine spacer and
      poly-histidine region

<400> SEQUENCE: 59

Met Asp Arg Met Gln Leu Leu Ser Cys Ile Ala Leu Ser Leu Ala Leu
1               5                   10                  15
Val Thr Asn Ser Ala Pro Thr Ser Ser Ser Thr Lys Lys Thr Gln Leu
                20                  25                  30
Gln Leu Glu His Leu Leu Leu Asp Leu Gln Met Ile Leu Asn Gly Ile
            35                  40                  45
Asn Asn Tyr Lys Asn Pro Lys Leu Thr Arg Met Leu Thr Phe Lys Phe
        50                  55                  60
Tyr Met Pro Lys Lys Ala Thr Glu Leu Lys His Leu Gln Cys Leu Glu
65                  70                  75                  80
Glu Glu Leu Lys Pro Leu Glu Glu Val Leu Asn Leu Ala Gln Ser Lys
                85                  90                  95
Asn Phe His Leu Arg Pro Arg Asp Leu Ile Ser Asn Ile Asn Val Ile
            100                 105                 110
Val Leu Glu Leu Lys Gly Ser Glu Thr Thr Phe Met Cys Glu Tyr Ala
        115                 120                 125
Asp Glu Thr Ala Thr Ile Val Glu Phe Leu Asn Arg Trp Ile Thr Phe
130                 135                 140
Cys Gln Ser Ile Ile Ser Thr Leu Thr Gly Gly Gly Ser Gly Gly Gly
145                 150                 155                 160
Ser Gly Gly Gly Ser Glu Leu Cys Asp Asp Asp Pro Pro Glu Ile Pro
                165                 170                 175
His Ala Thr Phe Lys Ala Met Ala Tyr Lys Glu Gly Thr Met Leu Asn
            180                 185                 190
Cys Glu Cys Lys Arg Gly Phe Arg Arg Ile Lys Ser Gly Ser Leu Tyr
        195                 200                 205
Met Leu Cys Thr Gly Asn Ser Ser His Ser Ser Trp Asp Asn Gln Cys
210                 215                 220
```

```
Gln Cys Thr Ser Ser Ala Thr Arg Asn Thr Thr Lys Gln Val Thr Pro
225                 230                 235                 240

Gln Pro Glu Glu Gln Lys Glu Arg Lys Thr Thr Glu Met Gln Ser Pro
                245                 250                 255

Met Gln Pro Val Asp Gln Ala Ser Leu Pro Gly His Cys Arg Glu Pro
            260                 265                 270

Pro Pro Trp Glu Asn Glu Ala Thr Glu Arg Ile Tyr His Phe Val Val
        275                 280                 285

Gly Gln Met Val Tyr Tyr Gln Cys Val Gln Gly Tyr Arg Ala Leu His
    290                 295                 300

Arg Gly Pro Ala Glu Ser Val Cys Lys Met Thr His Gly Lys Thr Arg
305                 310                 315                 320

Trp Thr Gln Pro Gln Leu Ile Cys Thr Gly Glu Met Glu Thr Ser Gln
                325                 330                 335

Phe Pro Gly Glu Glu Lys Pro Gln Ala Ser Pro Glu Gly Arg Pro Glu
            340                 345                 350

Ser Glu Thr Ser Cys Leu Val Thr Thr Asp Phe Gln Ile Gln Thr
        355                 360                 365

Glu Met Ala Ala Thr Met Glu Thr Ser Ile Phe Thr Thr Glu Tyr Gln
370                 375                 380

Gly Gly His His His His His His
385                 390

<210> SEQ ID NO 60
<211> LENGTH: 396
<212> TYPE: PRT
<213> ORGANISM: Artificial Sequence
<220> FEATURE:
<223> OTHER INFORMATION: Synthesized unprocessed form IL-2
      (Gly3Ser)4- extracellular domain of IL-2 R + glycine spacer and
      poly-histidine region

<400> SEQUENCE: 60

Met Asp Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Gly Gly Gly Ser Gly Gly Gly
145                 150                 155                 160

Ser Gly Gly Gly Ser Gly Gly Gly Ser Glu Leu Cys Asp Asp Asp Pro
                165                 170                 175

Pro Glu Ile Pro His Ala Thr Phe Lys Ala Met Ala Tyr Lys Glu Gly
```

```
            180                 185                 190
Thr Met Leu Asn Cys Glu Cys Lys Arg Gly Phe Arg Arg Ile Lys Ser
            195                 200                 205
Gly Ser Leu Tyr Met Leu Cys Thr Gly Asn Ser Ser His Ser Ser Trp
            210                 215                 220
Asp Asn Gln Cys Gln Cys Thr Ser Ser Ala Thr Arg Asn Thr Thr Lys
225                 230                 235                 240
Gln Val Thr Pro Gln Pro Glu Glu Gln Lys Glu Arg Lys Thr Thr Glu
            245                 250                 255
Met Gln Ser Pro Met Gln Pro Val Asp Gln Ala Ser Leu Pro Gly His
            260                 265                 270
Cys Arg Glu Pro Pro Pro Trp Glu Asn Glu Ala Thr Glu Arg Ile Tyr
            275                 280                 285
His Phe Val Val Gly Gln Met Val Tyr Tyr Gln Cys Val Gln Gly Tyr
            290                 295                 300
Arg Ala Leu His Arg Gly Pro Ala Glu Ser Val Cys Lys Met Thr His
305                 310                 315                 320
Gly Lys Thr Arg Trp Thr Gln Pro Gln Leu Ile Cys Thr Gly Glu Met
            325                 330                 335
Glu Thr Ser Gln Phe Pro Gly Glu Glu Lys Pro Gln Ala Ser Pro Glu
            340                 345                 350
Gly Arg Pro Glu Ser Glu Thr Ser Cys Leu Val Thr Thr Thr Asp Phe
            355                 360                 365
Gln Ile Gln Thr Glu Met Ala Ala Thr Met Glu Thr Ser Ile Phe Thr
            370                 375                 380
Thr Glu Tyr Gln Gly Gly His His His His His His
385                 390                 395

<210> SEQ ID NO 61
<211> LENGTH: 400
<212> TYPE: PRT
<213> ORGANISM: Artificial Sequence
<220> FEATURE:
<223> OTHER INFORMATION: Synthesized unprocessed form IL-2
      (Gly4Ser)4- extracellular domain of IL-2 R + glycine spacer and
      poly-histidine region

<400> SEQUENCE: 61

Met Asp Arg Met Gln Leu Leu Ser Cys Ile Ala Leu Ser Leu Ala Leu
1               5                   10                  15
Val Thr Asn Ser Ala Pro Thr Ser Ser Ser Thr Lys Lys Thr Gln Leu
            20                  25                  30
Gln Leu Glu His Leu Leu Leu Asp Leu Gln Met Ile Leu Asn Gly Ile
            35                  40                  45
Asn Asn Tyr Lys Asn Pro Lys Leu Thr Arg Met Leu Thr Phe Lys Phe
        50                  55                  60
Tyr Met Pro Lys Lys Ala Thr Glu Leu Lys His Leu Gln Cys Leu Glu
65                  70                  75                  80
Glu Glu Leu Lys Pro Leu Glu Glu Val Leu Asn Leu Ala Gln Ser Lys
            85                  90                  95
Asn Phe His Leu Arg Pro Arg Asp Leu Ile Ser Asn Ile Asn Val Ile
            100                 105                 110
Val Leu Glu Leu Lys Gly Ser Glu Thr Thr Phe Met Cys Glu Tyr Ala
            115                 120                 125
Asp Glu Thr Ala Thr Ile Val Glu Phe Leu Asn Arg Trp Ile Thr Phe
            130                 135                 140
```

```
Cys Gln Ser Ile Ile Ser Thr Leu Thr Gly Gly Gly Ser Gly Gly
145                 150                 155                 160

Gly Gly Ser Gly Gly Gly Ser Gly Gly Gly Ser Glu Leu Cys
                165                 170                 175

Asp Asp Asp Pro Pro Glu Ile Pro His Ala Thr Phe Lys Ala Met Ala
            180                 185                 190

Tyr Lys Glu Gly Thr Met Leu Asn Cys Glu Cys Lys Arg Gly Phe Arg
        195                 200                 205

Arg Ile Lys Ser Gly Ser Leu Tyr Met Leu Cys Thr Gly Asn Ser Ser
    210                 215                 220

His Ser Ser Trp Asp Asn Gln Cys Gln Cys Thr Ser Ser Ala Thr Arg
225                 230                 235                 240

Asn Thr Thr Lys Gln Val Thr Pro Gln Pro Glu Glu Gln Lys Glu Arg
                245                 250                 255

Lys Thr Thr Glu Met Gln Ser Pro Met Gln Pro Val Asp Gln Ala Ser
            260                 265                 270

Leu Pro Gly His Cys Arg Glu Pro Pro Pro Trp Glu Asn Glu Ala Thr
        275                 280                 285

Glu Arg Ile Tyr His Phe Val Val Gly Gln Met Val Tyr Tyr Gln Cys
    290                 295                 300

Val Gln Gly Tyr Arg Ala Leu His Arg Gly Pro Ala Glu Ser Val Cys
305                 310                 315                 320

Lys Met Thr His Gly Lys Thr Arg Trp Thr Gln Pro Gln Leu Ile Cys
                325                 330                 335

Thr Gly Glu Met Glu Thr Ser Gln Phe Pro Gly Glu Glu Lys Pro Gln
            340                 345                 350

Ala Ser Pro Glu Gly Arg Pro Glu Ser Glu Thr Ser Cys Leu Val Thr
        355                 360                 365

Thr Thr Asp Phe Gln Ile Gln Thr Glu Met Ala Ala Thr Met Glu Thr
    370                 375                 380

Ser Ile Phe Thr Thr Glu Tyr Gln Gly Gly His His His His His
385                 390                 395                 400

<210> SEQ ID NO 62
<211> LENGTH: 364
<212> TYPE: PRT
<213> ORGANISM: Artificial Sequence
<220> FEATURE:
<223> OTHER INFORMATION: Synthesized mature form IL-2
      (Gly3Ser)3- extracellular domain of mutIL-2 R

<400> SEQUENCE: 62

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
```

```
              100                 105                 110
Thr Ile Val Glu Phe Leu Asn Arg Trp Ile Thr Phe Cys Gln Ser Ile
        115                 120                 125
Ile Ser Thr Leu Thr Gly Gly Ser Gly Gly Ser Gly Gly Gly
        130                 135                 140
Ser Glu Leu Cys Asp Asp Pro Pro Glu Ile Pro His Ala Thr Phe
145                 150                 155                 160
Lys Ala Met Ala Tyr Lys Glu Gly Thr Met Leu Asn Cys Glu Cys Lys
                165                 170                 175
Arg Gly Phe Thr Ser Ile Lys Ser Gly Ser Leu Tyr Met Leu Cys Thr
                180                 185                 190
Gly Asn Ser Ser His Ser Ser Trp Asp Asn Gln Cys Gln Cys Thr Ser
                195                 200                 205
Ser Ala Thr Arg Asn Thr Thr Lys Gln Val Thr Pro Gln Pro Glu Glu
        210                 215                 220
Gln Lys Glu Arg Lys Thr Thr Glu Met Gln Ser Pro Met Gln Pro Val
225                 230                 235                 240
Asp Gln Ala Ser Leu Pro Gly His Cys Arg Glu Pro Pro Trp Glu
                245                 250                 255
Asn Glu Ala Thr Glu Arg Ile Tyr His Phe Val Val Gly Gln Met Val
                260                 265                 270
Tyr Tyr Gln Cys Val Gln Gly Tyr Arg Ala Leu His Arg Gly Pro Ala
                275                 280                 285
Glu Ser Val Cys Lys Met Thr His Gly Lys Thr Arg Trp Thr Gln Pro
        290                 295                 300
Gln Leu Ile Cys Thr Gly Glu Met Glu Thr Ser Gln Phe Pro Gly Glu
305                 310                 315                 320
Glu Lys Pro Gln Ala Ser Pro Glu Gly Arg Pro Glu Ser Glu Thr Ser
                325                 330                 335
Cys Leu Val Thr Thr Thr Asp Phe Gln Ile Gln Thr Glu Met Ala Ala
                340                 345                 350
Thr Met Glu Thr Ser Ile Phe Thr Thr Glu Tyr Gln
        355                 360

<210> SEQ ID NO 63
<211> LENGTH: 1182
<212> TYPE: DNA
<213> ORGANISM: Artificial Sequence
<220> FEATURE:
<223> OTHER INFORMATION: Synthesized unprocessed form IL-2
      (Gly3Ser)3- extracellular domain of mutIL-2 R Mut

<400> SEQUENCE: 63
atggacagga tgcaactcct gtcttgcatt gcactaagtc ttgcacttgt cacaaacagt      60
gcacctactt caagttctac aaagaaaaca cagctacaac tggagcattt actgctggat     120
ttacagatga tttttgaatgg aattaataat acaagaatc ccaaactcac caggatgctc     180
acatttaagt tttacatgcc caagaaggcc acagaactga acatcttca gtgtctagaa     240 gaagaactca aacctctgga ggaagtgcta aatttagctc aaagcaaaaa ctttcactta     300
agacccaggg acttaatcag caatatcaac gtaatagttc tggaactaaa gggatctgaa     360
acaacattca gtgtgaata tgctgatgag acagcaacca ttgtagaatt tctgaacaga     420
tggattacct tttgtcaaag catcatctca cactgactg gtggaggttc tggtggaggt     480
tcaggtggag gttcggagct ctgtgacgat gacccgccag agatcccaca cgccacattc     540
```

```
aaagccatgg cctacaagga aggaaccatg ttgaactgtg aatgcaagag aggtttcacc      600
tcaataaaaa gcgggtcact ctatatgctc tgtacaggaa actctagcca ctcgtcctgg      660
gacaaccaat gtcaatgcac aagctctgcc actcggaaca caacgaaaca agtgacacct      720
caacctgaag aacagaaaga aaggaaaacc acagaaatgc aaagtccaat gcagccagtg      780
gaccaagcga gccttccagg tcactgcagg gaacctccac catgggaaaa tgaagccaca      840
gagagaattt atcatttcgt ggtggggcag atggtttatt atcagtgcgt ccagggatac      900
agggctctac acagaggtcc tgctgagagc gtctgcaaaa tgacccacgg aagacaagg       960 tggacccagc cccagctcat atgcacaggt gaaatggaga ccagtcagtt tccaggtgaa      1020
gagaagcctc aggcaagccc cgaaggccgt cctgagagtg agacttcctg cctcgtcaca     1080
acaacagatt ttcaaataca gacagaaatg gctgcaacca tggagacgtc catatttaca     1140
acagagtacc agggtggaca tcaccatcac catcactaat aa                        1182
```

<210> SEQ ID NO 64
<211> LENGTH: 372
<212> TYPE: PRT
<213> ORGANISM: Artificial Sequence
<220> FEATURE:
<223> OTHER INFORMATION: Synthesized mature form IL-2
(Gly4Ser)4- extracellular domain of mutIL-2 R

<400> SEQUENCE: 64

```
Ala Pro Thr Ser Ser Ser Thr Lys Lys Thr Gln Leu Gln Leu Glu His
  1               5                  10                  15

Leu Leu Leu Asp Leu Gln Met Ile Leu Asn Gly Ile Asn Asn Tyr Lys
             20                  25                  30

Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Gly Ser Gly Gly Gly Ser Gly
    130                 135                 140

Gly Gly Ser Gly Gly Gly Ser Glu Leu Cys Asp Asp Asp Pro
145                 150                 155                 160

Pro Glu Ile Pro His Ala Thr Phe Lys Ala Met Ala Tyr Lys Glu Gly
                165                 170                 175

Thr Met Leu Asn Cys Glu Cys Lys Arg Gly Phe Thr Ser Ile Lys Ser
            180                 185                 190

Gly Ser Leu Tyr Met Leu Cys Thr Gly Asn Ser Ser His Ser Ser Trp
        195                 200                 205

Asp Asn Gln Cys Gln Cys Thr Ser Ala Thr Arg Asn Thr Thr Lys
    210                 215                 220

Gln Val Thr Pro Gln Pro Glu Glu Gln Lys Glu Arg Lys Thr Thr Glu
225                 230                 235                 240

Met Gln Ser Pro Met Gln Pro Val Asp Gln Ala Ser Leu Pro Gly His
```

```
                   245                 250                 255
Cys Arg Glu Pro Pro Trp Glu Asn Glu Ala Thr Glu Arg Ile Tyr
            260                 265                 270

His Phe Val Val Gly Gln Met Val Tyr Tyr Gln Cys Val Gln Gly Tyr
            275                 280                 285

Arg Ala Leu His Arg Gly Pro Ala Glu Ser Val Cys Lys Met Thr His
    290                 295                 300

Gly Lys Thr Arg Trp Thr Gln Pro Gln Leu Ile Cys Thr Gly Glu Met
305                 310                 315                 320

Glu Thr Ser Gln Phe Pro Gly Glu Glu Lys Pro Gln Ala Ser Pro Glu
                325                 330                 335

Gly Arg Pro Glu Ser Glu Thr Ser Cys Leu Val Thr Thr Thr Asp Phe
            340                 345                 350

Gln Ile Gln Thr Glu Met Ala Ala Thr Met Glu Thr Ser Ile Phe Thr
            355                 360                 365

Thr Glu Tyr Gln
    370

<210> SEQ ID NO 65
<211> LENGTH: 1206
<212> TYPE: DNA
<213> ORGANISM: Artificial Sequence
<220> FEATURE:
<223> OTHER INFORMATION: Synthesized unprocessed form IL-2
      (Gly4Ser)4- extracellular domain of mutIL-2 R

<400> SEQUENCE: 65
atggacagga tgcaactcct gtcttgcatt gcactaagtc ttgcacttgt cacaaacagt      60
gcacctactt caagttctac aaagaaaaca cagctacaac tggagcattt actgctggat    120
ttacagatga ttttgaatgg aattaataat acaagaatcc caaactcac caggatgctc      180 acatttaagt tttacatgcc caagaaggcc acagaactga acatcttca gtgtctagaa      240 gaagaactca aacctctgga ggaagtgcta aatttagctc aaagcaaaaa ctttcactta    300
agacccaggg acttaatcag caatatcaac gtaatagttc tggaactaaa gggatctgaa    360
acaacattca tgtgtgaata tgctgatgag acagcaacca ttgtagaatt tctgaacaga    420
tggattacct tttgtcaaag catcatctca cactgactg gtggaggtgg atctggtgga    480
ggtggatcag gtggaggtgg atccggtgga ggtggatctg agctctgtga cgatgacccg    540
ccagagatcc cacacgccac attcaaagcc atggcctaca ggaaggaac catgttgaac    600 tgtgaatgca agagaggttt cacctcaata aaaagcgggt cactctatat gctctgtaca    660
ggaaactcta gccactcgtc ctgggacaac aatgtcaat gcacaagctc tgccactcgg    720
aacacaacga aacaagtgac acctcaacct gaagaacaga agaaaggaa accacagaa    780 atgcaaagtc aatgcagcc agtggaccaa gcgagccttc aggtcactg cagggaacct    840 ccaccatggg aaaatgaagc cacagagaga atttatcatt tcgtggtggg cagatggtt    900 tattatcagt gcgtccaggg atacagggct ctacacagag gtcctgctga gagcgtctgc    960
aaaatgaccc acgggaagac aaggtggacc cagccccagc tcatatgcac aggtgaaatg   1020
gagaccagtc agtttccagg tgaagagaag cctcaggcaa gccccgaagg ccgtcctgag   1080
agtgagactt cctgcctcgt cacaacaaca gattttcaaa tacagacaga aatggctgca   1140
accatggaga cgtccatatt tacaacagag taccagggtg acatcacca tcaccatcac   1200 taataa                                                               1206
```